(12) United States Patent
Anderson

(10) Patent No.: US 6,638,621 B2
(45) Date of Patent: Oct. 28, 2003

(54) COATED PARTICLES, METHODS OF MAKING AND USING

(75) Inventor: David Anderson, Colonial Heights, VA (US)

(73) Assignee: Lyotropic Therapeutics, Inc., Ashland, VA (US)

( * ) Notice: Subject to any disclaimer, the term of this patent is extended or adjusted under 35 U.S.C. 154(b) by 0 days.

(21) Appl. No.: 10/170,237

(22) Filed: Jun. 13, 2002

(65) Prior Publication Data

US 2003/0108743 A1 Jun. 12, 2003

Related U.S. Application Data

(63) Continuation-in-part of application No. 09/297,997, filed on Aug. 16, 2000, now Pat. No. 6,482,517.
(51) Int. Cl.[7] .............................................. B32B 15/02
(52) U.S. Cl. .................. 428/402.24; 424/422; 424/426; 424/450; 435/176
(58) Field of Search ...................... 428/402.24; 424/422, 424/426, 450; 435/176

(56) References Cited

U.S. PATENT DOCUMENTS

| | | | | |
|---|---|---|---|---|
| 5,321,014 | A | * | 6/1994 | Janz et al. ..................... 514/58 |
| 2002/0153508 | A1 | | 10/2002 | Lynch et al. |
| 2002/0153509 | A1 | | 10/2002 | Lynch et al. |
| 2002/0158226 | A1 | | 10/2002 | Lynch et al. |
| 2002/0160040 | A1 | | 10/2002 | Spicer et al. |
| 2003/0039668 | A1 | * | 2/2003 | Gulla et al. |

* cited by examiner

*Primary Examiner*—Terressa M. Boykin
(74) *Attorney, Agent, or Firm*—Whitham, Curtis & Christofferson, P.C.

(57) ABSTRACT

A particle coated with a nonlamellar material such as a nonlamellar crystalline material, a nonlamellar amorphous material, or a nonlamellar semi-crystalline material includes an internal matrix core having at least one a nanostructured liquid phase, or at least on nanostructured liquid crystalline phase or a combination of the two is used for the delivery of active agents such as pharmaceuticals, nutrients, pesticides, etc. The coated particle can be fabricated by a variety of different techniques where the exterior coating is a nonlamellar material such as a nonlamellar crystalline material, a nonlamellar amorphous material, or a nonlamellar semi-crystalline material.

107 Claims, 11 Drawing Sheets

COATED PARTICLES, METHODS OF MAKING AND USING

This application is a continuation-in-part of allowed U.S. patent application Ser. No. 09/297,997 filed Aug. 16, 2000 now U.S. Pat. No. 6,482,517, the complete contents of which are hereby incorporated by reference.

BACKGROUND OF THE INVENTION

1. Field of the Invention

The present invention relates to coated particles and to methods of making and using them. These coated particles have application in the targeting and release of one or more materials into selected environments, the absorption of one or more materials from selected environments and the adsorption of one or more materials from selected environments.

2. Related Art

Two particle technologies-polymer-coated particles and liposomes—are of general interest.

Polymer-coated particles have been very important in the development of useful microparticles and of controlled-release vehicles generally. In certain circumstances polymers have coating and spreading properties that provide for good encapsulation of various matrices, and they are available in a range of chemistries and molecular weights. Certain polymeric coatings are of such utility and low toxicity that approval has been obtained for their use even in injectable products within the pharmaceutical industry, most notably polylactic-glycolic acid copolymers, and the usefulness of polymeric coatings in oral products is well-established, as in the cases of Eudragits, gelatin, and a number of natural gums. In many settings in fact, microparticle coatings are tacitly assumed to be polymers.

However, polymer-coated particles exhibit several limitations, as the flattened and diffuse response of their polymer coatings to chemical and physical triggers indicates. This is due to two factors. First, the high molecular weight of polymers reduces their diffusion coefficients and their kinetics of solubilization. Second, the neighboring group effect broadens the curves representing the chemical responses to triggers such as, inter alia, pH, salinity, oxidation and reduction, ionization, etc. (The neighboring group effect indicates that chemical changes in one monomeric unit of a polymer significantly alter the parameters governing chemical transitions in each of the neighboring monomeric units.) Further, most polymers are collections of chemical species of broadened molecular weight distribution. In addition, for a given application of the polymer coated particle only a limited number of suitable polymers are frequently available. This is due to a number of factors: regulatory issues: the coating processes often entail harsh chemical and/or physical conditions, such as solvents, free radicals, elevated temperatures, dessication or drying, and/or macroscopic shearing forces needed to form the particles; the limited mechanical and thermal stabilities of the polymeric coatings in industrial applications; and adverse environmental impacts in large scale applications of polymer-coated particles, such as in agricultural use.

Liposomes also exhibit a number of limitations. Among these are their physical and chemical instabilities. The release of a material disposed within the liposome is usually dependent on the destabilization of the structure of the liposome. In particular, the absence of porosity precludes the pore-controlled release of such materials. The dual requirements of 1) physical stability of the liposome until release is desired on the one hand and 2) release of materials by bilayer destabilization when release is desired on the other, are problematic. (The term liposomes is frequently interchanged with the term vesicles and is usually reserved for vesicles of glycerophospholipids or other natural lipids. Vesicles are self-supported closed bilayer assemblies of several thousand lipid molecules (amphiphiles) that enclose an aqueous interior volume. The lipid bilayer is a two-dimensional fluid composed of lipids with their hydrophilic head groups exposed to the aqueous solution and their hydrophobic tails aggregated to exclude water. The bilayer structure is highly ordered yet dynamic because of the rapid lateral motion of the lipids within the plane of each half of the bilayer.) See O'Brien. D. F. and Rarnaswami, V. (1989) in Mark-Bikales-Overberger-Menges Encyclopedia of Polymer Science and Engineering. Vol. 17, Ed. John Wiley & Inc., p. 108.

SUMMARY OF THE INVENTION

It is an object of the invention to provide coated particles that are suitable for solubilizing or containing a wide variety of materials, including materials sensitive to physical, chemical or biological deterioration.

It is an object of the invention to provide coated particles that release one or more material disposed within a matrix in their internal cores without requiring the destabilization of that matrix.

It is an object of the invention to provide coated particles covering a wide range of physical and chemical properties, particularly in the selection of the coating, such that a user can substantially preselect the coating and release characteristics.

It is an object of the invention to provide coated particles that sharply initiate the release or absorption of one or more materials to or from a selected environment in response to one or more physical or chemical triggers.

It is an object of the invention to provide a wide variety of coated particle systems that can be tailored to the particular physical, chemical and biological requirements of their contemplated use, such as mechanical and thermal stability in industrial applications of the coated particles or freedom from adverse environmental impact in large scale application of the coated particles in agricultural use.

It is an object of the invention to provide coated particles that provide, if desired, a porous coating that permits pore-controlled release of material disposed within them or pore-controlled absorption of materials disposed without them.

It is a further object of the invention to provide coated particles that can incorporate targeting moieties such as antibodies, lectins, receptors, and complementary nucleic acids, for targeting the particles to specific sites, either before or after the coating releases, as well as other bioactive materials such as absorption enhancers, adjuvants, adsorption inhibitors, or pharmaceutical actives themselves.

It is a further object of the invention to provide coated particles that can be produced by a process that is flexible and can be adapted to a wide range of actives, coatings, and matrices.

It is a further object of the invention to provide coated particles that have a polymerized interior matrix which is more permanent chemically, thermodynamically, and structurally than their unpolymerized counterparts.

It is a still further object of the invention to provide coated particles that can be made by a simple process, including, preferably, without entailing harsh physical and/or chemical conditions.

The foregoing and other objects are provided by a coated particle that comprises an internal core comprising a matrix and an exterior coating. The matrix consists essentially of at least one nanostructured liquid phase, or at least one nanostructured liquid crystalline phase or a combination of the two and the exterior coating comprises a nonlamellar material that is a nonlamellar crystalline material, a nonlamellar amorphous material, or a nonlamellar semi-crystalline material.

In a preferred embodiment, the coated particle may be made by 1. providing a volume of the matrix that includes at least one chemical species having a moiety capable of forming a nonlamellar material upon reaction with a second moiety and
2. contacting the volume with a fluid containing at least one chemical species having the second moiety under nonlamellar solid material-forming conditions so as to react the first moiety with the second moiety, and subdividing the volume into particles by the application of energy to the volume, or performing this subdivision into particles before, and/or after, the chemical reaction.

Alternatively, the coated particle can be made by one of the following processes:

providing a volume of the matrix that includes a material in solution in it that is capable of forming a nonlamellar material that is insoluble in the matrix and causing the aforesaid material to become insoluble in the matrix and subdividing the volume into particles by the application of energy to the volume;

dispersing particles of said matrix into a fluid that includes at least one chemical species having a moiety capable of forming a nonlamellar material upon reaction or association with a second moiety and adding to said dispersion at least one chemical species having said second moiety to react said first moiety with said second moiety;

dispersing particles of said matrix into a fluid that includes at least one chemical species having a moiety capable of forming a nonlamellar material upon reaction or association with a second moiety, adding to said dispersion at least one chemical species having said second moiety to react said first moiety with said second moiety, and subdividing the resulting material into particles by the application of energy to said material;

dispersing a volume of said matrix in a form of said nonlamellar material selected from the group consisting of liquefied form, solution, or fluid precursor, and solidifying said nonlamellar material by a techniques selected from the group consisting of cooling, evaporating a volatile solvent, or implementing a chemical reaction; or dispersing or dissolving a volume of said matrix in a liquid comprising said nonlamellar material in solution or dispersed form and comprising also a volatile solvent, and spray-drying said solution or dispersion.

Or, a combination of these methods can be applied.

DETAILED DESCRIPTION OF THE PREFERRED EMBODIMENTS

Figure 1:
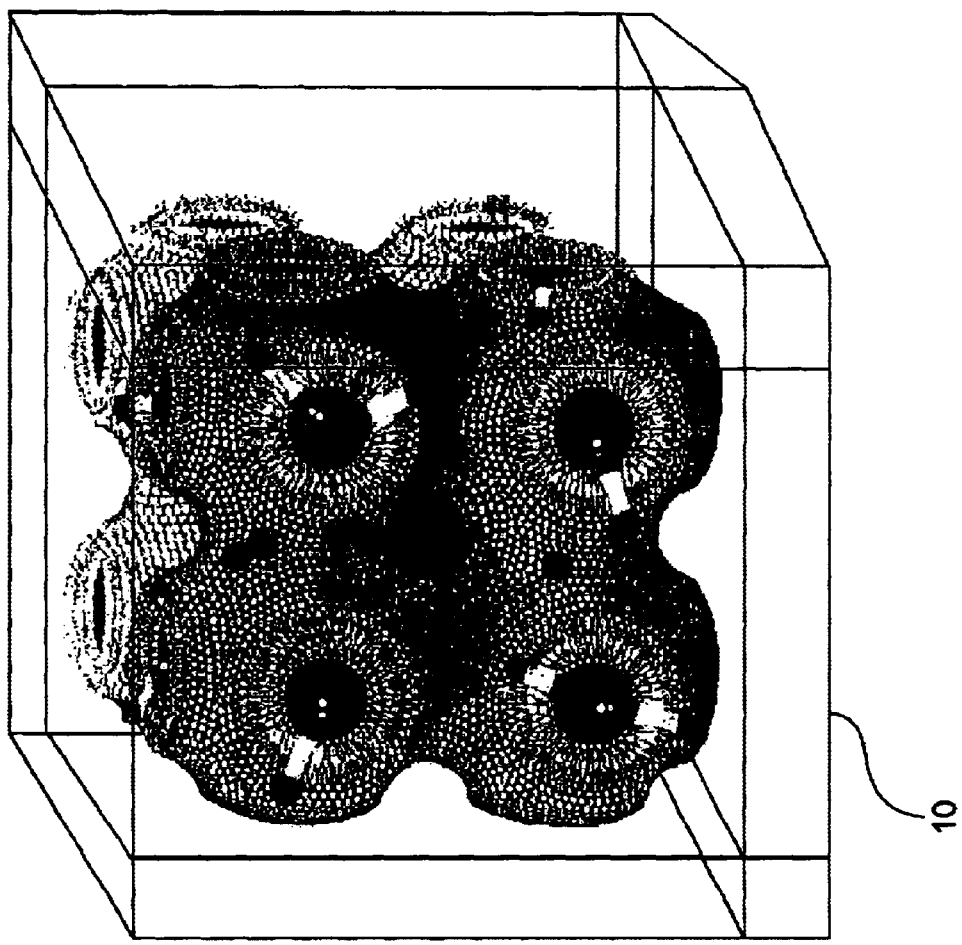
FIG. 1 is a graphic representation, in vertical section, illustrating a coated particle of the present invention comprising an internal core comprising a 2 by 2 by 2 unit cell matrix and an exterior coating.
Figure 2:
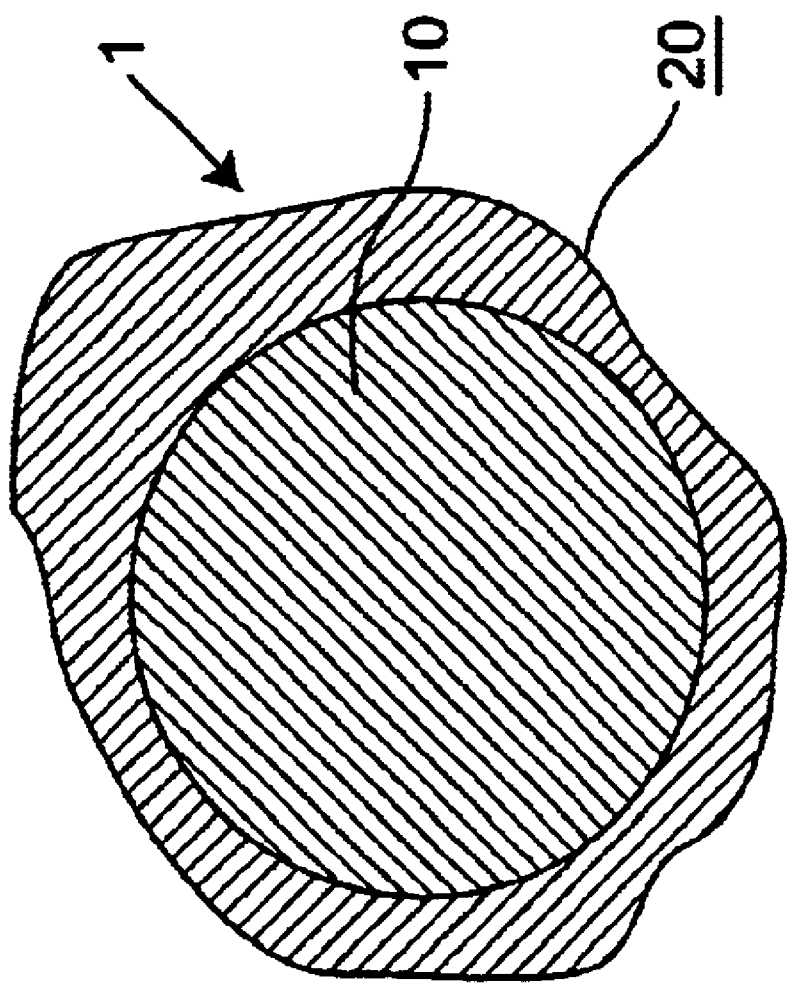
FIG. 2 is a graphic representation, in section, illustrating a coated particle of the present invention.

As illustrated in FIGS. 1 and 2, a coated particle 1 used in the present invention comprises an internal core 10 and a coating 20 exterior to it (hereinafter "exterior coating 20"). The internal core 10 comprises a matrix consisting essentially of a nanostructured material selected from the group consisting of a. at least one nanostructured liquid phase,
b. at least one nanostructured liquid crystalline phase and
c. a combination of
    i. at least one nanostructured liquid phase and
    ii. at least one nanostructured liquid crystalline phase.

Alternatively, the interior could be a composition that yields one of these phases upon contact with water or other aqueous fluid.

The liquid phase material and the liquid crystalline phase material may either contain solvent (lyotropic) or not contain solvent (thermotropic). The exterior coating 20 comprises a nonlamellar material. The term "exterior coating" as used herein is intended to indicate that the coating 20 is exterior to the internal core 10 and is not intended to be limited to meaning that the exterior coating 20 is the most exterior coating of the coated particle 1. For instance, in many of the Examples given herein, a surfactant-rich layer is present at the outer surface of the non-lamellar exterior coating. And in other embodiments presented, an antibody or other bioactive material will be adsorbed to, or extending out from, this non-lamellar exterior coating.

Nanostructured liquid phase and nanostructured liquid crystalline phase possess unique properties that are not only important in making possible the easy production of particles according to the present invention, but also yield highly desirable solubilization, stability, and presentation properties and other capabilities in the final coated particles of the present invention.

As for the exterior coating 20, non-lamellar structures which exhibit bonding and/or packing rigidity that extends in all three dimensions are strongly preferred in the present invention over lamellar materials, due to the well-known physical and chemical limitations and instabilities of lamellar, and more generally layered, structures, as exemplified by, for example, (a) the instability (even when acquiescent) of emulsions which have droplets coated with lamellar liquid crystalline layers, (b) the chemical instability upon removal of guest molecules in certain Werner complexes, and (c) the dramatically inferior hardness and shear modulus for graphite as compared with diamond.

Coated particles 1 used in the present invention may be from 0.1 micron to 30 microns or above in mean caliper diameter, and preferably from about 0.2 micron to about 5 microns in mean caliper diameter. Macroscopic particles can be made as well, i.e., particles with sizes measured in millimeters or even larger, as exemplified in Examples 39 and 40; the ability to make particles of this larger size could open up applications of the present invention in, for example, depot delivery systems for sustained release upon implantation. The coated particle 1 used may also be provided with a stabilizing layer on its exterior, i.e. outside the exterior coating 20 as desired, such as a polyelectrolyte or surfactant monolayer to prevent agglomeration of coated particles 1.

The coated particles 1 used in the present invention have application in a variety of modalities of use. The coated particle 1 may, upon release of the exterior coating 20, absorb one or more materials from a selected environment, adsorb one or more materials from a selected environment or release one or more materials, such as active agents disposed in the matrix, into a selected environment, and/or target specific sites for the intended release or ad/absorption. Alternatively, certain exterior coatings possessing porosity, such as inclusion compounds and zeolites, do not require release in order to effect the absorption or release of a material of interest into or out of the matrix, and in some such cases very high selectivity can be obtained by the use of properly tuned pore characteristics. In cases where the particles are used to adsorb a compound or compounds of interest, neither porosity nor release of the exterior coating 20 are required, but porosity can provide for a very large increase in adsorption capacity by allowing the adsorbed material to diffuse into the matrix, making the adsorption sites in the exterior coating 20 available to adsorb new material. In a preferred embodiment, an additional material, such as an active agent, may be disposed within the matrix for release into a selected environment.

Coating: In the present context of particles, a "coating" is composed of a material which behaves as a solid in the common sense, and in the engineering viewpoint, of the term "solid", namely that it exhibits a rigidity and permanence that contrasts sharply with low-viscosity liquids, and thus represents a significant diffusional barrier to the passage of compounds across that material, in a way that is intuitively different from any protection that a low-viscosity liquid layer could provide. This common sense understanding of the terms "liquid" and "solid" differs fundamentally from the strict scientific definitions, which refer only to the existence or non-existence of long-range atomic order. Thus, while an amorphous material such as PMMA (Plexiglass) or ordinary glass-particles of which make up an everyday coating known as ceramic glaze-may technically be a liquid, for the purposes of simplifying nomenclature in the context of this invention these materials will be referred to as solids, as they would in ordinary life outside of the physics laboratory.

The matrix is
 a. thermodynamically stable
 b. nanostructured and
 c. a liquid phase or liquid crystalline phase or a combination thereof.

Nanostructured: The terms "nanostructure" or "nanostructured" as used herein in the context of the structure of a material refer to materials the building blocks of which have a size that is on the order of nanometers ($10^{-9}$ meter) or tens of nanometers ($10 \times 10^{-9}$ meter). Generally speaking, any material that contains domains or particles 1 to 100 nm (nanometers) across, or layers or filaments of that thickness, can be considered a nanostructured material. (See also Dagani, R., "Nanostructured Materials Promise to Advance Range of Technologies." Nov. 23, 1992 C&E News 18 (1992).) The term is meant to exclude so-called "ceramic glasses" which are crystalline materials in which the crystallite size is so small that one may not observe peaks in wide-angle x-ray diffraction and which some physicists may refer to as nanostructured materials: the nanostructured liquid and liquid crystalline phases that are defined herein are characterized by nanoscale domains which are clearly distinguished from neighboring domains by large differences in local chemical composition, and do not include materials in which neighboring domains have essentially the same local chemical composition and differ only in lattice orientation. Thus, by the term 'domain' as used herein it is meant a spatial region which is characterized by a particular chemical makeup which is clearly distinguishable from that of neighboring domains: often such a domain is hydrophilic (hydrophobic) which contrasts with the hydrophobicity (hydrophilicity) of neighboring domains: in the context of this invention the characteristic size of these domains is in the nanometer range. (The term 'microdomain' is often used to indicate domains whose size range is micron or nanometer scale.)

Nanostructured liquids and liquid crystals: Nanostructured liquid phases and liquid crystalline phases, which provide the matrix of the internal cores 10 of the coated particles 1 in the present invention, possess unique collections of properties that are not only crucial in making possible the production of particles of the present invention, but also yield highly desirable solubilization, stability, and presentation properties and capabilities in the final coated particles. As discussed in more detail below in the discussion of particle production processes, in order that a material provide for ready dispersibility with one of the processes described herein, it is desirable for the material to be of very low solubility in water (otherwise it will tend to dissolve during the dispersing process, limiting dispersibility), yet, at the same time it should contain water—both for the purpose of solubilizing water-soluble reactants used in dispersing and for making possible the solubilization of a large range of active compounds.

In particular, for solubilization of hydrophilic (especially charged) and amphiphilic compounds, and for the maintenance of not only solubilization but also proper conformation and activity, of sensitive compounds of biological origin such as proteins, the interior matrix should contain substantial concentrations of water or other polar solvent. In terms of establishing versatility in coating selection, a great many (perhaps a majority) of the compounds listed as useful coatings in the present invention require reactants that are soluble only in polar solvents. Furthermore, the use of organic solvents for solubilization is in most cases inconsistent with the present matrices and/or with active biological compounds such as proteins (used in the present invention as actives or as targeting agents), and in any case is highly disfavored from regulatory, environmental, and health considerations. These two requirements of water-insolubility and solubilization of water-soluble compounds are, of course, working in opposite directions and are difficult to resolve in a single, inexpensive, and safe material.

Very effective systems for satisfying such solubilization requirements are provided by lipid—water systems, in which microdomains are present which are very high in water content, and simultaneously hydrophobic domains are in very close contact with the aqueous domains. The presence of aqueous domains circumvents precipitation tendencies encountered in systems where water structure is interrupted by the presence of high loadings of co-solvents or co-solutes, as, for example, in concentrated aqueous polymer solutions. At the same time the proximity of hydrophobic domains provides for effective solubilization of amphiphilic compounds (and hydrophobic as well).

Nanostructured liquid and liquid crystalline phases are synthetic or semisynthetic materials which adopt these solubilization characteristics, and provide pure, well-characterized, easily produced, and typically inexpensive matrices that also have the following desirable properties:

a) versatility in chemical systems forming nanostructured liquid phases and nanostructured liquid crystalline phases, ranging from biological lipids that are ideal for biomolecules, to hardy fluorosurfactants, to glycolipids that bind bacteria, to surfactants with ionic or reactive groups, etc. This provides for applicability over a wide range of conditions and uses;

b) the unsurpassed ability of nanostructured liquid phases and nanostructured liquid crystalline phases to: i) solubilize a wide range of active compounds including many traditionally difficult compounds such as Paclitaxel and biopharmaceuticals, circumventing the need for toxic and increasingly regulated organic solvents; ii) achieve high concentrations of actives with uncompromised stability, and iii) provide the biochemical environment that preserves their structure and function;

c) true thermodynamic stability, which greatly reduces instabilities common with other vehicles, such as precipitation of active agents, breaking of emulsions, vesicle fusion, etc., and, d) the presence of a porespace with preselectable pore size in the nanometer range, facilitating further control of the release kinetics even after triggered release of the coating, particularly in the release of proteins and other biomacromolecules.

The desired properties of the nanostructured material of the internal core 10 derive from several related concepts regarding materials that can be described with respect to surfactants by use of the terms "polar," "apolar," "amphiphile," "surfactant" and the "polar-apolar interface, and analogously with respect to block copolymer systems, as described below.

Polar: polar compounds (such as water) and polar moieties (such as the charged head groups on ionic surfactants or on lipids) are water-loving or hydrophilic: "polar" and "hydrophilic" in the context of the present invention are essentially synonymous. In terms of solvents, water is not the only polar solvent. Others of importance in the context of the present Invention are: glycerol, ethylene glycol, formamide, N-methyl formamide, dimethylformamide, ethylammonium nitrate, acetamide, N-methylacetamide, dimethylacetamide, N-methyl sydnone, and polyethylene glycol. Note that one of these (polyethylene glycol) is actually a polymer, thereby illustrating the range of possibilities. At sufficiently low molecular weights, polyethylene glycol (PEG) is a liquid, and although PEG has not been extensively studied as a polar solvent in combination with surfactants, it has been found that PEG does form nanostructured liquid phases and liquid crystalline phases in combination with, for example, surfactants such as BRIJ-type surfactants, which are nonionic surfactants with PEG head groups ether-linked to alkane chains. More generally, in terms of polar groups in hydrophilic and amphiphilic molecules (including but not limited to polar solvents and surfactants), a number of polar groups are tabulated below, in the discussion of which polar groups are operative as surfactant head groups and which are not.

Apolar. An apolar compound is a compound that has no dominant polar group. Apolar (or hydrophobic, or alternatively, "lipophilic") compounds include not only the paraffinic/hydrocarbon/alkane chains of surfactants, but also modifications of them, such as perfluorinated alkanes, as well as other hydrophobic groups such as the fused-ring structure in cholic acid as found in bile salt surfactants, or phenyl groups as form a portion of the apolar group in Triton-type surfactants, and oligomer and polymer chains that run the gamut from polyethylene (which represents a long alkane chain) to hydrophobic polymers such as hydrophobic polypeptide chains in novel peptide-based surfactants that have been investigated. A listing of some apolar groups and compounds is given below, in the discussion of useful components of the nanostructured phase interior. An apolar compound will be lacking in polar groups, a tabulation of which is included herein, and will generally have an octanol-water partition coefficient greater than about 100, and usually greater than about 1,000.

Amphiphile: an amphiphile can be defined as a compound that contains both a hydrophilic and a lipophilic group. See D. H. Everett. Pure and Applied Chemistry, vol. 31. no. 6, p. 611,1972. It is important to note that not every amphiphile is a surfactant. For example, butanol is an amphiphile, since the butyl group is lipophilic and the hydroxyl group hydrophilic, but it is not a surfactant since it does not satisfy the definition, given below. There exist a great many amphiphilic molecules possessing functional groups which are highly polar and hydrated to a measurable degree, yet which fail to display surfactant behavior. See R. Laughlin, Advances in liquid crystals, vol. 3. p. 41, 1978.

Surfactant: A surfactant is an amphiphile that possesses two additional properties. First, it significantly modifies the interfacial physics of the aqueous phase (at not only the air-water but also the oil-water and solid-water interfaces) at unusually low concentrations compared to nonsurfactants. Second, surfactant molecules associate reversibly with each other (and with numerous other molecules) to a highly exaggerated degree to form thermodynamically stable, macroscopically one-phase, solutions of aggregates or micelles. Micelles are typically composed of many surfactant molecules (10's to 1000's) and possess colloidal dimensions. See R. Laughlin, Advances in liquid crystals, vol. 3, p. 41, 1978. Lipids and polar lipids in particular, often are considered as surfactants for the purposes of discussion herein, although the term 'lipid' is normally used to indicate that they belong to a subclass of surfactants which have slightly different characteristics than compounds which are normally called surfactants in everyday discussion. Two characteristics which frequently, though not always, are possessed by lipids are first, they are often of biological origin, and second, they tend to be more soluble in oils and fats than in water. Indeed, many compounds referred to as lipids have extremely low solubilities in water, and thus the presence of a hydrophobic solvent may be necessary in order for the interfacial tension-reducing properties and reversible self-association to be most clearly evidenced, for lipids which are indeed surfactants. Thus, for example, such a compound will strongly reduce the interfacial tension between oil and water at low concentrations, even though extremely low solubility in water might make observation of surface tension reduction in the aqueous system difficult. Similarly, the addition of a hydrophobic solvent to a lipid-water system might make the determination of self-association into nanostructured liquid phases and nanostructured liquid crystalline phases a much simpler matter, whereas difficulties associated with high temperatures might make this difficult in the lipid-water system.

Indeed, it has been in the study of nanostructured liquid crystalline structures that the commonality between what had previously been considered intrinsically different— 'lipids' and 'surfactants'—came to the forefront, and the two schools of study (lipids, coming from the biological side, and surfactants, coming from the more industrial side) came together as the same nanostructures were observed in lipids as for all surfactants. In addition, it also came to the forefront that certain synthetic surfactants, such as dihexadecyldimethylammonium bromide, which were entirely of synthetic, non-biological origin, showed 'lipid-like' behavior in that hydrophobic solvents were needed for convenient demonstration of their surfactancy. On the other end, certain lipids such as lysolipids, which are clearly of biological origin, display phase behavior more or less typical of water-soluble surfactants. Eventually, it became clear that for purposes of discussing and comparing self-association and interfacial tension-reducing properties, a more meaningful distinction was between single-tailed and double-tailed compounds, where single-tailed generally implies water-soluble and double-tailed generally oil soluble.

Thus, in the present context, any amphiphile which at very low concentrations lowers interfacial tensions between water and hydrophobe, whether the hydrophobe be air or oil, and which exhibits reversible self-association into nanostructured micellar, inverted micellar, or bicontinuous morphologies in water or oil or both, is a surfactant. The class of lipids simply includes a subclass consisting of surfactants which are of biological origin.

Polar-apolar interface: In a surfactant molecule, one can find a dividing point (or in some cases two points, if there are polar groups at each end, or even more than two, as in Lipid A, which has seven acyl chains and thus seven dividing points per molecule), in the molecule that divide the polar part of the molecule from the apolar part. In any nanostructured liquid phase or nanostructured liquid crystalline phase, the surfactant forms monolayer or bilayer films: in such a film, the locus of the dividing points of the molecules describes a surface that divides polar domains from apolar domains: this is called the "polar-apolar interface" or "polar-apolar dividing surface." For example, in the case of a spherical micelle, this surface would be approximated by a sphere lying inside the outer surface of the micelle, with the polar groups of the surfactant molecules outside the surface and apolar chains inside it. Care should be taken not to confuse this microscopic interface with macroscopic interfaces separating two bulk phases that are seen by the naked eye.

Bicontinuous: In a bicontinuous structure, the geometry is described by two distinct, multiply-connected, intertwined subspaces each of which is continuous in all three dimensions; thus, it is possible to traverse the entire span of this space in any direction even if the path is restricted to one or other of the two subspaces. In a bicontinuous structure, each of the subspaces is rich in one type of material or moiety, and the two subspaces are occupied by two such materials or moieties each of which extends throughout the space in all three dimensions. Sponge, sandstone, apple, and many sinters are examples of relatively permanent though chaotic bicontinuous structures in the material realm. In these particular examples, one of the subspaces is occupied by a solid that is more or less deformable and the other subspace, though it may be referred to as void, is occupied by a fluid. Certain lyotropic liquid crystalline states are also examples, one subspace being occupied by amphiphile molecules oriented and aggregated into sheet-like arrays that are ordered geometrically, the other subspace being occupied by solvent molecules. Related liquid crystalline states that contain two incompatible kinds of solvent molecules, e.g. hydrocarbon and water, present a further possibility in which one subspace is rich in the first solvent, the other in the second, and the surface between lies within a multiply connected stratum rich in oriented surfactant molecules. Certain equilibrium microemulsion phases that contain comparable amounts of hydrocarbon and water as well as amphiphilic surfactant may be chaotic bicontinuous structures, maintained in a permanent state of fluctuating disorder by thermal motions, for they give no evidence of geometric order but there is compelling evidence for multiple continuity. Bicontinuous morphologies occur also in certain phase-segregated block copolymers. See Anderson. D. M., Davis. H. T., Nitsche. J. C. C. and Scriven. L. E. (1900) Advances in Chemical Physics, 77:337.

Chemical criteria: A number of criteria have been tabulated and discussed in detail by Robert Laughlin for determining whether a given polar group is functional as a surfactant head group, where the definition of surfactant includes the formation in water of nanostructured phases even at rather low concentrations. R. Laughlin, Advances in Liquid Crystals, pp. 3–41, 1978.

The following listing given by Laughlin gives some polar groups which are not operative as surfactant head groups— and thus, for example, an alkane chain linked to one of these polar groups would not be expected to form nanostructured liquid or liquid crystalline phases—are: aldehyde, ketone, carboxylic ester, carboxylic acid, isocyanate, amide, acyl cyanoguanidine, acvl guanyl urea, acyl biuret, N.N-dimethylamide, nitrosoalkane, nitroalkane, nitrate ester, nitrite ester, nitrone, nitrosamine, pyridine N-oxide, nitrile, isonitrile, amine borane, amine haloborane, sulfone, phosphine sulfide, arsine sulfide, sulfonamide, sulfonamide methylimine, alcohol (monofunctional), ester (monofunctional), secondary amine, tertiary amine, mercaptan, thioether, primary phosphine, secondary phosphine, and tertiary phosphine.

Some polar groups which are operative as surfactant head groups, and thus, for example, an alkane chain linked to one of these polar groups would be expected to form nanostructured liquid and liquid crystalline phases, are:
 a. Anionics: carboxylate (soap), sulfate, sulfamate, sulfonate, thiosulfate, sulfinate, phosphate, phosphonate, phosphinate, nitroamide, tris (alkylsulfonyl)methide, xanthate;
 b. Cationics: ammonium, pyridinium, phosphonium, sulfonium, sulfoxonium;

c. Zwiterionics: ammonio acetate, phosphoniopropane sulfonate, pyridinioethyl sulfate;

d. Semipolars: amine oxide, phosphonyl, phosphine oxide, arsine oxide, sulfoxide, sulfoximine, sulfone diimine, ammonio amidate.

Laughlin also demonstrates that as a general rule, if the enthalpy of formation of a 1:1 association complex of a given polar group with phenol (a hydrogen bonding donor) is less than 5 kcal, then the polar group will not be operative as a surfactant head group.

In addition to the polar head group, a surfactant requires an apolar group, and again there are guidelines for an effective apolar group. For alkane chains, which are of course the most common, if n is the number of carbons, then n must be at least 6 for surfactant association behavior to occur, although at least 8 or 10 is the usual case. Interestingly octylamine, with n=8 and the amine head group which is just polar enough to be effective as a head group, exhibits a lamellar phase with water at ambient temperature, as well as a nanostructured L2 phase. Warnhelm. T., Bergenstahl. B., Henriksson. U., Malmvik. A.-C. and Nilsson. P. (1987) J. of Colloid and Interface Sci. 118:233. Branched hydrocarbons yield basically the same requirement on the low n end: for example, sodium 2-ethylhexylsulfate exhibits a full range of liquid crystalline phases. Winsor, P. A. (1968) Chem. Rev. 68:1. However, the two cases of linear and branched hydrocarbons are vastly different on the high n side. With linear, saturated alkane chains, the tendency to crystallize is such that for n greater than about 18, the Krafft temperature becomes high and the temperature range of nanostructured liquid and liquid crystalline phases increases to high temperatures, near or exceeding 100° C. In the context of the present invention, for most applications this renders these surfactants considerably less useful than those with n between 8 and 18. With the introduction of unsaturation or branching in the chains, the range of n can increase dramatically. The case of unsaturation can be illustrated with the case of lipids derived from fish oils, where chains with 22 carbons can have extremely low melting points due to the presence of as many as 6 double bonds, as in docosahexadienoic acid and its derivatives, which include monoglycerides, soaps, etc. Furthermore, polybutadiene of very high MW is an elastomeric polymer at ambient temperature, and block copolymers with polybutadiene blocks are well known to yield nanostructured liquid crystals. Similarly, with the introduction of branching one can produce hydrocarbon polymers such as polypropyleneoxide (PPO) which serves as the hydrophobic block in a number of amphiphilic block copolymer surfactants of great importance, such as the Pluronic series of surfactants. Substitution of fluorine for hydrogen, in particular the use of perfluorinated chains, in surfactants generally lowers the requirement on the minimal value of n, as exemplified by lithium perfluourooctanoate (n=8), which displays a full range of liquid crystalline phases, including an intermediate phase which is fairly rare in surfactant systems. As discussed elsewhere, other hydrophobic groups, such as the fused-ring structure in the cholate soaps (bile salts), also serve as effective apolar groups, although such cases must generally be treated on a case by case basis in terms of determining whether a particular hydrophobic group will yield surfactant behavior.

For single-component block copolymers, relatively simple mean-field statistical theories are sufficient to predict when nanostructure liquid phase and liquid crystalline phase materials will occur and these are quite general over a wide range of block copolymers. If $\chi$ is the FloryHuzuins interaction parameter between polymer blocks A and B, and N is the total index of polymerization defined as the number of statistical units or monomer units in the polymer chain, consistently with the definition of the interaction parameter of the block copolymer, then nanostructure liquid and liquid crystalline phases are expected when the product $\chi N$ is greater than 10.5. Leibler, L. (1980) Macromolecules 13:1602. For values comparable to but larger than this critical value of 10.5, ordered nanostructured (liquid crystalline) phases can occur, including ever, bicontinuous cubic phases. Hajduk,. D. A., Harper, P. E., Gruner, S. M., Honeker, C. C., Kim, G., Thomas, E. L. and Fetters, L. J. (1994) Macromolecules 27:4063.

The Nanostructured Liquid Phases of Utility.

The nanostructured liquid phase material suitable for the nanostructured material of the matrix may be a. a nanostructured L1 phase material, b. a nanostructured L2 phase material.

c. a nanostructured microemulsion or d. a nanostructured L3 phase material.

The nanostructured liquid phases are characterized by domain structures composed of domains of at least a first type and a second type (and in some cases three or even more types) having the following properties:

a) the chemical moieties in the first type domains are incompatible with those in the second type domains (and in general, each pair of different domain types are mutually incompatible) such that they do not mix under the given conditions but rather remain as separate domains: for example, the first type domains could be composed substantially of polar moieties such as water and lipid head groups, while the second type domains could be composed substantially of apolar moieties such as hydrocarbon chains: or, first type domains could be polystyrene-rich, while second type domains are polyisoprene-rich and third type domains are polyvinylpyrrolidone-rich;

b) the atomic ordering within each domain is liquid-like rather than solid-like, i.e., it lacks lattice-ordering of the atoms; this would be evidenced by an absence of sharp Bragg peak reflections in wide-angle x-ray diffraction;

c) the smallest dimension (e.g., thickness in the case of layers, diameter in the case of cylinder-like or sphere-like domains) of substantially all domains is in the range of nanometers (viz., from about 1 to about 100 nm); and d) the organization of the domains does not exhibit long-range order nor conform to any periodic lattice. This is evidenced by the absence of sharp Bragg reflections in small-angle x-ray scattering examination of the phase. Furthermore, as seen below, if high viscosity and birefringence are both lacking, this is strong evidence of a liquid, as opposed to liquid crystalline, phase.

With respect to each of the liquid phases, systems based on surfactants, where the two types of domains in the nanostructured liquid are 'polar' and 'apolar' are initially discussed. Generally, following that, systems based on block copolymers are discussed. In these systems the terms 'polar' and 'apolar' may or may not be applicable, but there exist domain types 'A', 'B', etc., where as defined above (in the definition of a nanostructure liquid) domain types 'A' and 'B' are immiscible with respect to each other.

L1 phase: In an L1 phase that occurs in a system based on surfactants, the curvature of the polar-apolar interface is toward the apolar (non-polar) regions, generally resulting in particles—normal micelles—that exist in a water-continuous medium. (Here "water" refers to any polar solvent). When these micelles transform from spherical to cylindrical as conditions or compositions change, they can start to fuse together and bicontinuity can result. In addition to the water continuity, the hydrophobic domains can connect up to form a sample-spanning network: this can still be an L1 phase. In addition, there are examples of L1 phases that show evidence of having no microstructure whatsoever. That is, there are no micelles, no well-defined domains, just surfactant molecules co-mingled in a structureless, one-phase liquid solution that is thus not a nanostructured material. These "structureless solutions" can sometimes be changed to nanostructured phases by simple change in composition without any phase change in between. In other words, thermodynamics does not dictate a phase boundary between a structureless solution and a nanostructured phase. This is, of course, in contrast with the case of a transition between a phase having long-range order (a liquid crystal or a crystal) and a phase lacking long-range order (a liquid), where a phase boundary is required by thermodynamics.

For L1 phases that occur in systems based on block copolymers, the terms 'polar' and apolar may not apply, but in any case there are two (or in some cases more) domain types; we make the convention that the curvature of the A/B interface is toward A domains, so that a typical nanostructure would consist of particles, often sphere-like, of domain type A located in a continuum of B domains. As an example, in polystyrene-polyisoprene diblock copolymers, if the volume fraction of polystyrene blocks is very low, say 10%, then the usual microstructure will be polystyrene-rich spheres in a continuous polyisoprene matrix. Contrariwise, polyisoprene-rich spheres in a polystyrene-continuous matrix would be the likely structure for a 10% polyisoprene PS-PI diblock.

Identification of the nanostructured L1 phase. Since the L1 phase is a liquid phase, techniques have been developed to distinguished the nanostructured L1 phase from unstructured solution liquid phases. In addition to the experimental probes that are discussed below, there is a well-known body of knowledge that provides criteria by which one can determine a priori whether a given system should be expected to form nanostructured phases instead of simple unstructured solutions.

Since the formation of nanostructured liquid phases and nanostructured liquid crystalline phases is one requirement in the definition of a surfactant, in the discrimination of a nanostructured liquid from an unstructured solution it is extremely valuable to have criteria for determining whether a given compound is in fact a surfactant, criteria which provide for a number of tests for surfactancy in addition to methods discussed below for directly analyzing, the liquid in question. A number of criteria have been discussed by Robert Laughlin in Advances in Liquid Crystals, 3:41, 1978. To begin with, Laughlin lists chemical criteria for determining a priori whether a given compound will be a surfactant, and this was discussed in detail above. If, based on these criteria, a compound is expected to be a true surfactant, then the compound is expected to form nanostructured phases in water. In addition, with such a compound in the presence of water and hydrophobe, nanostructured phases are also expected to form normally, incorporating at least a portion of the hydrophobe present.

In the event that a non-surfactant amphiphile is added to such a system, and in particular an amphiphilic organic solvent such as a short-chained alcohol, dioxane, tetrahydrofuran, dimethylformamide, acetonitrile, dimethylsulfoxide, etc., then structureless liquids could form as the action of the organic solvent will generally be to disrupt colloidal aggregates and cosolubilize all the components.

Laughlin also goes on to discuss a number of criteria based on physical observations. One well-known criteria is the critical micelle concentration (CMC) which is observed in surface tension measurements. If the surface tension of an aqueous solution of the compound in question is plotted as a function of the concentration, then at very low concentrations, the surface tension will be seen to drop off sharply if the added compound is indeed a surfactant. Then, at a particular concentration known as the CMC, a sharp break will occur in this plot as the slope of the line decreases drastically, to the right of the CMC, so that the surface tension decreases much less with added surfactant. The reason is that above the CMC, added surfactant goes almost entirely into the creation of micelles rather than to the air-water interface.

A second criterion tabulated by Laughlin is the liquid crystal criterion: if the compound forms liquid crystals at high concentrations, then it must be a surfactant and will form liquid crystalline phases at concentrations lower than those at which the occur. In particular, the L1 phase is usually found at concentrations of surfactant just lower than those that form normal hexagonal, or in some cases normal non-bicontinuous cubic phase liquid crystals.

Another criterion discussed by Laughlin is based on the temperature differential between the upper limit of the Krafft boundary plateau and the melting point of the anhydrous compound. The Krafft boundary is a curve in the phase diagram of the binary system with compound and water: below he Krafft line are crystals- and above the Krafft line the crystals melt, so that there is a dramatic increase in solubility over a very narrow temperature range along the Krafft line. In the case of a true surfactant, this temperature differential is substantial: for example, in sodium palmitate, the melting point of the anhydrous compound is 288° C., while the Krafft line has its plateau at 69° C., so that the differential is 219° C. Laughlin goes on to discuss the case of dodecylamine, which has a temperature differential of 14° C., and has a small region in the phase diagram corresponding to liquid crystals, thus indicating a modest degree of association colloid behavior. In contrast; neither dodecylmethylamine nor dodecanol exhibit association behavior of the surfactant type, and both have zero temperature differential.

As in the case of liquid crystals, as discussed herein, given a material there are a number of experimental probes one can use to determine whether or not the material, in this case a liquid, is nanostrutured, and these will be discussed in the context of the L1 phase, although they apply to all nano-structured liquids, with the appropriate modifications. In such a determination, it is best to combine as many of these characterizations as feasible.

As with all the liquid phases, the L1 phase is optically isotropic in the absence of flow. It does not give a splitting in the $^2H$ NMR bandshape with deuterated surfactant.

Also, in examination with crossed polarizing filters, the L1 phase of surfactant systems does not generally give birefringence even under moderate flow conditions. The situation with respect to birefringence in the case of block copolymer-based systems is complicated by the possibility of strain birefringence, so this is not a reliable method in that case.

Returning to the surfactant-based L1 phase, viscosity is generally quite low, considerably lower than in liquid crystals in the same system.

Using pulsed-gradient NMR to measure the effective self-diffusion coefficients of the various components, one finds that the self-diffusion of surfactant, and any added hydrophobe is very low, typically on the order of $10^{-13}$ m$^2$/sec or less (unless the phase is bicontinuous: see below). This is because the primary means for diffusion of surfactant and hydrophobe is by diffusion of entire micelles, which is very slow. Also, the diffusion rates of surfactant and of hydrophobe should be nearly the same, for the same reason.

Small-angle x-ray scattering (SAXS) does not give sharp Bragg peaks in the nanometer range (nor any range), of course. However, analysis of the entire curve by several methods from the literature can give the length scale of the nanostructure. By analyzing the falloff of intensity at low wave numbers (but not too low compared to the inverse of the surfactant molecule length), one can determine the apparent radius of gyration: one plots intensity, versus the square of the wave number, and takes the slope to deduce $R_g$ (the so-called Guinier plot). The radius of gyration is then related to the dimensions of the micellar units by standard well-known formulae. This will fall in the range of nanometers. In addition, by plotting the product of intensity times the square of the wave number versus the wave number— the so-called 'Hosemann plot'—one will find a peak that can also be related to the dimensions of the micelles; this has the advantage that it is less sensitive to interactions between micelles than is the radius of gyration.

For surfactant-based L1 phases which are bicontinuous, the above will change as follows: First, the viscosity can increase considerably when bicontinuity occurs, do to the rigidity of the surfactant film, which is continuous. Also, the self-diffusion rate of the surfactant and even of added hydrophobe (which can be deliberately added to a binary system as a marker) can increase dramatically, approaching or even exceeding the values in a lamellar phase in the same system. And while SAXS analyses, both the radius of gyration and the Hosemann plot, will give resulting dimensions in the nanometer range, these must be interpreted as characteristic length scales of the bicontinuous domain structure, rather than as dimensions of discrete particles. In some models, such as the interconnected cylinders model of the author's thesis, or the Talmon-Prager model, a bicontinuous domain structure is represented as made up of units which although seemingly 'particles' are in reality only building blocks for construction of a model bicontinuous geometry.

For L1 phases in block copolymer-based systems, this same SAXS analysis holds. In contrast, NMR bandshape and self-diffusion measurements in general do not carry over, nor do surface tension measurements. However, vapor transport measurements have been used in the past in place of NMR self-diffusion, in particular, if one can find a gas which is preferentially soluble in one of the domain types but not in the other(s), then one can test for continuity of those domains by measuring the transport of that gas through the sample. If this is possible, then transport through the continuous domains (type B) in the micellar phase should be only slightly slower than that in the pure B polymer, whereas gas transport for a gas confined to A domains should be very low.

The shear modulus of a block copolymer-based micellar phase is determined largely by that of the polymer block forming the continuous domains, polymer B in our convention. Thus, for example, in a PS-PI diblock which is 10% PS, so that PS micelles form in a continuous PI matrix, the shear modulus would be close to that of pure polyisoprene with only a slight increase due to the presence of the PS micelles.

Interestingly, in the reverse case, with 90% PS and thus PI micelles in a continuous PS matrix, the elastomeric PI micelles can provide a shock-absorbing component which can improve the fracture characteristics over those of pure, glassy polystyrene.

L2 phase: This phase is the same as the L1 phase except that the roles of the polar region and the apolar region are reversed: the curvature of the polar-apolar interface is toward the polar domains, the interior of the micelles (if they exist) is water and/or other polar moieties, and the apolar domains (typically alkane chains of a lipid) form a continuous matrix—although it is possible for the polar domains also to connect up to form a bicontinuous L2 phase. As above, this phase can be either nanostructured or structureless.

Identification of the nanostructured L2 phase. The guidelines for making a phase identification of the nanostructured L2 phase are the same as those given above for the L1 phase, with the following modifications. We need only discuss the surfactant-based L2 phase, since in the block copolymer-based systems the two types of micellar phases (A in B, and B in A) are equivalent, and above we discussed the identification of the micellar phase in block copolymer systems.

First, L2 phases are generally more prominent when the HLB is low, for example with ethoxylated alcohol surfactants having a small number of ethylene oxide groups (usually 5 or less, with typical alkyl chain lengths), or with double-chained surfactants. In terms of phase behavior, they generally occur at higher surfactant concentrations than even the reversed liquid crystalline phases: a location that is very common is for the L2 phase to border the reversed hexagonal phase at higher surfactant concentrations. For L1 phases which are not bicontinuous, it is the water self-diffusion which is very low, and measurement of the diffusion coefficient (by pulsed-gradient NMR, for example) should give a number on the order of $10^{-11}$ m$^2$/sec or less. Also, a Hosemann plot will give the size of the reversed micelles, which will essentially be the water domain size.

Microemulsion: A microemulsion may be defined as a thermodynamically stable, low viscosity, optically isotropic liquid phase containing oil (apolar liquid), water (polar liquid), and surfactant. See also Danielsson. I. and Lindman. B. (1981) Colloids and Surfaces, 3:391. Thermodynamically stable liquid mixtures of surfactant, water and oil are usually referred to as microemulsions. While being macroscopically homogeneous, they are structured on a microscopic length scale (10–1,000 Angstrom) into aqueous and oleic microdomains separated by a surfactant-rich film. See Skurtveit, R. and Olsson, U. (1991) J. Phys. Chem. 95:5353. A key defining feature of a microemulsion is that it contains an "oil" (apolar solvent or liquid), in addition to water and surfactant; it is always microstructured by definition. In general, because of the strong tendency for oil and water to phase segregate, in the absence of an organic solvent capable of co-solubilizing oil and water (such as ethanol, THF, dioxane, DMF, acetonitrile, dimethylsulfoxide, and a few others), a clear, single-phase liquid containing water and surfactant must be a microemulsion, and one can safely conclude on that basis alone that the phase is nanostructured. Note that a microemulsion can also be an L1 or L2 phase especially, if it contains well-defined micelles; however, if it is an L1 phase then the micelles are necessarily swollen with oil. The microemulsion is a nanostructured liquid phase. If a liquid with "oil," water and surfactant has a characteristic domain size larger than the nanometer range, that is, in the micron range, then it is no longer a microemulsion but rather a "miniemulsion" or plain emulsion; both of the latter are non-equilibrium. The term microemulsion was introduced, despite the fact that L1 and L2 phases can contain oil, and can even be bicontinuous, because it is fairly common for three-component oil-water-surfactant/lipid systems to evolve continuously from water-continuous to bicontinuous to oil-continuous with no phase boundaries in between. In this case, it does not make sense to try to set a dividing point between the "L1" and "L2" regions of the phase diagram; so instead, one just refers to the whole region as "microemulsion"—recognizing that at the high-water-content end of this region the structure is that of an oil-swollen L1 phase, and at the high-oil-content end of this region the structure is that of an L2 phase. (In terms of Venn diagrams, there are overlaps between microemulsions and L1 and L2 phases, though not between L1 and L2 phases). As discussed below, the microstructure of microemulsions is quite generally describable in terms of a monolayer film of surfactant that divides oil-rich domains from water-rich domains. This surfactant/lipid-rich dividing film can enclose to form micelles, or connect up into a network structure to form a bicontinuous microemulsion.

It must be pointed out that an emulsion is not a nanostructured liquid, as the term is applied herein. To begin with, the characteristic length scale in an emulsion, which essentially is the average size of an emulsion droplet, is generally much larger than the characteristic length scale in a nanostructured liquid, and falls in the range of microns instead of nanometers. While recent efforts to produce emulsions with submicron droplet sizes have given rise to smaller droplet emulsions and to the advent of the term "miniemulsion", there remain crucial differences which exclude emulsions and miniemulsions from the realm of nanostructured liquid phases as applied herein. The nanostructured liquid phases described herein, including microemulsions, exist at thermodynamic equilibrium, in contrast to emulsions which are not equilibrium phases but only metastable materials. Furthermore, a nanostructured liquid which is acquiescent and fully equilibrated is optically transparent, whereas an emulsion is generally opaque—ordinary milk is an emulsion, for example. In addition, if one takes the model of Friberg for the structure of an ordinary emulsion to be true, and this is generally recognized in the field, then the distinction at the molecular scale can be seen to be dramatic. According to that model, emulsion droplets can generally be seen to be stabilized by interfacial films which upon microscopic examination typically prove to be films of nanostructured liquid crystalline phase material; thus, these emulsions have a hierarchical structure in which a nanostructured phase plays the role of a stabilizing layer between the main building blocks, which are the emulsion droplets and the continuous medium. Our use of the term "nanostructured" instead of "microstructured" is based on the more precise and restricted nature of the term "nanostructured" and its exclusion of other liquid phases which fall into an entirely different realm, such as emulsions. Clearly, simple geometric considerations dictate that an emulsion which has droplets on the order of 10 microns in size, and a stabilizing film which may be a liquid crystalline layer, is not appropriate as the interior of a microparticle of the present invention which generally has a size on the order of 1 micron.

Determination of nanostructured microemulsions. The methods and guidelines discussed above for determination of nanostructured L1 phases carry over to the determination of nanostructured microemulsion phases, with the following variations.

For microemulsions which do not clearly fall under either the L1 phase or the L2 phase descriptions—which is the remaining case to be treated here—we take note that many, if not most, of these are bicontinuous, and in the context of a single liquid phase containing oil, water and surfactant, bicontinuity provides strong proof that the phase is nanostructured, since emulsions and other common liquids are never bicontinuous. This issue has been addressed in "On the demonstration of bicontinuous structures in microemulsions." Lindman. B., Shinoda, K., Olsson, U., Anderson, D. M., Karlstrom, G. and Wennerstrom, H. (1989) Colloids and Surfaces 38:205. The time-tested way to demonstrate bicontinuity is to use pulsed-gradient NMR and measure the effective self-diffusion coefficients of both oil and water separately; generally it is best to measure also the self-diffusion of the surfactant. Electrical conductivity can also be used to establish water continuity, although this is prone to problems associated with "hopping" processes. Fluoresence quenching has also been used for continuity determination. Sanchez-Rubio, M., Santos-Vidals, L. M., Rushforth, D. S. and Puig, J. E. (1985) J. Phys. Chem. 89:411. Small-angle neutron and x-ray scattering analyses have been used to examine bicontinuity. Auvray, L., Cotton, L R., Ober, R. and Taupin. J. (1984) J. Phys. Chem. 88:4586. Porod analysis of SAXS curves has been used to deduce the presence of interfaces, thus proving that a nanostructure is present. Martino, A. and Kaler, E. W. (1990) J. Phys. Chem. 94:1627. Freeze-fracture electron microscopy, with extremely fast rates of freezing, has been used to study microemulsions and is the result of decades of development on fixation methods for nanostructured liquids: a critical review discussing the methods and the reliability of the results has been given. Talmon, Y. in K. L. Mirtal and P. Bothorel (Eds), Vol. 6. Plenum Press, New York, 1986, p. 1581.

In the event that an oil-water-surfactant liquid phase is not clearly an L1 or L2 phase, and does not show strong evidence of bicontinuity, then the analysis to demonstrate that it is nanostructured can be fairly involved and no single technique will suffice. In general, one would apply the measurements discussed in this section, such as SANS or SAXS. NMR self-diffusion, cryo EM, etc., to attempt to rationalize the data within the context of a model nanostrucrure.

L3 phase: L2-phase regions in phase diagrams sometimes exhibit "tongues" sticking out of them: long, thin protrusions unlike the normal appearance of a simple L2 phase region. This sometimes appears also with some L1 regions, as described below. When one examines these closely, especially with X-ray and neutron scattering, they differ in a fundamental way from L2 phases. In an L2 phase, the surfactant film is generally in the form of a monolayer with oil (apolar solvent) on one side and water (polar solvent) on the other. By contrast, in this "L3 phase" as these phases are called, the surfactant is in the form of a bilayer with water (polar solvent) on both sides. The L3 phase is generally considered to be bicontinuous and, in fact, it shares another property with cubic phases: there are two distinct aqueous networks interwoven but separated by the bilayer. So, the L3 phase is really very similar to the cubic phase but lacking the long-range order of the cubic phase. L3 phases stemming from L2 phases and those stemming from L1 phases are given different names. "L3 phase" is used for those associated to L2 phases, and "L3 * phase" for those associated to L1 phases.

Determination of the nanostructured L3 phase. Determination of the L3 phase in distinction to the other liquid phases discussed herein can be a sophisticated problem, requiring the combination of several analyses. The most important of these techniques are now discussed. In spite of its optical isotropy when acquiescent and the fact that it is a liquid, the L3 phase can have the interesting property that it can exhibit flow birefringence. Often this is associated with fairly high viscosity, viscosity that can be considerably higher than that observed in the L1 and L2 phases, and comparable to or higher than that in the lamellar phase. These properties are of course a result of the continuous bilayer film, which places large constraints on the topology and the geometry of the nanostructure. Thus, shear can result in the cooperative deformation (and resulting alignment) of large portions of the bilayer film, in contrast with, for.example, a micellar L1 phase where independent micellar units can simply displace with shear, and in any case a monolayer is generally much more deformable under shear than a bilayer. Support for this interpretation comes from the fact that the viscosity of L3 phases is typically a linear function of the volume fraction of surfactant. Snabre. P. and Porte. G. (1990) Europhys. Len. 13:641.

Sophisticated light, neutron, and x-ray scattering methodologies have been developed for determination of nanostructured L3 phases. Safinya, C. R., Roux, D., Smith,. G. S., Sinha, S. K., Dimon, P., Clark, N. A. and Bellocq, A. M. (1986) Phys. Rev. Lett. 57:2718; Roux, D. and Safinya, C. R. (1988) J. Phys. France 49:307; Nallet, F., Roux, D. and Prost, J. (1989) J. Phys. France 50:3147. The analysis of Roux, et al. in Roux, D., Cates, M. E., Olsson, U., Ball, R. C., Nallet, F. and Bellocq, A. M., Europhys. Lett. purportedly is able to determine that the nanostructure has two aqueous networks, separated by the surfactant bilayer, which gives rise to a certain symmetry due to the equivalence of the two networks.

Fortunately, determination of the nanostructured nature of an L3 phase based on phase behavior can be more secure than in the case of typical L1, L2, or even microemulsion phases. This is first of all because the L3 phase is often obtained by addition of a small amount (a few percent) of oil or other compound to a lamellar or bicontinuous cubic phase, or small increase of temperature to these same phases. Since these liquid crystalline phases are easy to demonstrate to be nanostructured (Bragg peaks in X-ray, in particular), one can be confident that the liquid phase is also nanostructured when it is so close in composition to a liquid crystalline phase. After all, it would be extremely unlikely that the addition of a few percent of oil to a nanostructured liquid crystalline phase would convert the liquid crystal to a structureless liquid. Indeed, pulsed-gradient NMR self-diffusion measurements in the Aerosol OT—brine system show that the self-diffusion behavior in the L3 phase extrapolates very clearly to those in the nearby reversed bicontinuous cubic phase. This same L3 phase has been the subject of a combined SANS, self-diffusion, and freeze-fracture-electron microscopy study. Strey, R., Jahn,. W., Skouri, M., Porte, G., Marisman,. J. and Olsson,. U. in "Structure and Dynamics of Supramolecular Aggregates—S. H. Chen, J. S. Huang and P. Tartaglia, Eds., Kluwer Academic Publishers,. The Netherlands. Indeed, in SANS and SAXS scattering analysis of L3 phases, a broad interference peak is often observed at wave vectors that correspond to d-spacings that are the same order of magnitude as those in bicontinuous cubic phases that are nearby in the phase diagram, and the author has developed a model for L3 phase nanostructure which is an extrapolation of known structures for bicontinuous cubic phases. Anderson, D. M., Wennerstrom, H. and Olsson, U. (1989) J. Phys. Chem. 93:4532.

The Nanostructured Liquid Crystalline Phases of Utility

As a component of the coated particle the nanostructured liquid crystalline phase material may be
a. a nanostructured normal or reversed cubic phase material,
b. a nanostructured normal or reversed hexagonal phase material,
c. a nanostructured normal or reversed intermediate phase material or
d. a nanostructured lamellar phase material.

The nanostructured liquid crystalline phases are characterized by domain structures composed of domains of at least a first type and a second type (and in some cases three or even more types of domains) having the following properties:

a) the chemical moieties in the first type domains are incompatible with those in the second type domains (and in general, each pair of different domain types are mutually incompatible) such that they do not mix under the given conditions but rather remain as separate domains (for example, the first type domains could be composed substantially of polar moieties such as water and lipid head groups, while the second type domains could be composed substantially of apolar moieties such as hydrocarbon chains: or, first type domains could be polystyrene-rich, while second type domains are polyisoprene-rich, and third type domains are polyvinylpyrrolidone-rich);

b) the atomic ordering within each domain is liquid-like rather than solid-like, lacking lattice-ordering of the atoms; (this would be evidenced by an absence of sharp Bragg peak-reflections in wide-angle x-ray diffraction);

c) the smallest dimension (e.g., thickness in the case of layers, diameter in the case of cylinders or spheres) of substantially all domains is in the range of nanometers (viz., from about 1 to about 100 nm); and d) the organization of the domains conforms to a lattice, which may be one-, two-, or three-dimensional and which has a lattice parameter (or unit cell size) in the nanometer range (viz., from about 5 to about 200 nm), the organization of domains thus conforms to one of the 230 space groups tabulated in the International Tables of Crystallography and would be evidenced in a well-designed small-angle x-ray scattering (SAXS) measurement by the presence of sharp Bragg reflections with d-spacings of the lowest order reflections being in the range of 3–200 nm.

In the discussion of the identification of these liquid crystalline phases using deuterium NMR or self-diffusion measurements, it is assumed that the liquid crystal is not polymerized. In the cases where it is polymerized, these measurements will be strongly affected by the polymerization and may not conform to the same rules that apply for unpolymerized liquid crystals. In particular, the self-diffusion coefficients of surfactants can be dramatically reduced, as was reported by the present author in Strom, P. and Anderson, D. M. (1992) Langmuir 8:691. NMR spectra for polymerized cubic phases were calculated for certain conditions by the present author in Anderson, D. M. (1990) Supplement to J. de Phys. C7-1.

Lamellar phase: The lamellar phase is characterized by:
1. Small-angle x-ray shows peaks indexing as 1:2:3:4:5 . . . in wave number.
2. To the unaided eye, the phase is either transparent or exhibits mild or moderate turbidity.

3. In the polarizing optical microscope, the phase is birefringent, and the well-known textures have been well described by Rosevear and by Winsor (e.g., Chem. Rev. 1968, p. 1). The three most pronounced textures are the "Maltese crosses", the "mosaic" pattern, and the "oily streaks" patterns. The Maltese cross is a superposition of two dark bands (interference fringes) roughly perpendicular to each other, over a roughly circular patch of light (birefringence), forming a distinctive pattern reminiscent of the WWI German military symbol. The variations on this texture, as well as its source, is thoroughly described in J. Bellare, Ph.D. Thesis, Univ. of Minnesota, 1987. The "mosaic" texture can be envisioned as the result of tightly packing together a dense array of deformed Maltese crosses, yielding dark and bright patches randomly quilted together. The "oily streaks" pattern is typically seen when the (low viscosity) lamellar phase flows between glass and coverslip; in this pattern, long curved lines are seen, upon close inspection under magnification 400x), to be composed of tiny striations which run roughly perpendicular to the line of the curve, as ties make up a railroad track (to be contrasted with the hexagonal texture discussion below). In some cases, particularly if the phase is massaged gently between glass and coverslip for a period of time, the lamellar phase will align with its optic axis parallel to the line of sight in the microscope, resulting in a disappearance of the birefringence.

For lamellar phases in surfactant-water systems:
1. Viscosity is low enough so that the material flows (e.g. when a tube containing the phase is tipped upside down),
2. The self-diffusion rates of all components are high comparable to their values in bulk—e.g., the effective self-diffusion coefficient of water in the lamellar phase is comparable to that in pure water. Since the surfactants that form liquid crystals are usually not liquid at ambient temperatures, the reference point for the self-diffusion coefficient of the surfactant is not clear-cut; and, in fact, the effective (measured) self-diffusion coefficient of the surfactant in the lamellar phase is often taken to be the reference point for interpreting measurements in other phases.
3. If the surfactant is deuterated in the head group, and the $^2$H NMR bandshape measured, one finds two spikes with the splitting between them twice what it is in the hexagonal phase.
4. In terms of phase behavior, the lamellar phase generally occurs at high surfactant concentrations in single-tailed surfactant/water systems, typically above 70% surfactant: in double-tailed surfactants, it often occurs at lower concentrations, often extending well below 50%. It generally extends to considerably higher temperatures than do any other liquid crystalline phases that happen to occur in the phase diagram.

For lamellar phases in single-component block copolymer systems:
1. Shear modulus is generally lower than other liquid crystalline phases in the same system.
2. In terms of phase behavior, the lamellar phase generally occurs at volume fractions of the two blocks is roughly 50:50.

Normal hexagonal phase: The normal hexagonal phase is characterized by:
1. Small-angle x-ray shows peaks indexing as $1:\sqrt{3}:2:\sqrt{7}:3\ldots$ in general, $\sqrt{(h^2+hk-k^2)}$, where h and k are integers—the Miller indices of the two-dimensional symmetry group,
2. To the unaided eye, the phase generally transparent when fully equilibrated, and thus often considerably clearer than any nearby lamellar phase.
3. In the polarizing optical microscope, the phase is birefringent, and the well-known textures have been well described by Rosevear and by Winsor (e.g., Chem. Rev. 1968, p. 1). The most distinctive of these is the "fan-like" texture. This texture appears to be made up of patches of birefringence, where within a given patch fine striations fan out giving an appearance reminiscent of an oriental fan. Fan directions in adjacent patches are randomly oriented with respect to each other. A key difference distinguishing between lamellar and hexagonal patterns is that the striations in the hexagonal phase do not, upon close examination at high magnification, prove to be composed of finer striations running perpendicular to the direction of the larger striation, as they do in the lamellar phase.

For normal hexagonal phases in surfactant-water systems:
1. Viscosity is moderate, more viscous than the lamellar phase but far less viscous than typical cubic phases (which have viscosities in the millions of centipoise).
2. The self-diffusion coefficient of the surfactant is slow compared to that in the lamellar phase: that of water is comparable to that in bulk water.
3. The $^2$H NMR bandshape using deuterated surfactant shows a splitting, which is one-half the splitting observed for the lamellar phase.
4. In terms of phase behavior, the normal hexagonal phase generally occurs at moderate surfactant concentrations in single-tailed surfactant water systems, typically on the order of 50% surfactant. Usually the normal hexagonal phase region is adjacent to the micellar (L1) phase region, although non-bicontinuous cubic phases can sometimes occur in between. In double-tailed surfactants, it generally does not occur at all in the binary surfactant-water system.

For hexagonal phases in single-component block copolymer systems, the terms "normal" and "reversed" do not generally apply (although in the case where one block is polar and the other apolar, these qualifiers could be applied in principle). The shear modulus in such a hexagonal phase is generally higher than a lamellar phase and lower a bicontinuous cubic phase, in the same system. In terms of phase behavior, the hexagonal phases generally occurs at volume fractions of the two blocks on the order of 35:65. Typically, two hexagonal phases will straddle the lamellar phase with, in each case, the minority component being inside the cylinders (this description replacing the 'normal/reversed' nomenclature of surfactant systems).

Reversed hexagonal phase: In surfactant-water systems, the identification of the reversed hexagonal phase differs from the above identification of the normal hexagonal phase in only two respects:
1. The viscosity of the reversed hexagonal phase is generally quite high, higher than a typical normal hexagonal phase, and approaching that of a reversed cubic phase. And,
2. In terms of phase behavior, the reversed hexagonal phase generally occurs at high surfactant concentrations in double-tailed surfactant/water systems, often extending to, or close to, 100% surfactant. Usually the reversed hexagonal phase region is adjacent to the lamellar phase region which occurs at lower surfactant concentration, although bicontinuous reversed cubic phases often occur in between. The reversed hexagonal phase does appear, somewhat surprisingly, in a number of binary systems with single-tailed surfactants, such as those of many monoglycerides (include glycerol monooleate), and a number of nonionic PEG-based surfactants with low HLB.

As stated above in the discussion of normal hexagonal phases, the distinction between normal and 'reversed' hexagonal phases makes sense only in surfactant systems, and generally not in single-component block copolymer hexagonal phases.

Normal bicontinuous cubic phase: The normal bicontinuous cubic phase is characterized by:

1. Small-angle x-ray shows peaks indexing to a three-dimensional space group with a cubic aspect. The most commonly encountered space groups, along with their indexings are: 1a3d (#230), with indexing $\sqrt{6}:\sqrt{8}:\sqrt{14}:4$ . . . Pn3m (#224), with indexing $\sqrt{2}:\sqrt{3}:2:\sqrt{6}:\sqrt{8}:$ and 1m3m (#229), with indexing $\sqrt{2}:\sqrt{4}:\sqrt{6}:\sqrt{8}:\sqrt{10}$ . . .
2. To the unaided eye, the phase is generally transparent when fully equilibrated, and thus often considerably clearer than any nearby lamellar phase.
3. In the polarizing optical microscope, the phase is non-birefringent, and therefore there are no optical textures.

For normal bicontinuous cubic phases in surfactant-water systems:

1. Viscosity is high, much more viscous than the lamellar phase and even more viscous than typical normal hexagonal phases. Most cubic phase have viscosities in the millions of centipoise.
2. No splitting is observed in the NMR bandshape, only a single peak, corresponding to isotropic motion.
3. In terms of phase behavior, the normal bicontinuous cubic phase generally occurs at fairly high surfactant concentrations in single-tailed surfactant/water systems typically on the order of 70% surfactant with ionic surfactants. Usually the normal bicontinuous cubic phase region is between lamellar and normal hexagonal phase regions, which along with its high viscosity and non-birefringence make its determination fairly simple. In double-tailed surfactants, it generally does not occur at all in the binary surfactant-water system.

For bicontinuous cubic phases in single-component block copolymer systems, the terms "normal" and "reversed" do not generally apply (although in the case where one block is polar and the other apolar, these qualifiers could be applied in principle). The shear modulus in such a bicontinuous cubic phase is generally much higher than a lamellar phase, and significantly than a hexagonal phase in the same system. In terms of phase behavior, the bicontinuous cubic phases generally occur at volume fractions of the two blocks on the order of 26:74. In some cases, two bicontinuous cubic phases will straddle the lamellar phase with, in each case, the minority component being inside the cylinders (this description replacing the 'normal/reversed' nomenclature of surfactant systems), and hexagonal phases straddling the cubic-lamellar-cubic progression.

Reversed bicontinuous cubic phase.—The reversed bicontinuous cubic phase is characterized by:

In surfactant-water systems, the identification of the reversed bicontinuous cubic phase differs from the above identification of the normal bicontinuous cubic phase in only one respect. In terms of phase behavior, the reversed bicontinuous cubic phase is found between the lamellar phase and the reversed hexagonal phase, whereas the normal is found between the lamellar and normal hexagonal phases: one must therefore make reference to the discussion above for distinguishing normal hexagonal from reversed hexagonal. A good rule is that if the cubic phase lies to higher water concentrations than the lamellar phase, then it is normal, whereas if it lies to higher surfactant concentrations than the lamellar then it is reversed. The reversed cubic phase generally occurs at high surfactant concentrations in double-tailed surfactant/water systems, although this is often complicated by the fact that the reversed cubic phase may only be found in the presence of added hydrophobe ("oil") or amphiphile. The reversed bicontinuous cubic phase does appear in a number of binary systems with single-tailed surfactants such as those of many monoglycerides (include glycerol monooleate) and a number of nonionic PEG-based surfactants with low HLB.

It should also be noted that in reversed bicontinuous cubic phases, though not in normal, the space group #212 has been observed. This phase is derived from that of space group #230. As stated above in the discussion of normal bicontinuous cubic phases, the distinction between 'normal' and 'reversed' bicontinuous cubic phases makes sense only in surfactant systems, and generally not in single-component block copolymer bicontinuous cubic phases.

Normal discrete (non-bicontinuous) cubic phase: The normal non-bicontinuous cubic phase is characterized by:

1. Small-angle x-ray shows peaks indexing to a three-dimensional space group with a cubic aspect. The most commonly encountered space group in surfactant systems is Pm3n (#223) with indexing $\sqrt{2}:\sqrt{4}:\sqrt{5}:$ . . . In single-component block copolymers, the commonly observed space group is Im3m, corresponding to body-centered sphere-packings with indexing $\sqrt{2}:\sqrt{4}:\sqrt{6}:\sqrt{8}:$ . . .
2. To the unaided eye, the phase is generally transparent when fully equilibrated, and thus often considerably clearer than any associated lamellar phase.
3. In the polarizing optical microscope, the phase is non-birefringent and therefore there are no optical textures.

For normal discrete cubic phases in surfactant-water systems:

1. Viscosity is high, much more viscous than the lamellar phase and even more viscous than typical normal hexagonal phases. Most cubic phase have viscosities in the millions of centipoise, whether discrete or bicontinuous.
2. Also in common with the bicontinuous cubic phases, there is no splitting in the NMR bandshape, only a single isotropic peak.
3. In terms of phase behavior, the normal discrete cubic phase generally occurs at fairly low surfactant concentrations in single-tailed surfactant water systems, typically on the order of 40% surfactant with ionic surfactants. Usually the normal discrete cubic phase region is between normal micellar and normal hexagonal phase regions, which along with its high viscosity and non-birefringence make its determination fairly simple. In double-tailed surfactants, it generally does not occur at all in the binary surfactant-water system. For discrete cubic phases in single-component block copolymer systems, the terms "normal" and "reversed" do not generally apply (although in the case where one block is polar and the other apolar, these qualifiers could be applied in principle). The shear modulus in such a discrete cubic phase is generally dependent almost entirely on the shear modulus of the polymer that forms the blocks in the continuous phase. In terms of phase behavior, the discrete cubic phases generally occur at very low volume fractions of one or other of the two blocks, on the order of 20% or less.

Reversed discrete cubic phase: The reversed discrete cubic phase is characterized by:

In surfactant-water systems, the identification of the reversed discrete cubic phase differs from the above identification of the normal discrete cubic phase in three respects:

1. In terms of phase behavior, the reversed discrete cubic phase is found between the lamellar phase and the reversed hexagonal phase, whereas the normal is found between the lamellar and normal hexagonal phases: one must therefore make reference to the discussion above for distinguishing normal hexagonal from reversed hexagonal. A good rule is that if the cubic phase lies to higher water concentrations than the lamellar phase, then it is normal, whereas if it lies to higher surfactant concentrations than the lamellar then it is reversed. The reversed cubic phase generally occurs at high surfactant concentrations in double-tailed surfactant/water systems, although this is often complicated by the fact that the reversed cubic phase may only be found in the presence of added hydrophobe ('oil') or amphiphile. The reversed discrete cubic phase does appear in a number of binary systems with single-tailed surfactants, such as those of many monoglycerides (include glycerol monooleate), and a number of nonionic PEG-based surfactants with low HLB.
2. The space group observed is usually Fd3m. #227.
3. The self-diffusion of the water is very low, while that of any hydrophobe present is high; that of the surfactant is generally fairly high, comparable to that in the lamellar phase. As stated above in the discussion of normal discrete cubic phases, the distinction between 'normal' and 'reversed' discrete cubic phases makes sense only in surfactant systems, and generally not in single-component block copolymer discrete cubic phases.

Intermediate phases: The intermediate phase is characterized by:

These phases occur quite rarely, and when they are found they generally occupy very narrow regions in the phase diagram. Presently the structures of many of these are unknown or under debate. The intermediate phases can be classified as follows:

Normal int(1) phases occur at lower surfactant concentration than the normal bicontinuous cubic phase, adjacent to the hexagonal phase. Viscosity is generally low or moderately low, no higher than that of the normal hexagonal phase. The phase is birefringent, with textures typically similar to those of the hexagonal phase. Self-diffusion of the components is very similar to those in the hexagonal phase. Small-angle x-ray shows a lower-symmetry space group than the cubic phases, typically monoclinic. Fairly sophisticated NMR bandshape and SAXS analyses can be used to distinguish this phase from the normal hexagonal phase. See Henriksson, U., Blackmore, E. S., Tiddy, G. J. T. and Soderman, O. (1992) J. Phys. Chem. 96:3894. Typically bandshape splittings will be intermediate between those of hexagonal and the zero splitting of the isotropic phase, which provides good evidence of an intermediate phase.

Normal int(2) is found at higher concentrations than the normal bicontinuous cubic phase, adjacent to the lamellar phase. These bear close resemblance, both in terms of property and probably also in terms of structure, to the normal bicontinuous cubic phases, except that they are birefringent and show differences in NMR bandshape and SAXS analyses. Optical textures are somewhat unusual, in some cases resembling lamellar textures and in some resembling hexagonal, but these can be considerably coarser than either of the more common phases. As in the int(1) phases, the space group is of lower symmetry, typically rhombohedral or tetragonal, requiring two unit cell parameters for characterization and making SAXS analysis difficult. In general, if the squares of the d-spacing ratios cannot be fit to a simple integral scheme, then an intermediate phase structure is suspect.

Reversed int(2) is found at lower concentrations than the reversed bicontinuous cubic phase, adjacent to the lamellar phase. These are birefringent and show unusual in NMR bandshape and SAXS analyses. As in the int(1) and int(2) phases, the space group is of lower symmetry, typically rhombohedral or tetragonal, requiring two unit cell parameters for characterization and making SAXS analysis difficult. SAXS analysis difficult, though the presence of Bragg peaks in the SAXS spectrum which do not index to a cubic or hexagonal lattice (which have only one lattice parameter) is, together with optical birefringence, indication of an intermediate phase. Space groups which are likely for bicontinuous intermediate phases have been discussed in a publication by the present author. D. M. Anderson, Supplement to J. Physique, Proceedings of Workshop on Geometry, and Interfaces, Aussois, France, September 1990. C7-1–C7-18.

At the time that the coated particle 10 is being formed and the exterior coating 20 is not yet formed, it is highly desirable that the nanostructured liquid phase material or the nanostructured liquid crystalline phase material or the combination be one that is in equilibrium with water (polar solvent) or, more precisely, with a dilute aqueous solution. Once the coated particle 10 has its exterior coating 20, the foregoing nanostructured material need not be one that is in equilibrium with water. The liquid phases that can be in equilibrium with water are:

L2 phase (a.k.a. reversed micelles), microemulsion, and

L3 phase (but not the L3* phase).

These supplement the liquid crystalline phases that can be in equilibrium with water:

reversed cubic phase, reversed hexagonal phase, reversed intermediate phase, and lamellar phase.

The phases that can be in equilibrium with water are preferred from the point of view of making coated particles of the present invention. Preferably, in using the process described herein to disperse a given phase as the matrix, it is desirable that the phase be insoluble in water, or whatever solvent the particles are dispersed in. Furthermore, when the interior phase has the additional property that it is in equilibrium with excess aqueous solution during formation of the particles, then concerns of phase transformation are minimized. Similarly when the interior phase is in equilibrium with excess aqueous solution under the conditions encountered when and after the particle coating is released, then the concerns of phase changes are likewise minimized, and in some applications this may be advantageous.

Whereas insolubility in water (external solvent, in general) is preferred for the matrix at the instant of particle formation, and frequently also at the time of application, there are applications where solubility in water at the time of application is advantageous, and this can be accomplished with the instant invention. For example, consider a matrix composed of 20% C12E5 (pentaethylene glycol dodecyl ether) in water. At 75° C., this composition produces an L3 phase which is in equilibrium with excess water (dilute solution) and thus this composition would be readily dispersible at 75° C. If the application temperature were between 0 and 25° C., however, then this interior composition would be soluble in water, and in fact the C12E5 acts as an ordinary water-soluble surfactant at room temperature. This could be advantageous if a non greasy, non-comedogenic—and even cleansing—final product is desired after release of the particle coating.

The nanostructured liquid phase material may be formed from:
a. a polar solvent and a surfactant or
b. a polar solvent, a surfactant and an amphiphile or hydrophobe or
c. a block copolymer or
d. a block copolymer and a solvent.

The nanostructured liquid crystalline phase material may be formed from:
a. a polar solvent and a surfactant.
b. a polar solvent, a surfactant and an amphiphile or hydrophobe, or
c. a block copolymer or
d. a block copolymer and a solvent.

Above under the heading Chemical Criteria, criteria were discussed which could be used to select operative polar and apolar groups in order to make an operative surfactant. Thus, suitable surfactants include those compounds which contain two chemical moieties, one being an operative polar group chosen from those described in that discussion of polar groups, and the other being an operative apolar group chosen from those described in that discussion of apolar groups. Surfactants of Utility.

Suitable surfactants or block copolymer components (or mixtures thereof) may include: a. cationic surfactant
b. anionic surfactant
c. semipolar surfactant
d. zwitterionic surfactant
  i. in particular, a phospholipid
  ii. a lipid mixture containing phospholipids, designed to match the physico-chemical characteristics of a biomembrane
e. monoglyceride
f. PEGylated surfactant
g. one of the above but with aromatic ring
h. block copolymer
  i. with both blocks hydrophobic, but mutually immiscible
  ii. with both blocks hydrophilic, but mutually immiscible,
  iii. with one block hydrophilic and the other hydrophobic, i.e., amphiphilic)
i. a mixture of two or more of the above.

Suitable lipids include phospholipids (such as phosphatidylcholine, phosphatidylserine, phosphatidylethanolamine, or sphingomyelin), or glycolipids (such as MGDG, diacylglucopyranosyl glycerols, and Lipid A). Other suitable lipids are phospholipids (including phosphatidylcholines, phosphatidylinositols, phosphatidylglycerols, phosphatidic acids, phosphatidylserines, phosphatidylethanolamines, etc.), sphingolipids (including sphingomyelins), glycolipids (such as galactolipids such as MGDG and DGDG, diacylglucopyranosyl glycerols, and Lipid A), salts of cholic acids and related acids such as deoxycholic acid, glycocholic acid, taurocholic acid, etc., gentiobiosyls, isoprenoids, ceramides, plasmologens, cerebrosides (including sulphatides), gangliosides, cyclopentatriol lipids, dimethylaminopropane lipids, and lysolecithins and other lysolipids which are derived from the above by removal of one acyl chain.

Other suitable types of surfactants include anionic, cationic, zwittenionic, semipolar, PEGylated, amine oxide and aminolipids. Preferred surfactants are:

anionic—sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps of the form $IC_n$, where the chain length n is between 8 and 20 and I is a monovalent counterion such as lithium, sodium, potassium, rubidium, etc., cationic—dimethylammonium and trimethylammonium surfactants of chain length from 8 to 20 and with chloride, bromide or sulfate counterion, myristyl-gammapicolinium chloride and relatives with alkyl chain lengths from 8 to 18, benzalkonium benzoate, double-tailed quaternary ammonium surfactants with chain lengths between 8 and 18 carbons and bromide, chloride or sulfate counterions, nonionic PEGylated surfactants of the form $C_nE_m$ where the alkane chain length n is from 6 to 20 carbons and the average number of ethylene oxide groups m is from 2 to 80, ethoxylated cholesterol;

zwitterionics and semipolars—N,N,N-trimethylaminodecanoimide, amine oxide surfactants with alkyl chain length from 8 to 18 carbons; dodecyldimethylammoniopropane-1-sulfate, dodecyldimethylammoniobutyrate, dodecyltrimethylene di(ammonium chloride); decylmethylsulfonediimine; dimethyleicosylammoniohexanoate and relatives of these zwitterionics and semipolars with alkyl chain lengths from 8 to 20.

Preferred surfactants which are FDA-approved as injectables include benzalkonium chloride, sodium deoxycholate, myristyl-gamma-picolinium chloride, Poloxamer 188, polyoxyl castor oil and related PEGylated castor oil derivatives such as Cremophor EL, Arlatone G, sorbitan monopalmitate, Pluronic 123, and sodium 2-ethylhexanoic acid. Other low-toxicity surfactants and lipids, which are of at least relatively low solubility in water, that are preferred for the present invention for products intended for a number of routes of administration, include: acetylated monoglycerides, aluminum monostearate, ascorbyl palmitate free acid and divalent salts, calcium stearoyl lactylate, ceteth-2, choleth, deoxycholic acid and divalent salts, dimethyldioctadecylammonium bentonite, docusate calcium, glyceryl stearate, stearamidoethyl diethylamine, ammoniated glycyrrhizin, lanolin nonionic derivatives, lauric myristic diethanolamide, magnesium stearate, methyl gluceth-120 dioleate, monoglyceride citrate, octoxynol-1, oleth-2, oleth-5, peg vegetable oil, peglicol-5-oleate, pegoxol 7 stearate, poloxamer 331, polyglyceryl-10 tetralinoleate, polyoxyethylene fatty acid esters, polyoxyl castor oil, polyoxyl distearate, polyoxyl glyceryl stearate, polyoxyl lanolin, polyoxyl-8 stearate, polyoxyl 150 distearate, polyoxyl 2 stearate, polyoxyl 35 castor oil, polyoxyl 8 stearate, polyoxy160 castor oil, polyoxyl 75 lanolin, polysorbate 85, sodium stearoyl lactylate, sorbitan sesquioleate, sorbitan trioleate, stear-o-wet c, stear-o-wet m, stearalkonium chloride, stearamidoethyl diethylamine (vaginal), steareth-2, steareth-10, stearic acid, stearyl citrate, sodium stearyl fumarate or divalent salt, trideceth 10, trilaneth-4 phosphate, Detaine PB, JBR-99 rhamnolipid (from Jeneil Biosurfactant), glycocholic acid and its salts, taurochenodeoxycholic acid (particularly combined with vitamin E), tocopheryl dimethylaminoacetate hydrochloride, tocopheryl phosphonate, tocopheryl peg 1000 succinate, cytofectin gs, 1,2-dioleoyl-sn-glycero-3-trimethylammonium-propane, cholesterol linked to lysinamide or ornithinamide, dimethyldioctadecyl ammonium bromide, 1,2-dioleoyl-sn-3-ethylphosphocholine and other double-chained lipids with a cationic charge carried by a phosphorus or arsenic atom, trimethyl aminoethane carbamoyl cholesterol iodide, lipoic acid, O,O'-ditetradecanoyl-N-(alpha-trimethyl ammonioacetyl) diethanolamine chloride (DC-6-14), N-[(1-(2,3-dioleyloxy)propyl)]-N-N-N-trimethylammonium chloride, N-methyl-4-(dioleyl)methylpyridinium chloride (saint-2), lipidic glycosides with amino alkyl pendent groups, 1,2-dimyristyloxypropyl-3-dimethylhydroxyethyl ammonium bromide, bis[2-(11-phenoxyundecanoate)ethyl]-dimethylammonium bromide, N-hexadecyl-N-10-[O-(4-acetoxy)-phenylundecanoate]ethyl-dimethylammonium bromide, bis[2-(11-butyloxyundecanoate)ethyl] dimethylammonium bromide, 3-beta-[N-(N',N'-dimethylaminoethane)-carbamoyl]cholesterol, vaxfectin, cardiolipin, dodecyl-N,N-dimethylglycine, and lung surfactant (Exosurf, Survanta).

Suitable block copolymers are those composed of two or more mutually immiscible blocks from the following classes of polymers: polydienes, polyallenes, polyacrylics and polymethacrylics (including polyacrylic acids, polymethacrylic acids, polyacrylates, polymethacrylates, polydisubstituted esters, polyacrylamides, polymethacrylamides, etc.), polyvinyl ethers, polyvinyl alcohols, polyacetals, polyvinyl ketones, polyvinylhalides, polyvinyl nitriles, polyvinyl esters, polystyrenes, polyphenylenes, polyoxides, polycarbonates, polyesters, polyanhydrides, polyurethanes, polysulfonates, polysiloxane, polysulfides, polysulfones, polyamides, polyhydrazides, polyureas, polycarbodiimides, polyphosphazenes, polysilanes, polysilazanes, polybenzoxazoles, polyoxadiazoles, polyoxadiazoiidines, polythiazoles, polybenzothiazoles, polypyromellitimides, polyquinoxalines, polybenzimidazoles, polypiperazines, cellulose derivatives, alginic acid and its salts, chitin, chitosan, glycogen, heparin, pectin, polyphosphorus nitrile chloride, polytri-n-butyl tin fluoride, polyphosphoryldimethylamide, poly-2,5-selenienylene, poly-4-n-butylpyridinium bromide, poly-2-N-methylpyridinium iodide, polyallylammonium chloride, and polysodium-sulfonate-trimethylene oxyethylene. Preferred polymer blocks are polyethylene oxide, polypropylene oxide, polybutadiene, polyisoprene, polychlorobutadiene, polyacetylene, polyacrylic acid and its salts, polymethacrylic acid and its salts, polyitaconic acid and its salts, polymethylacrylate, polvethylacrylate, polybutylacrylate, polymethylmethacrylate, polypropylmethacrylate, poly-N-vinyl carbazole, polyacrylamide, polyisopropylacrylamide, polymethacrylamide, polyacrylonitrile, polyvinyl acetate, polyvinyl caprylate, polystyrene, poly-alpha-methylstyrene, polystyrene sulfonic acid and its salts, polybromostyrene, polybutyleneoxide, polyacrolein, polydimethylsiloxane, polyvinyl pyridine, polyvinyl pyrrolidone, polyoxytetramethylene, polydimethylfulvene, polymethylphenylsiloxane, polycyclopentadienylene vinylene, polyalkylthiophene, polyalkyl-p-phenylene, polyethylene-altpropylene, polynorbornene, poly-5-((trimethylsiloxy) methyl)norbornene, polythiophenylene, heparin, pectin, chitin, chitosan, and alginic acid and its salts. Especially preferred block copolymers are polystyrene-b-butadiene, polystyrene-b-isoprene, polystyrene-b-styrenesulfonic acid, polyethyleneoxide-b-propyleneoxide, polystyrene-b-dimethylsiloxane, polyethyleneoxide-b-styrene, polynorborene-b-5-((trimethylsiloxy)methyl)norbornene, polyacetylene-b-5((trimethylsiloxv)methyl)norbornene, polyacetylene-b-norbornene, polyethyleneoxide-b-norbornene, polybutyleneoxide-b-ethyleneoxide, polyethyleneoxide-b-siloxane, and the triblock copolymer polyisoprene-b-styrene-b-2-vinylpyridine.

Third Component: Hydrophobe or Non-surfactant Amphiphile.

This component can serve multiple functions in a matrix of the present invention, including modulation of phase behavior, tuning of poresize, solubilization of an active, modulation of release properties, etc. Choices appropriate for this invention include:

a. alkane or alkene, other long-chain aliphatic compound b. aromatic compound, such as toluene c. long-chain alcohol d. a glyceride (diglyceride or triglyceride)

e. an acylated sorbitan, such as a sorbitan triester (e.g., sorbitan trioleate), or sesquioleate, or mixture of sorbitans with different numbers of acyl chains between 2 and 6 f. other hydrophobe or non-surfactant amphiphile or mixture with one or more of the above, g. none.

Suitable third components (hydrophobes or non-surfactant amphiphiles), include: n-alkane, where n is from 6 to 20, including branched, unsaturated, and substituted variants (alkenes, chloroalkanes, etc.), cholesterol and related compounds, terpenes, diterpenes, triterpenes, fatty alcohols, fatty acids, aromatics, cyclohexanes, bicyclics such as naphthalenes and naphthol, quinolines and benzoquinolines, etc., tricyclics such as carbazole, phenothiazine, etc., pigments, chlorophyll, sterols, triglycerides, sucrose fatty acid esters (such as Olestra™), natural oil extracts (such as clove oil, anise oil, cinnamon oil, coriander oil, eucalyptus oil, peppermint oil), wax, bilirubin, bromine, iodine, hydrophobic and amphiphilic proteins and polypeptides (including gramicidin, casein, receptor proteins, lipid-anchored proteins, etc.), local anesthetics (such as butacaine, ecgonine, procaine, etc.), and low-molecular weight hydrophobic polymers (see listing of polymers above). Especially preferred third components are: anise oil, clove oil, coriander oil, cinnamon oil, eucalyptus oil, peppermint oil, beeswax, benzoin, benzyl alcohol, benzyl benzoate, naphthol, capsaicin, cetearyl alcohol, cetyl alcohol, cinnamaldehyde, cocoa butter, coconut oil, cottonseed oil (hydrogenated), cyclohexane, cyclomethicone, dibutyl phthalate, dibutyl sebacate, diocryl phthalate, DIPAC, ethyl phthalate, ethyl vanillin, eugenol, fumaric acid, glyceryl distearate, menthol, methyl acrylate, methyl salicylate, myristyl alcohol, oleic acid, oleyl alcohol, benzyl chloride, paraffin, peanut oil, piperonal, rapeseed oil, rosin, sesame oil, sorbitan fatty acid esters, squalane, squalene, stearic acid, triacetin, trimyristin, vanillin, and vitamin E.

Polar Solvent.

The polar solvent (or in the case of a block copolymer, the preferential solvent) can similarly serve multiple functions, including modulation of phase behavior (indeed, making nanostructured phases possible at all, in many surfactant systems), solubilization of the active, providing a polar environment for portions of the active molecule such as for example the polar regions of a protein, etc. The choice of a non-volatile polar solvent like glycerol can be important in processes such as spray-drying. The polar solvent may be:

a. water
b. glycerol
c. formamide, N-methyl formamide, or dimethylformamide
d. ethylene glycol or other polyhydric alcohol
e. ethylammonium nitrate
f. other non-aqueous polar solvents such as N-methyl sydnone, N-methyl acetamide, pyridinium chloride, etc.;
g. a mixture of two or more of the above.

Desirable polar solvents are water, glycerol, ethylene glycol, formamide, N-methyl formamide, dimethylformamide, ethylammonium nitrate, and polyethylene glycol.

It can be advantageous in certain circumstances to use, as the interior matrix, a composition that yields a nanostructured liquid or liquid crystalline phase upon contact with water (or more rarely, other polar solvent)—whether or not this dehydrated composition itself is a nanostructured liquid or liquid crystalline phase. In particular, this contact with water or a water-containing mixture could be either during a reconstitution step, or more preferably, during the application of the particle, most preferably after the coating releases, and the de-coated particle contacts an aqueous solution such as blood, extracellular fluid, intracellular fluid, mucous, intestinal fluid, etc. There are several reasons why this may be advantageous: to protect hydrolytically unstable actives or excipients; to limit premature release of water-soluble actives; and as a natural result of a production process such as spray-drying or freeze-drying that can induce dehydration. Removal of most, or all, of the water from a nanostructured liquid or liquid crystalline phase will often yield another nanostructured liquid or liquid crystalline phase, but can sometimes yield a structureless solution, precipitate, or a mixture of these with one or more nanostructured liquid or liquid crystalline phases. In any case, for many applications, it is the hydrated form that is important in the application of the particles, and thus if this hydrated form is a nanostructured liquid or liquid crystalline phase, then the composition of matter falls within the scope of the current invention.

Coatings.

As previously stated, the exterior coating 20 may be formed of a nonlamellar material. The term "nonlamellar" as applied to crystal structure herein should be taken in the following context. Lamellar crystalline materials, which are distinct from lamellar liquid crystalline phases, occur in organic compounds (typically polar lipids), inorganic compounds, and organometallics. Although these materials can be true crystalline materials and can thus exhibit long range three-dimensional lattice ordering of the constituent atoms (or molecules, in the case of an organic crystalline material) in space, the forces and interactions between atoms—which can include covalent bonding, ionic bonding, hydrogen bonding, steric interactions, hydrophobic interactions, dispersion forces, etc.—are much stronger amongst the constituent atoms or molecules than within the plane of a lamella than across distinct lamellae. For example, in the case of the layered structure of graphite, the atoms within a layer are covalently bonded with each other into a two-dimensional network, whereas between distinct layers there is no bonding, only the weaker dispersion forces and steric interactions. This absence of strong local inter-lamellar interactions gives rise to a number of physicochemical properties which make them undesirable as coating materials in the present invention.

To begin with, the physical integrity of lamellar crystals is inherently compromised by the weak local interactions between layers. This is dramatically evidenced by the comparison between graphite (a layered crystalline form of carbon) with diamond (a crystalline form of carbon that has three-dimensional bonding). Indeed, the fact that graphite is an important ingredient in certain lubricants, due to the ease with which the layers slide over each other, whereas diamond is an abrasive, illustrates the "liquid-like" (or "liquid crystal-like") character of layered crystalline structures in terms of their response to shear. This same inter-lamellar sliding effect is, in fact, the same effect that gives rise to the much lower viscosity of the lamellar liquid crystalline phase compared with that of other liquid crystalline phases, in particular compared with the very high viscoelasticity of the bicontinuous cubic phase. As a further indication of this liquid-like nature, the Moh's hardness of graphite is 1.0, whereas that of diamond is 10. The loss of integrity with shear in the case of graphite is seen in everyday life with "lead" pencils, which are graphite.

The detrimental effects associated with layered crystalline structures can be seen in every day life even in situations where macroscopic shear is not involved. According to a widely-accepted model of the structure of emulsions advanced by Stig Friberg, as reviewed by Larsson,. K. and S. Friberag, Eds. 1990, Food Emulsions 2" Edition, Marcel Dekker, Inc. NY, lamellar liquid crystalline or, commonly, lamellar crystalline coatings stabilize the oil droplets in an oil-and-water emulsion, and the water droplets in a water-in-oil emulsion. In commonly encountered emulsions such as milk, ice cream, mayonnaise, etc., the instabilities that are wellknown to the lay person—and in the field referred to as "breaking" of emulsions—are due in large part to the fluidity of these layered coating materials. Even in a quiescent emulsion, these layered coatings undergo continual disruption, streaming and coalescence, and with time any emulsion must ultimately succumb to the destabilizing effect of these disruptions.

And at yet another level, layered crystalline materials exhibit chemical instabilities of the type that would prevent their application as coatings in embodiments of the current invention. Consider the case of the Werner complexes isomorphous to nickel dithiocyanate tetra(4methylpyridine) that form clathrate compounds with a host lattice containing embedded guest molecules, in most cases yielding permanent pores upon removal of the guest. One such Werner complex was used as the coating in a particle in Example 22, thus illustrating the use of the present invention in creating particles with coatings possessing fixed, controlled-size and highselectivity pores. According to J. Lipkowski, Inclusion Compounds 1, Academic Press, London (1984), p. 59, "Layered structures of $Ni(NCS)_2(4\text{-MePy})_4$ are stable only in the presence of guest molecules while the beta-phases preserve their porosity even in the absence of guest molecules." The three-dimensional, non-layered structure of the beta-phases is discussed in detail in the same publication, such as: ". . . beta-phases . . . have a three-dimensional system of cavities interconnected through channels of molecular size".

Nonlamellar amorphous and semi-crystalline materials are materials comprising non-crystalline domains (or lacking crystallinity altogether) in which strong atomic interactions exist in all three dimensions. In the amorphous trehalose that provides the coating in Example 40, for example, the packing of these sugar molecules and the multiple hydrogen bonds that each individual molecule can participate in make this a compound that exhibits strong interactions in all three dimensions (and the amorphous property rules out any lamellar-type structure). Similarly amorphous PLGA has strong interactions between the carboxyl groups across neighboring polymer chains which, since the material is optically isotropic, are not limited to two dimensions. The release of a coating in a PLGA-coated particle will be chosen to be based on its hydrolysis rate in the body, as is well-known in the art, and not by mechanical shear or deformation as could occur in a particle coated with a lamellar coating. Since most production protocols used in industrial or pharmaceutical practice involve shear, release upon the application of such shear rates to a lamellar-coated particle system could be detrimental or disastrous in the context of such a process.

As is well-known in the art, in the case of polymers, polymers universally have amorphous domains: no polymer is ever 100% crystalline, and thus even high-crystallinity polymers are semi-crystalline and possess a finite fraction of amorphous domains. Often this is in the range of about 1–50%. The glass transition temperature of these amorphous domains can usually be detected by thermodynamic (e.g., DSC) techniques or rheometric measurements, though in certain very high-crystallinity polymers (greater than about 98%), this may be a difficult undertaking. Nevertheless, even in these high-crystallinity cases the amorphous domains can play important roles: they can mitigate structural problems associated with microcrystallite boundaries, thus conferring greater homogeneity and cohesiveness to microcrystalline polymers; this in turn can have strong effects on rheological properties and behavior as diffusional barriers; according to the fringed micelle model, an amorphous domain can provide a medium that allows for a single chain to extend through several microcrystallites, yielding a physical crosslinking (analogous to the physical crosslinking that occurs in thermoplastic elastomers); and their presence may in fact allow for crystallinity in high-MW polymers where the amorphous domains are the necessary result of chain folding. Being amorphous, these domains are non-lamellar regions in the polymer that are distinct from the crystalline regions but nonetheless actually play crucial roles in the crystallization of polymers and in determining their overall properties.

The exterior coating 20 can protect the internal core 10 and any active agent(s) or component(s) disposed therein, for example, against oxidation, hydrolysis, premature release, precipitation, shear, vacuum, enzymatic attack, degradation from other components of the preparation, and/or conditions external to the coated particles, for example, in their preparation such as pH, ionic strength, or the presence of bioactive impurities such as proteases or nucleases. Examples of each of these are:

oxidation: e.g. for antioxidants such as vitamin C, which are by their very nature sensitive to oxidation, or unsaturated lipids:

hydrolysis: e.g., for a drug with a labile ester bond:

premature release: during storage:

precipitation: e.g., for a drug in the protonated (hydrochloride) form that would deprotonate at the body pH and thereby become insoluble;

shear: e.g., in cases where processing after encapsulation endangers shear-sensitive compounds, such as proteins;

vacuum: e.g., in cases where processing involves vacuum-drying;

enzymatic attack: a peptide hormone, such as somatostatin, which is normally quickly digested by enzymes in the body, can be held active in circulation until reaching the site of release and action:

degradation from other components: e.g., where even a slight reactivity between an component disposed in the internal core and an exterior one could, over a shelf-life of months or years, pose a problem:

external pH: e.g., a drug in protonated form could be encapsulated at low internal pH to ensure solubility, but without requiring a low pH of the exterior liquid which would otherwise upset the stomach, external ionic strength: e.g., where a protein is encapsulated to avoid salting-out and denaturation;

external impurities such as proteases, nucleases, etc.: e.g., when the exterior contains a bioreactor-derived product from which removal of proteases might be prohibitively expensive.

Examples of suitable nonlamellar coating materials, namely, compounds which occur in nonlamellar form over useful temperature ranges, and which are in most cases of low toxicity and environmental impact are: ascorbic acid; ascorbic palmitate; aspartic acid; benzoin; beta-naphthol; bismuth subcarbonate; butylated hydroxytoluene; butylparaben; calcium acetate; calcium: ascorbate; calcium carbonate; calcium chloride; calcium citrate; calcium hydroxide; calcium phosphate, dibasic; calcium phosphate, tribasic; calcium pyrophosphate; calcium salicyiate,;calcium silicate; calcium sulfate; carmine; cetearyl alcohol; cetyl alcohol; cinnamaldehyde; citric acid; cysteine hydrochloride; dibutyl sebacate; esculin; ferric oxide; ferric citrate; ferrosoferric oxide; gentisic acid; glutamic acid; glycine; gold; histidine; hydrochlorothiazide; iodine; iron oxide; lauryl sulfate; leucine; magnesium; magnesium aluminum silicate; magnesium carbonate; magnesium hydroxide; magnesium oxide; magnesium silicate; magnesium sulfate; magnesium trisilicate; maleic acid; malic acid; DL-methyl salicylate; methylparaben; monosodium glutamate; propyl gallate; propylparaben; silica; silicon; silicon dioxide; sodium aluminosilicate; sodium aminobenzoate; sodium benzoate; sodium bicarbonate; sodium bisulfate; sodium bisulfite; sodium carbonate; sodium chloride; sodium citrate; sodium metabisulfite; sodium nitrate; sodium phosphate, dibasic; sodium propionate; sodium salicylate; sodium stannate; sodium succinate; sodium sulfate; sodium sulfate; sodium thiosulfate; sodium thiosulfate; succinic acid; talc; talc triturate; tartaric acid; tartaric acid; DL-tartrazine; tellurium; titanium dioxide; triacetin; triethyl citrate; trichloromonofluorethane; tromethamine and 2-hydroxy-n-cyclopropylmethyl morphinan hydrochloride; zinc oxide.

Calcium phosphate coatings are of interest in biomedical and pharmaceutical applications, since calcium phosphates are a major component of bone, teeth, and other structural components. For example, in the treatment of osteoporosis, the release of the appropriate pharmaceutical compound could be triggered by physiological conditions that induce dissolution of bone (and thus of the particle coating).

Potassium nitrate coatings are of interest in agricultural applications since the coating also act as plant fertilizers.

Iodine, aspartic acid, benzoic acid, butylated hydroxytoluene, calcium edetate disodium, gentisic acid, histidine, propyl gallate and zinc oxide can be particularly useful as coatings in potential pharmaceutical applications because they have relatively low water solubility (generally less than 5%) and are on the FDA list of approved inactive ingredients for injectable formulations.

Of particular interest as coating materials are clathrates. Examples of such materials are as follows:

1. Clathrates and inclusion compounds (some of which retain permanent porosity upon removal of the guest molecules):Werner complexes of the form $MX_2A_4$ where M is a divalent cation (Fe, Co, Ni, Cu, Zn, Cd, Mn, Hg, Cr), X is an anionic ligand (NCS—, NCO—, CN—, $NO_3^-$, Cl—, Br—, I—), and A is an electrically neutral ligand-substituted pyridine, alpha-arylalkylamine or isoquinoline, examples of A include 4-methylpyridine, 3,5-dimethylpyridine, 4-phenylpyridine, and 4-vinylpyridine. A wide range of guest molecules can be included in these complexes, examples being benzene, toluene, xylene, dichlorobenzene, nitrotoluene, methanol, chloromethane, argon, krypton, xenon, oxygen, nitrogen, carbon dioxide, carbon disulfide, etc.;

reversible oxygen-carrying chelates such as bis-salicyladehyde-ethylenediiminecobalt and other bis salicyladehyde iminecobalt derivatives, cobalt(II) dihistidine and related cobalt(II) arnino acid complexes, iron(II) dimethylglyoxime and nickel(II) dimethylglyoxime; and complexes of the form $K_2Zn_3[Fe(CN)_6]_2 \cdot xH_2O$, where certain values of the variable x correspond to complexes which yield permanent pores upon removal of the water.

2. Zeolites:

faujasite-type NaX zeolite;

faujasite-type NaY zeolite; and

VPI-5 zeolite.

Amorphous and Semi-crystalline Nonlamellar Materials.

In some embodiments of the present invention, the exterior coating of the particles of the present invention comprises nonlamellar materials which are not entirely in crystalline form. Such non-crystalline materials may be amorphous or semicrystalline. In the art, the term "amorphous" as applied to materials means lacking long-range order; this is in direct contrast to the case of a crystalline material, in which there is long-range order in the positions of atoms, such that their positions conform to a lattice with its associated periodicity. The x-ray diffraction pattern of an amorphous material will be absent of any Bragg reflections, and any short-range correlations can at most give rise to broad maxima in the diffraction pattern, maxima which exhibit neither the sharpness nor the functional form of a true Bragg reflection. By "semi-crystalline" is meant a material which has a mixture of crystalline domains and amorphous domains.

Those of skill in the art will recognize that many materials can exist in a crystalline, an amorphous, or a semicrystalline form, depending on the preparation of the material. For example, many materials which otherwise occur in crystalline form instead occur in amorphous form when spray-dried, freeze-dried (as exemplified in Example 40, below), or prepared in other methods that are of central importance in the food, cosmetic, and pharmaceutical industries.

Amorphous materials have a number of properties which make them advantageous for certain embodiments of the current invention. For example, one property of amorphous materials is that they are generally faster-dissolving than a corresponding (or comparable) material in crystalline form, and this can be advantageous in cases where fast dissolution of the exterior coating is desirable. Further, amorphous materials can be superior to their corresponding crystalline forms in certain material properties. For example, amorphous materials tend to exhibit higher ductility, and thus allow the adsorption of stress without cracking.

In general, small-molecule amorphous materials tend to exhibit lessor stability over time than their corresponding crystalline materials. In particular, a small-molecule amorphous material will often show a tendency to revert to a crystalline form over a period of time that is comparable to, or shorter than, timescales that are relevant for the storage and use of a product. In the case of high-MW polymers, even though the true equilibrium condition may be a crystal, kinetics of rearrangement can be so slow that the timescale required for attainment of this equilibrium is for all intents and purposes infinite, so that the material can be locked into an amorphous or semi-crystalline state. For certain applications, this may be highly desirable. For example, many of the well-known elastomers and plastics, such as natural rubber (an example of an elastomer) or polymethylmethacrylate (PMMA, also known as Plexiglass, an example of a thermoplastic), are amorphous materials.

Semi-crystalline materials can in certain ways offer significant advantages, though their occurrence as long-lasting states is largely limited to high-MW polymers. A semi-crystalline polymer with high crystallinity can offer high modulus due to the preponderance of crystalline domains, but a certain amount of ductility due to the presence of amorphous domains, which can absorb stress without cracking. A number of the most important polymers, both commodity and engineering plastics, are semi-crystalline.

Examples of materials which occur in an amorphous or semi-crystalline form that may be utilized in the practice of the present invention include: polydienes, polyallenes, polyacrylics and polymethacrylics (including polyacrylic acids, polymethacrylic acids, polyacrylates, polymethacrylates, polydisubstituted esters, polyacrylamides, polymethacrylamides, etc.), polyvinyl ethers, polyvinyl alcohols, polyacetals, polyvinyl ketones, polyvinylhalides, polyvinyl nitriles, polyvinyl esters, polystyrenes, polyphenylenes, polyoxides, polycarbonates, polyesters, polyanhydrides, polyurethanes, polysulfonates, polysiloxane, polysulfides, polysulfones, polyamides, polyhydrazides, polyureas, polycarbodiimides, polyphosphazenes, polysilanes, polysilazanes, polybenzoxazoles, polyoxadiazoles, polyoxadiazoiidines, polythiazoles, polybenzothiazoles, polypyromellitimides, polyquinoxalines, polybenzimidazoles, polypiperazines, cellulose derivatives, alginic acid and its salts, gum arabic and its salts, gelatin, PVP, tragacanth, agar, agarose, guar gum, carboxymethylcellulose, arabinogalactan, Carbopol, chitin, chitosan, Eudragits, glycogen, heparin, pectin, sugars (such as trehalose, lactose, maltose, and sucrose, or mixtures of sugars with albumin) and more complex carbohydrates, as well as amorphous forms of the coating materials listed above in connection with crystalline coating materials, obtained by processes that hinder crystallization, such as spray-drying, vitrification, etc.

In any case, taking the larger view, the availability of the full spectral range of amorphous, semi-crystalline and crystalline materials yields great power and flexibility to the technology of creating particles with nanostructured liquid and liquid crystalline interiors. The case of lactide-glycolide copolymers provides a particularly pertinent example, because these copolymers are amorphous over a range of lactide:glycolide ratios, and crystalline over other ranges. By adjusting this ratio, it is possible to alter the form of the material and thus its properties, thereby "tuning" the rate of hydrolysis of the coating material. This, in turn, "tunes" the rate of release of active agents disposed in either the coating or the particle interior.

Proteins, and perhaps to a lessor extent polypeptides, can also provide amorphous and semi-crystalline coating materials with advantageous properties. Due to the intimacy of interactions that are well-known between proteins and lipid matrices, the crystallization of a protein in an aqueous dispersion of nanostructured liquid or liquid crystalline particles, preferably of the reversed bicontinuous cubic phase, could yield particles of the instant invention wherein the coating was composed of semi-crystalline protein. Alternatively, gelation or precipitation of a protein at the surface of a nanostructured liquid or liquid crystalline particle could yield a particle of the instant invention wherein the coating was composed of amorphous protein. The presence of protein in the coating of such particles could serve one or more important roles, including: targeting (that is, the coating itself could serve a dual role as a targeting compound); inhibition of unfavorable protein adsorption (e.g., albumin binding); presentation of a biocompatible particle surface that would minimize uptake by the body's defenses (e.g., the RES) and yield long circulation times; and functional proteins that could perform metabolic functions at the site of delivery that might yield enhanced absorption, diminished drug degradation/metabolism, and/or regulation of cellular processes in concert with the drug action. Furthermore, since the release of the coating could be in response to enzymatic degradation (by, e.g., proteases), this could provide a means by which to achieve slow release, or targeted release to sites of accelerated metabolism.

Applications of the Invention.

The coated particles 1 of the present have application in a variety of fields. The coated particles 1 are adapted to absorb one or more materials from a selected environment, adsorb one or more materials from a selected environment or release one or more materials, such as active agents, disposed in the matrix. With respect to absorption, the coated particles may be used to harvest products or scavenge waste, in biological or chemical reaction processes, to carry catalysts in those processes, to remove toxins, antigens or waste products in medical applications, to identify a few examples.

With respect to adsorption, the coated particles may be used as chromatographic media and as adsorbents.

With respect to release, the coated particles may be used for the controlled release of pharmaceutical agents such as anticancer agents or photodynamic therapy agents, or cosmetic or cosmeceutical materials. An active agent may be disposed in the matrix for release upon the triggering of release. For example, a pharmaceutical or biologically active material may be disposed in the matrix, that is, it may be either dissolved, or dispersed, or in some cases be partially dissolved and the remainder dispersed.

In applications of these microparticles in drug-delivery or with embedded proteins or polypeptides (in particular receptor proteins), it can be highly advantageous to have an interior matrix which, although synthetic or semisynthetic, is designed to simulate closely the physiochemical properties of a natural biomembrane from a living cell. This could be important for the proper functioning of a receptor protein or other membrane component, for example, or for promoting assimilation of the interior matrix into the natural biomembrane in drug delivery, or especially in targeting of the microparticles. Physiochemical properties that can be important in such a context include the bilayer rigidity, (a measure of the resistance to bending), bilayer fluidity (a measure of the microviscosity of the bilayer interior), the acyl chain length and bilayer thickness, the order parameter as a function of position on the lipid acyl chains, the surface charge density, the presence or absence of segregated lipid domains of differing composition within the bilayer, bilayer curvature and monolayer curvature (for a discussion of the relationship between these two curvatures see H. Wennerstrom and D. M. Anderson, in Statistical Thermodynamics and Differential Geometry of Microstructured Materials, Eds. H. T. Davis and J. C. C. Nitsche, Springer-Verlag, 1992, p. 137), cholesterol content, carbohydrate content, and the lipid:protein ratio. By proper choice of composition, one can adjust these parameters to a large extent in an artificial system, namely a nanostructured liquid phase or liquid crystalline phase. For example, the bilayer rigidity can be reduced by the addition of amphiphiles, particularly aliphatic alcohols; and bilayer charge can be adjusted by adjusting the ratio between uncharged lipids (such as phosphatidylcholine) and charged lipids (such as phosphatidic acid). Also, the addition of cholesterol is important for the function of a number of membrane proteins. The lamellar phase, the reversed bicontinuous cubic phase, the L3 phase, and to a lesser extent the reversed hexagonal phase are in particular well suited for this approach. Thus, a particle of the present invention, with the interior matrix being such a phase with tuned physiochemical characteristics for the functioning of incorporated proteins or other biomolecules, can be very valuable in products for pharmaceutics, clinical assays, biochemical research products, etc.

Membrane proteins are generally dependent on a bilayer milieu in order to function properly and even to maintain proper conformation, and for such proteins the present invention—particularly with the bilayer properties tuned as described above—could be an excellent and very useful matrix. Examples of membrane proteins include, in addition to receptor proteins, such proteins as proteinase A, amyloglucosidase, enkephalinase, dipeptidyl peptidase IV, gamma-glutamyl transferase, galactosidase, neuraminidase, alpha-mannosidase, cholinesterase, arylamidase, surfactin, ferrochelatase, spiralin, penicillin-binding proteins, microsomal glycotransferases, kinases, bacterial outer membrane proteins, and histocompatibility antigens.

In view of the demanding requirements for the delivery of pharmaceuticals in the treatment of cancers, the advantages and flexibility of the present invention make it particularly attractive in the delivery and release of antineoplastic agents, such as for example, the following:

Alkylating Agents

Alkyl Sulfonates—Busulfan, Improsulfan, Piposulfan.

Aziriaines—Benzodepa, Carboquone, Meturedepa, Uredepa,

Ethyleneimines and Methvlmelamines—Altretamine, Triethylenemelamine, Triethylenephosphoramide, Triethylenethiophosphoramide, Trimethylolmelamine, Nitrogen Mustards—Chlorambucil, Chloramphazine, Cyclophosphamide, Estramustine, Ifosfamide, Mechlorethamine, Mechlorethamine Oxide Hydrochloride, Melphalan, Novembichin, Phenesterine, Prednimustine, Trofosfamide, Uracil, Mustard.

Nitrosourea—Carmustine, Chlorozotocin, Fotemustine, Lomustine, Nimustine, Ranimustine, Others—Dacarbazine, Mannomustine, Mitobronitol, Mitolactol, Pipobroman.

Antibiotics—Actacinomveins—Actinomycin FI, Anthramycin, Azaserine, Bleomvyins, Cactinomycin, Carubicin, Carzinophilin, Chromomycins, Dactinomycin, Daunorubicin, 6-Diazo-5-OXO-Leucine, Doxorubicin, Epirubicin, Mitomycins, Mycophenolic Acid, Nogalamycin, Olivomycins, Peplomycin, Plicarmcin, Porfiromycin, Puromycin, Streptonigrin, Streptozocin, Tubercidin, Ubenimex, Zinostatin, Zorubicin.

Antimetabolites

Folic Acid Analogs—Denopterin, Methotrexate, Pteropterin, Trimetrexate.

Purine Analogs—Fludarabine, 6-Mercaptopurine, Thiamiprine, Thioguanine,

Pyrimidine Analogs—Ancitabine, Azacitidine, 6-Azauridine, Carmofur, Cytarabine, Doxifluridine, Enocitabine, Floxuridine, Fluorouracil, Tegafur.

Enzymes—L-Asparaginase, etc.

Others—Aceglatone, Amsacrine, Bestrabucil, Bisantrene, Carboplatin, Cisplatin, Defosfamide, Demecolcine, Diaziquone, Eflorithine, Elliptinium Acetate, Etoglucid, Etoposide, Gallium Nitrate, Hydroxyurea, Interferon-to, Interferon-P, Interferon-y, Interleukin-2, Lentinan, Lonidamine, Mitoguazone, Mitoxantrone, Mopidamol, Nitracrine, Pentostatin, Phenamet, Pirarubicin, Podophyllinic Acid, 2-Ethylhydrazide, Procarbazine, PSK09, Razoxane, Sizofiran, Spirogermanium, Taxol, Teniposide, Tenuazonic Acid, Triaziquone, 2,2',2,1,1-Trichlorotriethylamine, Urethan, Vinblastine, Vincristine. Vindesine.

Androgens—Calusterone, Dromostanolone Propionate, Epitiostanol, Mepitiostane. Testolactone.

Antiadrenals—Aminoglutethimide, Mitotane, Trilostane.

Andandrogens—Flutamide, Nilutamide.

Antiestrogens—Tamoxifen, Toremifene.

Estrogens—Fosfestrol, Hexestrol, Polyestradiol Phosphate.

LH-RH Analogs—Buserelin, Goserelin, Leuprolide, Triptorelin.

Progestogens—Chlormadinone Acetate, Medroxyprogesterone, Megestrol Acetate, Melengestrol.

Antineoplastic (Radiation Source) Americium, Cobalt, $^{131}$I-Ethiodized Oil, Gold (Radioactive, Colloidal), Radium, Radon, Sodium Iodide (Radioactive), Sodium Phosphate (Radioactive), Antineoplastic Adjuncts Folic Acid Replenisher—Folinic Acid, Uroprotective—Mesna.

Other pharmaceutical compounds that are particularly well-suited for encapsulation according to the instant invention, and suffer from problems or limitations in the currently-marketed formulations, include: Dacarbazine, Ifosfamide, Streptozocin, Thiotepa, Nandrolone decanoate, Fentanyl citrate, Testosterone, Albendazole, Esmolol, Bleomycin sulfate, Dactinomycin, Amikacin sulfate, Gentamicin, Netilmicin, Streptomycin, Tobramycin, Doxorubicin, Epirubicin, Idarubicin, Valrubicin, Bacitracin, Colistimethate, Oxybutinin, Antithrombin III Human, Heparin, Lepirudin, Adenosine phosphate, Amphotericin B, Enalaprilat, Cladribine, Cytarabine, Fludarabine phosphate, Gemcitabine, Pentostatin, Docetaxel, Paclitaxel, Vinblastine, Vincristine, Vinorelbine, Batimastat, Rituximab, Trastazumab, Abciximab, Eptifibatide, Tirofiban, Droperidol, Aurothioglucose, Capreomycin disulfide, Acyclovir, Cidofovir, Pentafuside, Saquinavir, Ganciclovir, Cromolyn, Aldesleukin, Denileukin, Edrophonium, Infliximab, Doxapram, SN-38 (Irinotecan), Topotecan, Hemin, Daunorubicin, Teniposide, Trimetrexate, Octreotride, Ganirelix acetate, Histrelin acetate, Somatropin, Epoetin, Filgrastim, Oprelvekin, Leuprolide, Basiliximab, Daclizumab, Glatiramer acetate, Interferons, Muromonab-CD3, Clyclosporin A, Milrinone lactate, Buprenorphine, Nalbuphine, Urofollitropin, Desmopressin, Carboplatin, Cisplatin, Mitoxantrone, Estradiol, Hydroxyprogesterone, L-Thyroxine, Etanercept, Neostigmine, Epoprostenol, Methoxamine, Versed, Bupivacaine, Heparin, Insulin, Antisense compounds, Ibuprofen, Ketoprofen, Alendronate, Etidronate, Zoledronate, Ibandronate, Risedronate, and Pamidronate. These compounds represent the following classes of drug: Alkylating agent, Anabolic steroid, Analgesic, Androgen, Anthelmintic, Antiadrenergic, Antibiotic, Antibiotic, aminoglycoside, Antibiotic, antineoplastic, Antibiotic, polypeptide, Anticholinergic, Anticoagulant, Anticonvulsant, Antifungal, Antihypertensive, Antimetabolite, Antimitotic, Antineoplastic, Antiplatelet, Antipsychotic, Anesthetic, Antirheumatic, Antituberculosal, Antiviral, Antiviral (HIV), Asthma anti-inflammatory, Biological response modifier, Cholinergic muscle stimulant, CNS stimulant, DNA topoisomerase inhibitor, Enzyme inhibitor, Epipodophyllotoxin, Folate antagonist, Gastric antisecretory, Gene therapy agents, Gonadotropin-releasing, Growth hormone, Hematopoietic, Hormone, Immunologic agent, Immunosuppressant, Inotropic agent, Local anesthetic, Narcotic agonist/antagonist, Ovulation stimulant, Pituitary hormone, Platinum complex, Sex hormone, Thyroid hormone, TNF inhibitor (arthritis), Urinary cholinergic, Vasodilator, and Vasopressor. We note that the current invention is also very well suited for the incorporation of functional excipients, such as gum benzoin or essential oils that improve absorption of poorly-absorbed drugs, in some cases by inhibiting drug efflux proteins. As discussed in more detail elsewhere herein, there are a number of sites within, and at the surface of the particles, where actives, excipients, and functional excipients can be localized within the context of this invention.

Other examples of uses of coated particles of the present invention include:

1. Paints and inks. Including Microencapsulation of pigments; Cationic charging of pigments (where pH-dependence can be important); Fillers and texturizing agents for non-aqueous paints;

2. Paper. Including Microcapsular opacifiers (also in paints); Pressure-sensitive ink microcapsules for carbonless copying paper;

3. Non-wovens. Including Additives that adhere to fibers throughout processing;

4. Agricultural. Including controlled release of pheromones (some of which are otherwise volatile or environmentally unstable if not encapsulated) for insect control; Controlled release of insect chemosterilants and growth regulators (many of which are otherwise environmentally unstable): Controlled release of other pesticides (with temperature independence being important); Controlled release of herbicides; Encapsulation of the plant growth regulators ethylene and acetylene (that are otherwise volatile); Taste modifiers to deter mammalian pests (e.g. capsaicin), Nutrient and fertilizer release;

5. Environment and forestry. Including Controlled release of aquatic herbicides for weed control; Controlled release of other herbicides; Controlled release of nutrients in agriculture; Soil treatment and nutrient release; Encapsulation and release of chelating agents (e.g., for heavy metal contaminants): Control of deposition and environmental fate of actives (viz., through targeted release of crystal coating and/or adhesive property of cubic phase): Encapsulation of hygroscopic or other (e.g., urea and sodium chloride) "seeding" agents for meteorological control;

6. Vaccines. Including HIV gag, gag-pol transfection of cells as an example; Adjuvants for the proper presentation of antigens or antibodies;

7. Nuclear medicine. Including Separation of two (otherwise mutually-destructive) radionuclides into separate particles for treatment of cancer;

8. Cosmetics. Including Antioxidant, Antiaging skin cream: Separation of two components of an antiacne medication; Suntan lotions with encapsulated prostaglandins and vitamins; Encapsulation of fat-soluble vitamins, oxidatively sensitive vitamins, vitamin mixes; Encapsulation of volatile perfumes and other odorants; Encapsulated volatile perfumes for scratch and sniff advertisements, Encapsulation of volatile make-up removers or other cosmetics for sheet formation; Encapsulated solvents for nail polish removers (or the polish itself); Aerosol particles containing encapsulated hair dye; Sanitary napkins containing encapsulated deodorant;

9. Veterinary. Including Controlled release of volatile anti-flea compounds; Encapsulated feed additives for ruminants; Encapsulation of anti-microbial and insecticides in animal husbandry;

10. Dental. Including Controlled-release dentifrice components, particularly hydrolytically unstable anti-calculus compounds; Delivery of oral anti-cancer compounds (photophyrin);

11. Polymerization catalysts in one-pot (single-package) resin systems;

12. Household Products. Including controlled-release air fresheners, perfumes; Controlled-release insect repellants; Laundry detergents (e.g., encapsulated proteases); Other detergency applications; Softeners; Fluorescent brighteners;

13. Industrial. Including encapsulation of phosphine, ethylene dibromide, etc. volatiles for fumigating stored products; Catalytic particles; Activated charcoal microparticles for sorption and purification, 14. Polymer additives. Including polymer additives for protection of wires,paper cartons etc, from rodents; Impact modifiers; Colorants and opacifiers; Flame retardant and smoke suppressants; Stabilizers; Optical brighteners; Limitations in current polymer-based encapsulation of additives include low melting point (during processing, polymer-polymer incompatibility, particle size limitations, optical clarity, etc. Some polymer additives used for lubrication of the polymer are based on waxes, which suffer from low melting point, except for certain synthetic waxes which are expensive;

15. Food and beverage processing. Including Encapsulation of (volatile) flavors, aromas, and oils (e.g., coconut, peppermint); Encapsulation of vegetable fats in cattle feeds; Encapsulated enzymes for fermentation and purification (e.g., diacetyl reductase in beer brewing); Encapsulation as an alternative to blanching, for improved lifetime of frozen foods; Microencapsulated tobacco additives (flavorings); pH-triggered buffering agents; Removal of impurities and decolorization using activated charcoal encapsulated in a porous material;

16. Photographics. Including Fine-grain film with dispersions of submicron photoreactive particles; Faster Film due to optical clarity (and thus higher transmission) and shorter diffusion times of submicron dispersion; Microencapsulation of photoprocessing agents;

17. Explosives and propellants. Including both liquid and solid propellants and explosives are used in encapsulated form; also, water is used in encapsulated form as a temperature moderator in solid propellants;

18. Research. Including Microcapsule-packed columns in extractions and separations; Biochemical assays, particularly, in pharmaceutical research and screening;

19. Diagnostics. Including encapsulated markers for angiography and radiography and clinical assays involving milieu-sensitive proteins and glycolipids; indeed, particles incorporating certain radiopaque or optically dense materials could themselves be used for imaging, and when coupled to targeting compounds as described herein could target specific sites in the body and allow their visualization.

Desirable triggers for commencing the release of active agents, or alternatively commencing absorption, are:

I. Release is by dissolution or disruption of the coating
  A. Intensive variable
    1. pH
    2. Ionic strength
    3. Pressure
    4. Temperature
  B. Extensive variable or other
    1. Dilution
    2. Surfactant action
    3. Enzymatic activity
    4. Chemical reaction (non-enzymatic)
    5. Complexation with target compound
    6. Electric current
    7. Irradiation
    8. Time (i.e. slow dissolution)
    9. Shear (critical shear rate effective)

II. Release or absorption is via pores in the coating, circumventing the need for dissolution or disruption of the coating
    1. Selective by pore size vs. compound size
    2. Selective by pore wall polarity vs. compound polarity
    3. Selective by pore wall ionicity vs. compound ionicity
    4. Selective by pore shape vs. compound shape
    5. Selective by virtue of the fact that some compounds or ions form porous inclusion compounds with the coating, whereas others do not (although this is generally a combination of the above 4 effects).

Methods for Making Particles of the Invention.

In a preferred embodiment, the coated particle may be made by 1. providing a volume of the matrix that includes at least one chemical species having a moiety capable of forming a nonlamellar material upon reaction with a second moiety and 2. contacting the volume with a fluid containing at least one chemical species having the second moiety under nonlamellar solid material-forming conditions so as to react the first moiety with the second moiety and subdividing the volume into particles by the application of energy to the volume, or performing this subdivision into particles before, and/or after, the chemical reaction.

Alternatively, the coated particle can be made by one of the following processes:

providing a volume of the matrix that includes a material in solution in it that is capable of forming a nonlamellar material that is insoluble in the matrix and causing the aforesaid material to become insoluble in the matrix and subdividing the volume into particles by the application of energy to the volume;

dispersing particles of said matrix into a fluid that includes at least one chemical species having a moiety capable of forming a nonlamellar material upon reaction or association with a second moiety and adding to said dispersion at least one chemical species having said second moiety to react said first moiety with said second moiety;

dispersing particles of said matrix into a fluid that includes at least one chemical species having a moiety capable of forming a nonlamellar material upon reaction or association with a second moiety, adding to said dispersion at least one chemical species having said second moiety to react said first moiety with said second moiety, and subdividing the resulting material into particles by the application of energy to said material;

dispersing a volume of said matrix in a form of said nonlamellar material selected from the group consisting of liquefied form, solution, or fluid precursor, and solidifying said nonlamellar material by a techniques selected from the group consisting of cooling, evaporating a volatile solvent, or implementing a chemical reaction;

dispersing or dissolving a volume of said matrix in a liquid comprising said nonlamellar material in solution or dispersed form and comprising also a volatile solvent, and spray-drying said solution or dispersion; or applying spray-drying, electrospinning, or other comparable process to a solution or dispersion that contains the components of both the matrix and the coating. Or, a combination of these processes can be used.

In a general method, a volume of the matrix is loaded with a compound A capable of forming a nonlamellar material on reaction with compound B, and a fluid (typically an aqueous solution, often referred to as the "upper solution") containing a compound B is overlaid on this, and the contact between compound A and compound B induces precipitation at the interior/exterior interface, which coupled with the application of energy, such as sonication, causes particles coated with the nonlamellar material to break off into the fluid. This method of the present invention is uniquely well-suited for producing aqueous dispersions of coated particles having coatings of materials with low water solubilities, i.e., preferably less than about twenty (20) grams per liter of water and even more preferably less than about ten (10) grams per liter of water. It is highly advantageous in these processes for component A to be dissolved (not merely dispersed or suspended) in the matrix before the contact with B and sonication begins, in order to obtain a homogeneous dispersion of microparticles in the end. As discussed above, this is one reason (in addition to requirements for optimizing solublilization of actives, particularly biopharmaceuticals, in the matrix) for the importance of a nanostructured matrix having aqueous microdomains, in order to allow for the solubilization of compound A which in many cases is soluble only in polar solvents. In particular, reactions yielding nonlamellar organic precipitates are generally performed most conveniently and effectively in aqueous media, and reactions yielding nonlamellar organic precipitates from solubilized precursors are often most conveniently and effectively selected to be pH induced protonation or deprotonation reactions of soluble salt forms of the desired nonlamellar exterior coating material, where water (or an aqueous microdomain) is an obvious medium.

Alternatively, a cool temperature, or a crystallization promoter, or electric current could be used to produce precipitation.

In addition to sonication, other standard emulsification methods could be used as energy inputs. These include microfluidization, valve homogenization [Thornberg, E. and Lundh, G., 1978) J. Food Sci. 43:1553] and blade stirring, etc. Desirably, a water-soluble surfactant, preferably an amphiphilic block copolymer of several thousand Dalton molecular weight, such as Pluronic F68, is added to the aqueous solution in order to stabilize the coated particles against aggregation as they form. If sonication is used to promote particle formation, this surfactant also serves to enhance the effect of sonication.

Many of the nonlamellar material-coated particles described in the Examples were made by a process in which two or more reactants react to form a precipitate at the interface between the external solution and the nanostructured liquid or liquid crystalline phase, and the precipitate forms the exterior coating. Another method which bears important similarities, as well as important differences, to this method is a general method in which the material that is to form the coating, call it material A, is dissolved in the liquid phase material or liquid crystalline phase material, with this dissolution being promoted by the change of one or more conditions in the material, such as an increase in temperature (but it could be another chance such as decrease in pressure, addition of a volatile solvent, etc.). This change must be reversible, so that upon reversal of the condition—decrease of the temperature, increase in pressure, evaporation of solvent, etc.—the system reverts to a two-phase mixture of a nanostructured liquid or liquid crystalline phase material and a nonlamellar material A. Energy input is applied, sometimes before the nonlamellar material A has the time to coarsen into large precipitates, where this may be through the application of ultrasound, or other emulsification methodology. This causes the breaking off of particles coated with nonlamellar material A.

For the case where temperature is used, the solubility of compound A in the nanostructured liquid phase material or nanostructured liquid crystalline phase material must change with temperature, and the higher the magnitude of the slope of the solubility versus temperature plot, the smaller the temperature increment needed to perform this process. For example, the solubility of potassium nitrate in water is a very strong function of temperature. A fundamental difference between the precipitation reaction process and this type of process is that in this type of process, only one compound (A) is needed in addition to the nanostructured interior matrix. In the precipitation reaction method, at least two compounds are needed, component A which is in the nanostructured phase, and component B which starts out in the exterior phase ("upper solution") which is overlaid on top of the nanostructured phase. Component B in that case is often simply a suitably chosen acidic or basic component. This serves to point out a similarity between the two processes, in that the presence of component B in the exterior phase can alternatively be thought of as a "condition" (in particular, pH in the acid/base case) which causes the precipitation of A, that is, A may be solubilized by the use of basic pH, and this is reversible by the use of acidic pH conditions, which are applied by the presence of the exterior phase. Probably the most important distinction between the two methods is whether the change in conditions that causes the precipitation of A occurs only when and where the exterior phase ("upper solution") contacts the nanostructured phase, as in the A/B precipitation reaction, or whether it is occurring simultaneously throughout the bulk of the nanostructured phase, as in the temperature-induced precipitation.

It is also possible to use a process which is a combination of the A/B reaction process and the temperature process described above. Typically in such a scheme, the compound desired as the particle coating would be added to the matrix in two chemical forms. The first would be the chemical form of the final coating, typically the free acid (free base) form of a compound, which would be soluble only at elevated temperature and insoluble in the matrix at the temperature of particle formation. The second would be a precursor form, typically the salt form made by reacting the free acid with a base such as sodium hydroxide (or reacting the free base form with an acid such as hydrochloric acid), where this precursor form would be soluble in the matrix even at the temperature of particle formation. For example, for the case of a benzoic acid particle coating, both benzoic acid and sodium benzoate would be added to the matrix, where the matrix is such that is does not dissolve benzoic acid at ambient temperature, but does at a higher temperature. The upper solution would contain the necessary component(s) to convert the precursor form to the final coating form, such as hydrochloric acid in the case of sodium benzoate. Upon heating (so that both forms are substantially dissolved), and then cooling, overlaying the upper solution, and sonicating or otherwise adding energy to the system, the formation of coated particles would involve the two methods of cooling-induced precipitation and reaction-mediated formation and precipitation of coating. This could have advantages, in terms of providing two sources of coating material that could result in particle coverage at an earlier stage than with either method separately, thus providing added protection against particle fusion (and possibly leading to a more uniform particle size distribution), and more efficient particle formation with less energy input requirement, etc. Other methods that may be used for making coated particles of the present invention are: A. Electrocrystallization, B. Seeding (with supersaturated solution in matrix, seed in exterior phase), C. Promotion (with supersaturated solution in one phase, crystallization promoter in the other phase), D. Inhibition removal (with supersaturated solution in one phase and seed in the other phase), or E. Time method (precipitate grows slowly from supersaturated solution in interior phase).

In order to form many of the desired exterior coatings, including nearly all of the inorganic ones, one of the reactants (and usually both) will inevitably be soluble only in water or other polar solvent. In particular, most of the salts that are used in these precipitation reactions will dissolve only in highly polar solvents. At the same time, in order for a matrix material to be dispersible in water in accordance with the present invention, it appears to be a highly desirable, if not an absolute, condition that the interior phase material not be of substantial solubility in water, otherwise some or all of the material will dissolve in the upper solution rather than be dispersed in it. Therefore, in order to form these coatings, the matrix must satisfy two conditions:

condition 1: it must contain aqueous (or other polar solvent) domains: and condition 2: it must be of low solubility in water, i.e., sufficiently low (or with sufficiently slow dissolution kinetics) that substantial dissolution of the phase does not occur during the process of particle production from the phase (typically 5 to 100 minutes to disperse the entire material into particles), since this would substantially reduce the yield efficiency and could thus diminish the overall attractiveness of the method. These two conditions are working in nearly opposite directions, and very few systems can be found that will satisfy both. Nanostructured liquid phase materials and liquid crystalline phase materials of the reversed type or the lamellar type, are several of these very few systems. In some cases, it will be advantageous to incorporate into the upper solution one or more of the components that are in the nanostructured liquid or liquid crystalline phase, and at times in appreciable amounts. Indeed, there are instances when it may be advantageous to have a nanostructured surfactant-rich liquid phase for the upper solution. In particular, this could occur when the matrix phase is not in equilibrium with water (or a dilute aqueous solution) but is in equilibrium with another liquid or liquid crystalline phase, such as a micellar phase or even a low-viscosity lamellar phase. Thus, as the "fluid" referred to in the general description of the process given above, one could use such a phase, or such a phase to which additional components, such as reactant B and/or amphiphilic block copolymer stabilizer have been added. In this case there might well be no complications by any incorporation of this upper phase into the microparticles, should that occur, since the upper phase could be (and generally would be) chosen so as to be in equilibrium with the matrix phase (except possibly for exchange of the active ingredient between the two materials, which would have some consequences but these would often be relatively unimportant). After formation of the coated particles, which would originally be dispersed in this upper "solution", through the use of filtration or dialysis the continuous outer phase could be changed from this to another medium, such as water, saline, buffer, etc.

In other embodiments of the present invention, advantages can be obtained by using a precursor to the coating material that localizes preferentially the surface of particles of the nanostructured liquid or liquid crystalline matrix, and dispersing the nanostructured liquid or liquid crystalline phase-often with the aid of this surface-localized precursor-prior to converting this precursor to the actual coating material. This is especially preferred in the case where a surface-active precursor can be found, or when the precursor can otherwise be substantially localized near the surface of the dispersed particles, by a favorable interaction with another component (ionic pairing, hydrogen bonding, etc.), or by a non-specific effect such as the hydrophobic effect, or by selecting a precursor or precursor-containing solution with the proper surface energy. When this can be achieved, as it is in Example 41 below, then the localization of the precursor at the particle surface can be maintained throughout its conversion to the coating resulting in good intimacy between the particle and coating and efficient use of the coating material. In Example 41, the sodium salt of N-acetyltryptophan, which is a surface-active compound (due to the hydrophobicity of N-acetyltryptophan, augmented by the polarity of the ionized carboxylate group at one end), is used to disperse a cubic phase into microparticles with a particle surface that is rich in this precursor to the final coating material, which in this case is the zinc salt of N-acetyltryptophan. This is a very general approach, for example since the most useful coating materials are of course of low solubility in water, and thus each possesses at least one dominant hydrophobic group, but also has at least one polar group that allows it to have sufficient solubility or interaction with water in some precursor state; this is in fact tantamount to saying that it is an amphiphile, or even a surface-active compound, in this precursor state (or that such a state can be found). Other approaches for localizing the precursor at the particle surface include: ion-pairing the precursor to an oppositely-charged molecule that partitions strongly into the cubic phase; using a melted or solubilized form of the precursor such that the surface energy of the melted precursor or precursor solution favors its localization in between the nanostructured phase and the exterior phase in which the nanostructured phase is dispersed; choosing a precursor that has favorable interactions such as extensive hydrogen bonding with the nanostructured phase surface, particularly in the case where the precursor (and coating) is a polymer, so that it is by virtue of its high MW excluded from the interior of the nanostructured phase particle; invoking specific interactions such as antibody-antigen or receptor-ligand interactions; and using a precursor, preferably a polymer or biomacromolecule (protein, nucleic acid, polysaccharide, etc.) that is substantially insoluble in the nanostructured phase but contains hydrophobic anchor groups that partition into the nanostructured phase, where such hydrophobic anchors are known in the art and typically are alkanes or cholesterol-derivatives that are grafted onto the polymer or biomacromolecule.

As exemplified in Example 42, a related approach is one in which the matrix is dispersed in the precursor itself. That is, the precursor forms the continuous (exterior) phase of a dispersion of microparticles of the matrix. Then, this precursor is converted to the coating material, entrapping the microparticles (if and when they remain as nanostructured liquid or liquid crystalline bodies) within the coating material.

In this type of approach, there is first the step of dispersing the matrix material, with in many cases the precursor playing a central role as a dispersant or matrix, followed by the step of converting the precursor to the coating material, be it by chemical reaction (often as simple as an acid-base reaction or formation of a complex by the introduction of multivalent ions, as in Example 41), cooling, evaporating a volatile solvent, or other method. This series of actions can result either in a dispersion of coated microparticles, or conglomerates of such particles which one may want to separate by a second dispersing step (or it can yield a combination of conglomerates and dispersed microparticles). In both Examples 41 and 42, macroscopic particles were the result of these two steps, and a second dispersing step is required if the resulting contiguous solid is to be reduced to microparticles, as was performed in Example 41, where the final result was a dispersion of submicron-sized, coated microparticles.

As discussed above, in certain embodiments of this invention the interior matrix will be a dehydrated variant of the desired phase, that will form the desired nanostructured liquid or liquid crystalline phase upon contact with a water-containing fluid. There are three general ways in which such a particle can be produced. One is to use a process similar to that used in Example 42, where a matrix or, in this case dehydrated matrix, is dispersed in a non-aqueous solution or melt that is, or contains, a precursor of the coating material; upon cooling or otherwise converting this precursor to the coating, the dehydrated matrix would then be the encapsulated entity. A second general method is to apply a drying process, such as freeze-drying, electrospinning, or preferably spray-drying, to a water-containing dispersion of the particles in which the coating material (or a precursor thereof) has been dissolved or very finely dispersed. And a third general method is to dissolve or disperse all the components of the coating and of the matrix, either including or excluding the water, in a volatile solvent and applying a drying process, again preferably spray-drying. Several of these methods can avoid the use of water completely, which would be important in the case of actives (or special excipients) that should not contact water even during production.

Incorporation of Targeting Groups and Bioactive Compounds.

The utilization of amorphous and semi-crystalline materials as exterior coatings in the instant invention makes it all the more practical to incorporate, in a number of different ways, chemicals or chemical groups that can be invoked to target particles temporally and spatially, for example, to target particles to specific sites in the body. Similarly, other bioactive compounds incorporated on or in the coating could serve important functions, such as: absorption enhancers such as menthol could be present so as to increase permeability of absorption barriers (lipid bilayers, gap junctions) prior to or concomitant with the release of drug; proteins or other adsorption-modulating materials could be incorporated that would inhibit unfavorable binding of endogenous proteins such as albumin; adjuvants could be incorporated that would enhance the effect of vaccine components or other immune modulating materials. In general, an amorphous or semi-crystalline material can, for example, incorporate molecules or even submicron solids as embedded materials, more readily and efficiently than with crystalline materials which tend to exclude other materials during their crystallization—particularly when the crystallization is performed in accordance with the tight regulations that govern the pharmaceutical industry. Furthermore, covalent or ionic attachment of organic groups to polymers at their surfaces is a well-developed art. U.S. Pat. Nos. 6,344,050 and 5,484,584 (incorporated herein by reference in their entirety) are examples of methods known in the art for attaching molecular targets to polymers and microparticle coatings in particular. Antibodies, steroids, hormones, oligo- or polysaccharides, nucleic acids, vitamins, immunogens, and even nanoprobes are all examples of a wide range of materials that could be attached to particles of the instant invention with an exterior phase of amorphous, semi-crystalline, or less likely crystalline, material.

It is also within the scope of this invention to use pharmaceutical actives themselves as coatings, with the nanostructured interior playing one or more of several roles: enhancing absorption by virtue of surfactancy and/or interactions with biomembranes; solubilizing and then releasing absorption enhancers (e.g., gum benzoin), acids, bases, buffers, specific ions (e.g., manganese in the case where lectin binding is important), modulators of protein binding or activity, or other bioactive materials; and providing a matrix ensuring the proper presentation of molecular recognition sites.

While it is not always crucial for a given application to know the exact localization (or more precisely, the spatial probability distribution) of a targeting moiety within or in association with a particle, this may be an important consideration in the design of a particle-targeting moiety combination, and the instant invention lends itself to a good deal of flexibility and power in this respect. Typically, targeting moieties could be substantially localized at one or more of the following sites in reference to the coated microparticle:

1) in the interior of the particle, i.e., dissolved or dispersed in the nanostructured liquid or liquid crystalline phase interior; this locality can offer the distinct advantage of providing a "biomimetic" milieu for the targeting moiety, a milieu which can comprise a lipid bilayer as well as hydrophilic domains each of which can be tuned to optimize the environment;

2) at the outer surface of the interior—particularly if there is a distinct phase in between the interior phase and exterior coating, such as an aqueous layer; such a location could be particularly advantageous for a particle that would present its targeting moiety at the new outer surface after release of the exterior coating;

3) adsorbed to the inner surface of the exterior coating; in this location, as well as in the other locations listed here, there may be a synergy between the solid shell and the targeting moiety, in that certain solid materials (such as aluminum-based compounds, for example) can sometimes act as adjuvants, to increase the effectiveness of molecules in the body particularly if they are meant to interact with the body's immune system;

4) embedded in the exterior coating, which as discussed above is most likely to be achievable if the coating is amorphous or at least semi-crystalline;

5) at the surface of the exterior coating, either adsorbed or bound via, e.g., covalent, ionic, hydrogen bonding, and/or hydrophobic interactions;

6) attached to, but at a distance from, the surface of the exterior coating, through attachment via a flexible spacer, e.g., a polymer that is attached (e.g. by covalently bonding) at one end to a component of the particle (interior or exterior) and at the other end to the targeting moiety. Experience with other types of microparticles in the art has shown that this is generally an excellent approach for achieving good targeting because it preserves important conformational and diffusional degrees of freedom that are sometimes required for good docking of a targeting moiety with a receptor or target.

It should be noted that in the important case wherein a flexible spacer extends between the targeting moiety and the interior nanostructured phase, it may be possible to reap the advantages inherent in both locations, namely, before dissolution of the coating the moiety would be in a biomimetic environment provided by the nanostructured interior phase, and then after dissolution of the coating the moiety would be tethered to the (now uncoated) nanostructured phase and thus relatively free from hindrance in its interactions with receptors.

Beyond that fact that the interior phases of the instant invention are well-suited for solubilization of targeting moieties such as proteins, peptides, nucleic acids, polysaccharides, and maintenance of their conformation, it is also important that many of the lipids, surfactants, and block copolymers which form the basis of many of the embodiments in the instant invention lend themselves in a very natural way to modulating the properties of these moieties and their interactions with receptors in the body. For example, it is known in the art that close association between polyethylene glycol (PEG) chains and proteins or peptides can have a dramatic effect on stabilizing these peptides, as well as reducing their degradation by enzymes in the body, in many cases without negating their ability to interact with receptors. U.S. Pat. No. 6,214,966 (the contents of which are hereby incorporated by reference in entirety) provides examples wherein PEGylation of polypeptides can enhance their performance in the body, including reduced immunogenicity and slower clearance. Furthermore, this effect can be even more dramatic when the peptide is associated with a hydrophobic chain (or cholesterol-like group) in conjunction with the PEG chain. U.S. Pat. No. 6,309,633 (the contents of which are hereby incorporated by reference in entirety) provides examples of peptides that show greatly increased stability, resistance to enzymes, and oral absorption when coupled to PEGylated hydrophobic chains or ring systems. Many of the surfactants and lipids referred to in this specification are PEGylated, or contain other oligomeric or polymeric chains that can substantially modify the fate of drugs in the body—or of targeting moieties, as is suggested here.

A number of compounds could potentially be used as targeting moieties in a pharmaceutical application of particles of the instant invention. To begin with certain lipids, such as Lipid A, have very specific interactions with components of the immune system, for example, and can be incorporated into the interior phase or in association with the coating. Similarly, block copolymers in which one of the blocks could have targeting potential, such as glycogen and heparin, may be utilized. Small molecules that could be present either in the interior or exterior to achieve a degree of targeting include sterols, fatty acids, gramicidin, fragments or simulants of appropriate protein epitopes, and amino acids including aspartic acid, cysteine, tryptophan, leucine and others. Leucine is an example of a compound that is recognized and bound by a specific protein in the body (the branched-chain amino acid transporter). Several Examples below describe the production of particles coated with leucine.

The ability of the interior phases of the instant invention to provide for solubilization and stabilization of biomolecules, such as the targeting moieties of focus here, has been described above, where a number of examples of membrane proteins are given (receptor proteins, such proteins as proteinase A, amyloglucosidase, enkephalinase, dipeptidyl peptidase IV, gamma-glutamyl transferase, galactosidase, neuraminidase, alpha-mannosidase, cholinesterase, arylamidase, surfactin, ferrochelatase, spiralin, penicillin-binding proteins, microsomal glycotransferases, kinases, bacterial outer membrane proteins, and histocompatibility antigens), many of which could serve a targeting role if incorporated in particles of the instant invention. Examples of polymeric components adsorbed to the exterior coating that could serve as attachment points for targeting moieties, include, for example, stabilizing layers on the exterior, i.e., outside the exterior coating 20 such as polyelectrolytes or surfactant monolayers (as discussed above). The Pluronic F-68 that is used in a number of the Examples is one such polymeric surfactant.

In yet another embodiment of the invention, "externally-directed targeting" of the coated particles may be achieved. This may be accomplished by directing particles coated with certain magnetically responsive materials discussed above (e.g. ferric oxide) through the application of magnetic fields.

Antibodies are broadly useful for targeting to specific sites or molecules in the body or other environments, and can be incorporated at various sites in a particle as discussed above. In particular, intact antibodies with their more hydrophobic Fc fragment are prone to partitioning into matrices of the type used in this invention, and furthermore it is well known that antibodies can be adsorbed or attached (including covalently) to solid surfaces with retention of binding and binding specificity. Commercial sources supply antibodies to, for example, each of the following:

8-hydroxy-guanosine, AAV (adeno virus), ACHE (acetylcholinesterase), ACHER (acetylcholine and NMDA receptor), acid phosphatase, ACTH, Actin (cardiac, smooth muscle, and skeletal), Actinin, Adeno-associated virus, adenosine deaminase, Adipophilin (adipocy differentiation related peptide), Adrenomedulin 1–6, Advanced glycation end-products (AGE), alanine transaminase, albumin, alcohol dehydrogenase, aldehyde dehydrogenase, aldolase, Alfentanil AB, Alkaline Phosphatase, alpha Actinin, Alpha-1-antichymotrypsin, alpha-1-antitrypsin, alpha-2-macroglobulin, alpha-catenin, beta-catenin and gamma cateinin, Alpha-Fetoprotein, Alpha-fetoprotein receptor, Alpha-Synuclein, Alzheimer Precursor Protein 643–695(Jonas), Alz-90, Precursor Protein A4, amino acid oxidase, Amphetamine, amphiphysin, amylase, amylin, Amylin Peptide, Amyloid A and P, Amyloid precursor protein, ANCA (Proteinase PR3), androgen receptor, Angiogenin, Angiopoietin-1 and Angiopoietin-2 (arig-1/Ang-2), Angiotensin Converting Enzyme, Angiotensin II Receptor At1 and At2, Ankyrin, Apolipoprotein D, Apolipoprotein E, arginase I, B Arrestin 1 and B Arrestin 2, ascorbate oxidase, asparaginase, aspartate transaminase, Atpase (p97), atrial Natriuretic Peptide, AU1 and AU5, Bacillus Antracis (Anthrax) and Bacill, antracis lethal factor, Bad, BAFF, Bag-1, BAX, bcl-2, BCL-XI, B Nerve Growth Factor, beta Catenin, Benzoylecognine (cocaine), beta-2 microglobulin, beta Amyloid, Galactosidase, beta Glucuronidase, Blood Group antigens (RhoD, A1,A2 A1,A2,A3, B, A, Rh(0)D, RhoC, B M, N), Blood Group H antigen, bombesin and bombesin/gastrin releasing peptide, Bone Morphogenetic Protein (BMP), Bone marrow stromal cell antigen, BST-3, Borrelia burgdorferi garinii, borrelia burgdorferi sensustricto, Bovine Serum, Bradykinin Receptor B2, Brain derived neutrophic factor, Bromodeoxyuridine, CA 19-9, CA 125, CA 242, CA 15-3, CEA, Ca+ ATPase, Calbindin D-28K (Calcium binding protein), Calgranulin A, Cadherin, CD144, Calcineurin, Calcitonin, Calcitonin gene related peptide, Calcium Channel, Caldesmon, Calmodulin, Calnexin, Calpactin light chain, Calpain, Calpastatin, Calreticulin, Calretinin, Calsequestrin, Cam Kinase II, Canine Distemper virus, carbonic anhydrase I and II, Carboxypeptidase A, B and E, Carboxypeptidase Y, Cardi, Troponin C and T, cardiotrophin-1, Caspase 3 (CPP32), Catalase, Catenins, Caveolin 1, 2 a and 3, CCR, CD44 (HCAM), CD56 (NCAM), CDK2, CDK4 (Cyclin Dependent Kinase C), Carcinoembryonic Antigen, Cellular antigens, CFTR (cystic fibrosis transmembrane conductance protein), chemokine receptors, chlamydia, CHO cell (Chinese Hamster Ovary Cell) Proteins, cholera toxin, choline oxidase, Chondroitin, Chloramphenic, Acetyltransferase(CAT), Chromogranin A, B and C (Secreogranin III), cholesterol oxidase, Chymotrypsin, Cingulin, Citrate Synthethetase, C-kit/stem cell factor receptor, CK-MB, Clathrin Antigen, Clostridium Botulinum D Toxoid, Clusterin, C-MYC, CNS Glycoprotein 130kD, Collagen Type IV and Type VII, Complement 5b neoepitope, Complement C3a, C3b, C5 and C9, complexin 2, Corticoliberin (CRF), C-peptide, CRF (Corticotropin Releasing Factor), Corticotropin releasing factor receptor, COX-1 and Cox-2, CPP32 (also known as Caspase 3, apopain or Yama), Creatine transporter, C-Reactive Protein (CRP), Cryptosporidium, CXCR-5, Cyclin A, Cyclin D1, D2 and D3, Cyclosporine A, Cylicin I, Cytochrome B5, Cytochrome C, Cytochrome oxidase, Cytochrome P450, Cytokeratin Types I and II, Cytomegalovirus, DAP Kinase, Dendritic cells, Desmin, Desmocollin 1, 2 and 3, Desmoglein 1, 2 and 3, Desmoplakin 1 and 2, Dextranase, DHT (Dihydrotestosterone), Dihydrofolate Reductase (DHFR), Dioxin, Diptheria toxin, Distemper, DJ-1, DNA single-stranded, DNA double stranded, DNA Topoisomerase II and Phosphotopoisomerase IIa+II alpha/beta, Dopamine, Dopamine Beta-Hydroxylase, Dopamine Receptor, Dopamine Transporter, Drebrin, Dysferlin, Dystrobrevin, *E.Coli* expression plasmid, Elastase, Elastin, Endocrine Granu, Constituent (EGC), Endorphin, Endothelial cell, Endothelin, Endothelin Receptor, Enkephalin, enterotoxin *Staphylococcus aureus*, Eosinophil Peroxidase, Eosinophil derived neurotox, (EDN), Eotaxin, Eotaxin-2, Epidermal Growth Factor, Epidermal Growth Factor 2, epidermal growth factor receptor, testostosterone, Epithelial Proliferating antigen, Epithelium Specific Antigen, c-MYC, HA.1, VSV-G Tag, Glu-Glu, EEEYMPME, Thioredoxine (trx), Epstein Barr virus and Epstein Barr Virus capsid antigen gp120, ERK (ERK1, ERK2, ERK3, pan ERK also called MAP kinase), Erythrocytes, Erythropoietin (EPO), Esterase, Estradiol, Estriol, Estrogen Receptor, Estrone, Ets-1 transcription, F1 antigen Yersina pestis, Factor 5, Factor VII, Factor VIII, Factor 9, Factor 10, Factor 11, Factor 12, Factor XIII, FAK (Focal Adhesion Kinase), FAS (CD95), FAS-L (CD178), Fascin, Fatty Acid Binding Protein, Ferritin, Fetal Hemoglobin, Fibrillin-1, Fibrinogen, Fibroblasts, Fibroblast Growth Factor, FGF-9, Fibronectin, Filamin, FKBP51, FKBP65, FK506, FLK1, flt-1 FLt-4 and FLT-3/FLK-2, FLT 3 Ligand, Fluorescein (FITC), FODRIN, Folate, Folate Binding Protein, fractalkine, frequenin, Frizzled, Fructose-6-p-kina, FSH, Fusin (CXCR4), GABA A and GABA B Receptor, Galectin, galanin, gastrin, GAP-43, G-CSF, G-CSF receptor, gelsolin, GIP (gastric inhibitory peptide), G0-protein (bovine), GDNF, GDNF-Receptor, Giardia intestinalis, Glial fibrillary acidic Protein, Glial filament protein, Glucagon/Glycentin, Glucose oxidase, Glucose 6 Phosphate Dehydrogenase, Gluco, Tranporter GLUT 1-4, GLUT 1-5, Glutamate Dehydrogenase, Glutamic Acid decarboxyla (GAD), Glutathione, Glyceraldehyde-3-phosphate dehydrogenase GAPDH, Glycerol-3-phosphate dehydrogenase, Glycerol kinase, glycine transporter (GLYT1, GLYT2), Glycogen Phosphoralase Isoenzyme BB (GPBB), Glycophorin A (CD235a), GM-CSF, C receptor alpha, Golgi Complex, Gonadotropin-Releasing Hormone Receptor (GnRHR), GP130, Granzyme, GRB2, GRB1, Green Fluorescent Protein (GFP), Growth Hormone, Growth Hormone Receptor, Growth Hormone Releasing factor, GRP78, Hantavirus, HCG, HDL (high density lipoprotein), Heat Shock Protein HSP-27, HeK 293 Host Cell Proteins, Helodermin, helospectin, Hemeoxygenase, Hemoglobin, Heparin, Hepatitis A, Hepatitis B Core Antigen, Hepatitis B virus surface antigen, Hepatitis C virus, Hepatistis E virus, Hepatitis G Virus, Hepatocyte Growth Factor, Heregulin (Neu differentiation factor/Neuregulin), Herpes Simplex Virus, Hexokinase, Histamine, His Tag, 6-His vector tags, HIV-1 p24, p55/17, gp41, gp120, tat, nef, rev, HIV reverse transcriptase, HLA Class I, HLA Class II, HLA-DM, HLA DQw1, HLA DRw 52, Peroxidase, HPV 16 Late I Protein, human free kappa light chains, human lambda light chains, Human IgA, human I heavy chain, human IgA1, human IgD, human IgE, human IgG heavy chain, human IgG1, human IgG3, human IgG4, human IgM, human IgM heavy chain, human J chain, human kappa lig, chains, human lambda light chains, Human Serum Amyloid P, Human Serum Amyloid P, Interleukin 1 beta converting enzyme, ICH-1 (caspase 2), Indian Hedgehog Protein (IHH), Influenza virus, Inhibin, Insulin, insulin like growth factor II, insulin growth factor binding protein 1, 2, 3, 4 or 5, insulin like growth factor, insulin like growth factor I receptor, insulin receptor, insulin/proinsulin, Interferon alpha, interferon alpha receptor, Interferon beta, Interferon gamma, interferon gamma receptor alpha and beta, Interleukin 1 alpha, Interleukin Receptor alpha type II, Interleukin 1-beta, Interleukin 10, interleukin 10 receptor, Interleukin 11, Interleukin 12, interleukin 12 receptor, Interleukin 13, Interleukin 15, Interleukin 16, Interleukin 17, Interleukin 18, Interleukin 2, Interleukin 2 receptor alpha, Interleukin receptor alpha chain (CD25), Interleukin 2 receptor beta, Interleukin 2 receptor beta chain(CD122), Interleukin 2 receptor gamma, Interleukin 3, Interleukin 3/interleukin 5/GM-CSF Receptor common chain, Interleukin 4, Interleukin 5, Interleukin 6, Interleukin 6 receptor alpha chain, Interleukin 7, Interleukin 7 receptor alpha, Interleukin 8, Interleukin 8 receptor, Interleukin 9, invertase, Involucrin, IP-10, Keratins, KGF, Ki67, KOR-SA3544, Kt3 epitope tag, lactate dehydrogenase, Lactoferrin, lactoperoxidase, Lamins, Laminin, La (SS-B), LCMV (Lymphocytic Choriomeningitis Virus), Legionella pneumophilia serotype, Legionella pneumophila LPS, Leptin and Leptin Receptor, Lewis A Antigen, LH (leutenizing Hormone), LHRH (leutenizing Hormone Releasing), L, (leukemia Inhibitory Factor), 5-Lipoxygenase, LPS Francesella tularensis, luciferase, Cancer Marker (MOC-1, MOC-21, MOC-32, Moc-52), Lymphocytes, lymphotactin, Lysozyme, M13, F1 Filamentous Phages, Macrophages/monocytes, Macrophage Scaveng, Receptor, Matrix metalloproteases, M-CSF, Major Basic Protein, malate dehyrogenase, Maltose Binding Protein, Mannose Receptor (macrophage), Mannose-6-phosphate receptor, MAP kinase antibodies (ERK, ERK, ERK2, ERK3), MASH1 (Mammalian achaete schute homolog 1 and 2), MCL-1, Mcm3, M, (MCAF), MCP-2, MCP-3, Melanocortin Receptors (1 through 5), Met (c-met), Mineralcortocoid Receptor (MR/MCR), Melanoma Associated Antigen, MGMT (methylguanine-DNA-methyltransferase), MHC Antibodies (incl. HLA DATA PACK), Milk F, Globule Membrane, Milk Mucin Core Antigen, MIP-1 alpha, MIP-1 beta, Mitochondrial markers, Mitosin, MMP-1, MM, MMP3, MMP7, MMP8, MMP-9 and MMP13 (matrix metalloproteases), MMP-14(MT1-MM, MMP15 (MT2-MMP), MMP16(MT3-MMP) and MMP19, Morphine, motili, Mucin related antibodies (Muc-1, muc-2, muc-3, muc-5ac), Mucin-6 glycoprotein, Mucin-like Glycoprotein, Mycobacterium tuberculosis, Myelin, Myelin Basic Protein, Myeloperoxidase, MyoD, Myoglobin, Myosin, Na+ Ca+ Exchanger Protein, Na+/K+/ATPase, Na+/K+/ATPa, NCAM (CD56), pan N-Cam, (neural cell adhesion marker), Nerve Growth Factor, Neu-Oncogene (c-erb B2), Neurofibrillary Tangle, Neurofilament 70+200 kD, Neurofilament 145 Kd, neurofilament 160 kd, Neurofilament 68 Kd, Neurofilament 200 kd, Neurofilament 200 kd, neurokin, A/substance K, neuromedin U-8 (NMU-8), Neuromodulin, neuronal pentraxin, Neuro-Specific Enolase, Neuropeptide Y (NPY), Neurophysin I (oxytocin precursor), Neurophysin, (vasopressin precursor), Neuropsin, Neurotensin, NFKB, Nicotinic Acetylcholine Receptor, (Beta2 and Alpha 4), NMDA receptors, N-MYC, Norepinephrine Transporter (NET), N, (Nitric Oxide Syntase) eNos, iNos, NT-3, NT, (neurotroph, 4), Nucleolar Helicase, Nucleolar Protein NO38, Nuclear Protein xNopp180, Nucleoplasm, Protein AND-1, Nucleolus Organizing Region (NOR), Nucleolin, occludin, Oncostatin M, ORC, Ornithine Decarboxylase, Ovalbumin, Ovarian Carcinoma, Oxytocin, P15, P16, P2, P27, P53 Oncoprotein, p62 Protein, p97 Atpase, membrane associated and cytosolic 42 kDa inositol (1,3,4,5) tetrakisphosphate receptor, PP44 Podocyte Protein (Synaptopodin), PAH (Polyaromatic Hydrocarbons), PACAP (pituitary adenylate cyclase activating peptide), Pancreas Polpeptide (PP), Pancreastatin, Pancreatic Islet Cell, papain, Papillomavirus (HPV), Parainfluenza type 2 viruses, Parathion, Parkin, PARP (Poly-A, Riobose Polymerase) PARP-1 and PARP-2, Patched-1, Patched-2, Paxillin, polychlorinated biphenyls, Pemphigus vulgaris (desmoglein 3), Penicillin, penicillinase, pep-carboxylase, pepsin, Peptide YY, Perforin and polyclonals, Perilipin, Peripherin, Perlecan, Petrole, Hydrocarbons (total), PPAR (peroxisome proliferation activated receptors), P-Glycoprotein (multi-drug resistance), PGP9.5, Phenanthrene, Phencyclidine (PCP), Phenylethanolamine, methyltransferase (PNMT), Phospholamban, Phospholipase A2, Phosphoserine, Phosphothreonine, Phosphotyrosine, Phosphothreonine-proline, phosphothreonine-lysi, phophotyrosi, Phosphotyrosine Kinase, Pichia pastoris, Placental Alkaline Phosphatase, Plakoglobin, Plakophilin 1, Plakophilin 2, Plakophilin 3, Plasminogen, Platelet Derived Growth Factor AA and BB and AB, Plectin, PM, ATPase (plasma membrane Ca pump), Pneumocystis carinii, Pneumolysin, Polychlorobiphenyl (PCB), PP 17/TIP47, PPAR (peroxisome proliferation activated receptors), Prednisone, Prednisolone, Pregnancy associated Plasma Protein A (PAPP-A), Pregnenolone, Prepro NPY 68–97, Presenilin-1, Presenilin-2, Prion protein, Progesterone, Progestero, Receptor, Prohibitin, Proinsulin, Prolactin, Proliferation Ce, Nuclear Antigen, Proline Transporter, Prostatic Acid Phosphatase (PAP), Prostatic Specif, Antigen (PSA), Proteasome 26S, Protein 4.1 M ascites, Protein G, Protein Kinase C, Pseudomonas mallei, PTH, Pulmonary Surfactant Associated Proteins, Puromycin, Pyruva, kinase, Rabies Virus, RAC-1 and Rac-2, RAGE (receptor for AGE), RANTES, RDX, RecA, Receptor for advanced glycation end products (RAGE), Red Blood cells, Regulatory subunit, RELM alpha and Beta (resistin like molecules), Renin, Rennin, Replication Protein A (RPA p32 and p70), Resistin, Respiratory syncytial virus (RSV), Retinoblastoma (Rb), phosphospecific RB (ser780), Ribonuclease A, RNA Polymera, Arna3, RNP (70 KdaU1), A Protein, B Protein, RO (RO52, Ro60), Rotavirus group specific antigen, Rubella virus structural glycoprotein E1, Ryanodine Receptor, S-100 Protein, saccharomyces cerevisiae, Salmonella O-antigens, Salmonel, typhimurium, Sarcosine Oxidase, SDF-1 Alpha and SDF-1 Beta, secretin, Selenoprotein P, Serotonin, Serotonin Receptor, Serotonin Transporter, Sex Hormone Binding Globulin (SHBG), SFRP5 (secreted frizzled-related protein 5), SF21 and SF9, SIV gp120, SIV p28, Smooth muscle actin, Somatostatin, Staphylococcus aureus, Staphylococcus aureus enterotoxin, STAT1, Stat2, Stat, Stat4, Stat5 Stat6, Stem Cell Factor (SCF) and SCFR/C-kit, Streptavidin, Streptococcus B, Stromal Cell Derived Factor-1 (SDF-1 alpha and beta), Substance P, Sufentanil AB, Superoxide Dismutase, Surfactant Associated Proteins (A,B,C,D), Symplekin, Synapsin I, Synapsin IIa, Synaptophysin, Synaptopodin (Podocyte Protein), Syndecan 1, Synphilin-1, Synuclein (alpha), SV40 Large T antigen and small T antigen, Talin, TARC, TAU, Taurine transporter, Tenascin, Testosterone, TGF-alpha, TGF-beta, TGF beta receptor (Endoglin), THC, Thomsen Friedenreich Antigen (TF), THY-1 25 kd Brain (CDw90), Thymocytes, Thrombin and Thrombin Receptor, Thyroglobulin (24TG/5E6 and 24Tg/5F9), Thyroid Binding Globulin, Thyroid Hormone Receptors, Thyroid Peroxidase, Thyroid Stimulating Hormone (TSH), Tyrosine Hydroxylase, Thyrotropin Releasing Hormone (TRH), Thyroxine (T4), TIe-1 and TIe-2, TIMP-1, TIMP-2, TIMP-3 (Tissue Inhibitors, metalloproteinase), Titin, TNF receptor associated factors 1 and 2, TNF Receptor, TNF receptor II, TNF-Alpha, TNF-Alpha, TNF-beta, Toxoplasma gondii p30 antigen, TPO (thrombopoietin), TRAF, Traf2,Traf3,TRAF4,TRAF5, TRAF6, Transferrin, Transferrin Receptor, Transforming Growth Factor A, Transformi, Growth Factor Beta, Transportin, Trepone, pallidium, Triiodothyronine (T3), Trinitrotoluene (TNT), TRK A, TRK B, TRK C, Tropon, (cardiac), Troponin I, Troponin T, trypsin, trypsin inhibitor, trypsinogen, TSH, TUB Gene, Tubulin alpha and beta, Tubulin beta specific, Tumor Marker related Antibodies, Tumor Necrosis Factor Alpha, Tyrosinase, Tweak, (caspase-4), Ubiquitin, Ubiquitin-L1, Uncoupling Proteins (UCP1, UCP2, UCP3, UCP 4 and UCP5), Urease, Uricase, Urocortin, Uroplakin, Vasopressin, Vasopressin Receptor, VEGF, Vesicular acetycholine transport, (VACht), Vesicular monoamine transporter (VMAT2), Villin, Vimentin, Vinculin, VIP (Vasoactive Intestinal Peptide), Vitamin B12, Vitamin B12, Vitamin D metabolites, Vitamin D3 Receptor, Von Willebrand Factor, VSV-G Epitope Tag, Wilm's tumor Protein X, Oxida, Yeast, hexokinase, SOD, cytochrome oxidase, carboxypeptidase, and Yersinia eterocolotica.

Alternatively, many of the substances noted above (e.g. folate, PGP, cytochrome P 450, and EGF) may in and of themselves be useful as targeting substances and may be incorporated into the particles of the present invention. In addition, other chemical compounds such as PEG may also be used for targeting and may be incorporated.

It is important to point out that in addition to targeting compounds per se, active compounds, functional excipients such as absorption enhancers, and other bioactive materials as gleaned from the lists of materials given herein can be incorporated in any of these localization sites.

In addition to the targeting of particles to specific sites for release of drug, as mentioned above particles incorporating certain radiopaque or optically dense materials could themselves be used for imaging, and when coupled to targeting compounds as described herein could target specific sites in the body and allow their visualization. As an example, somatostatin receptors are known to be localized at certain tumor sites, so that the attachment of a target to coated particles as per the instant invention that would bind selectively to somatostatin receptors could target a tumor and allow visualization via, e.g., x-ray, MR imaging, or radio-imaging. To extend this idea, a similarly targeted particle could then carry a radioactive material that would emit radiation intended to induce necrosis of the tumor.

Polymerized Liquid Crystals as Interior Phases.

U.S. Pat. No. 5,244,799 (the contents of which are hereby incorporated by reference in entirety) reports the polymerization of nanostructured cubic and hexagonal phase liquid crystals, with retention of their nanostructure. The retention of structure was demonstrated by small-angle x-ray scattering (SAXS) and transmission electron microscopy (TEM).

The possibility of polymerizing the cubic phase in the interior of a particle of the instant invention opens up a number of possibilities, particularly as relate to increasing the stability of the interior phase and modulating its interaction with the body, and cell membranes in particular. For an example of the latter, whereas an unpolymerized cubic phase might be expected to molecularly disperse when coming into contact with a biomembrane, polymerization of the same interior matrix might create a particle interior that would retain its integrity throughout its interaction with the same biomembrane, and this could have dramatic consequences as to the fate of the particle and to a drug inside the particle. Furthermore, the retention of a bilayer-bound drug (hydrophobic small molecule, membrane protein, etc.) might be increased tremendously by polymerization, yielding a slow-release particle. And the presence of a more permanent, precisely-defined pore structure, with precisely tunable poresize, might make possible improved controlled release of a drug, and/or sequestration of the drug from degradative or other enzymes by size-exclusion from the pores of the polymerized matrix.

The following examples illustrate the present invention but are not to be construed as limiting the invention.

EXAMPLES

In the following examples, Examples 14, 15, 16, and 34 demonstrate systems with coatings made of physically robust mineral materials, such as cupric ferrocyanide and calcium phosphate, that can provide for stability of the intact particles under stronger shear conditions, such as during pumping of a dispersion of the coated particles, for example, for recycling or transport. These minerals are also of low aqueous solubility, making them of potential interest in applications requiring release of the particle coating by strong shear, while at the same time protecting against release due to simple dilution with water. An example of such an application would be where a rodent deterrent such as capsaicin, or rodent toxin, would be encapsulated in the coated particles of the present invention, the particles impregnated into electrical wires, corrugated boxes, and other products requiring protection against pawing by rodents, and the pawing action of a rodent would induce release of the active deterrent or toxin. The low water solubility would prevent the deterrent from premature release due to damp conditions.

A robust organic material that provides a coating that is also of low aqueous solubility is ethylhydrocupreine, as, in examples 17 and 33, and this compound has the additional characteristic that it has an extremely bitter taste that could provide an additional deterrent effect in a rodent-deterrent application.

Examples 1, 2, 3, 6, 7, 8, 9, 10, 17, 18, 19, 20, 23 and 33 provide examples of coatings that are of low water solubility at neutral pH, but that increase substantially in solubility as the pH becomes either acidic or basic, depending on the compound. This can make the coated particles of importance in, for example, drug delivery, where a coating that releases preferentially in a particular pH range is desired, such as for intestinal release. Or such a coating could release, allowing the release of an antibacterial compound, at sites of bacterial activity, where pH is typically acidic. Or the release of the coating at a particular pH could allow the release of a pH stabilizing compound or a buffer system, for example in microparticles designed to control the pH of water in swimming pools.

Example 4 gives an example of particles with a coating, silver iodide, that could provide very useful properties as a cloud-seeding agent, since the silver iodide coating is well-known for cloud-seeding effectiveness, and the surface area and surface morphology afforded by the particle shape and size could amplify the effect of the silver iodide. This could be of commercial importance due to the expense of silver compounds, in which case the inexpensive liquid crystal interior could serve the role as a filler that would provide the same or greater seeding potential at a fraction of the cost of simple silver iodide. A similar increase in effectiveness due to amplification of surface area might prove of interest in the use of the particles as local anesthetics for mucous membranes, and the proper balance of lipids and active anesthetic hydrophobes (such as lidocaine) in the particle interior could be used to enhance the effect.

Example 5 demonstrates that compounds such as sulfides and oxides can be used as coatings in the coated particles of the present invention, even when they require gaseous reactants for formation. Such compounds are well-known for being not only high-stiffness materials, but also chemically extremely resistant, which could make such coated particles of interest in applications where the particles encounter harsh chemical and physical conditions, such as would be expected in use of the particles as polymer additives, or in processing involving high shear, such as impregnation of dye-containing particles in nonwoven materials, etc.

Examples 12 and 13 demonstrate the use of high water-solubility compounds as coatings, that can be of importance in applications requiring quick and convenient release of the coating by simple dilution with water. For instance, a spray system that would merge two streams, one containing the dispersion and the other water, could provide an aerosol in which the particle coating, useful for preventing agglomeration prior to spraying, would be dissolved after spraying when the particles were already aerosolized—in flight, so to speak. Since this dissolution could expose, for example, a nanostructured cubic phase interior that was very tacky, the particles could be used to adhere to, e.g., crops, or the bronchial lining, etc. The capsaicin loaded into the interior in Examples 12 and 13 would make this product of potential importance in providing rodent resistance after deposition of the tackv aerosolized particles onto crops, for example, since rodents are generally strongly repelled by the taste of capsaicin even at very low concentrations.

Examples 39 and 40 demonstrate the use of amorphous materials as exterior coatings for the particles of the present invention. Example 39 utilizes the amorphous polymer (PLGA), and Example 40 utilizes a small molecule (the sugar trehalose).

Examples 41 and 42 demonstrate variations in the processes used to create particles, and in particular they involve processes in which milling or particle size reduction are applied after formation of the coating material, in some cases in addition to sonication or microfluidization that is applied prior to coating material precipitation.

Examples 1 (part E), 27, 28 and 43 demonstrate the incorporation of active targets, including receptors, lectins, and antibodies, in particles according to the instant invention, and the retention of their binding capabilities.

All percentages in the following examples are weight percentages unless otherwise noted. The amounts of the components used in the following examples can be varied as desired, provided that the relative amounts remain as in the example: thus, these amounts can be scaled proportionately to the desired amount, recognizing of course that scaling up to large amounts will require larger equipment to process.

In the following examples, unless otherwise noted, the exterior coating of each coated particle comprises a non-lamellar material, and each interior core comprises a matrix consisting—essentially of at least one nanostructured liquid phase, at least one nanostructured liquid crystalline phase or a combination of at least one nanostructured liquid phase and at least one nanostructured liquid crystalline phase.

Example 1

This Example shows that a wide range of active compounds, including compounds of importance in pharmaceutics and biotechnology, can be incorporated into non-lamellar material-coated particles of the present invention.

An amount of 0.266 grains of sodium hydroxide was dissolved in 20 ml of glycerol using heating and stirring to aid in dissolution. An equimolar amount, namely 1.01 grams, of methyl paraben was then dissolved, again with heating. From this solution, 0.616 grams were taken out and mixed with 0.436 grams of lecithin and 0.173 grams of oleyl alcohol in a test tube. The active ingredient (or agent) identified below was incorporated at this point and the solution thoroughly mixed to form a nanostructured liquid crystalline phase material with an active ingredient disposed within it. An "upper solution", which was obtained by dissolving 0.062 grams of Pluronic F-68 (a polvpropyleneoxide-polvethyleneoxide block copolymer surfactant commercially available from BASF), and 0.0132 grams of acetic acid together and adding to the test tube as a layer of solution above the previous solution that included the active agent. Immediately the test tube containing the liquid crystalline mixture and the upper solution was shaken vigorously and sonicated for three hours in a small, table-top ultrasonicator (Model FS6, manufactured by Fisher Scientific). The resulting dispersion showed a high loading of particles coated with methyl paraben with size on the order of one micron upon examination with an optical microscope.

Example 1 A 2.0 wt % of salicylic acid (based on the weight of the internal core of liquid crystalline phase material) was incorporated as an active agent.

Example 1B 2.0 wt % Vinblastine sulfate (based on the weight of the internal core of liquid crystalline phase material) was incorporated as an active agent.

Example 1 C 2.4 wt % Thymidine (based on the weight of the internal core of liquid crystalline phase material) was incorporated as an active agent.

Example 1 D 1.6 wt % Thyrotropic hormone (based on the weight of the internal core of liquid crystalline phase material) was incorporated as an active agent.

Example 1 E 2.9 wt % Anti 3', 5'cyclic AMP antibody (based on the weight of the internal core of liquid crystalline phase material) was incorporated as an active agent.

Example 1 F 2.0 wt % L-Thyroxine (based on the weight of the internal core of liquid crystalline phase material) was incorporated as an active.

Particles such as these with a coating which increases substantially in solubility as the pH increases, could be useful in drug delivery, where the increase in pH moving along the gastrointestinal tract from the stomach to the intestines could result in effective delivery to the lower gastrointestinal tract, giving rise to a more uniform delivery rate over time.

Example 2

This example demonstrates the long-term stability of a dispersion of particles of the present invention.

The amino acid D, L-leucine, in the amount of 0.132 grams, was dissolved in 2.514 grams of 1 M hydrochloric acid, resulting in the formation of leucine hydrochloride in solution. The solution was dried on a hot plate under flow of air, but was not allowed to dry to complete dryness: drying was stopped when the weight reached 0.1666 gram, which corresponds to one molar equivalent addition of HCl to the leucine. An amount of 0.130 grams of this compound were added to 0.879 grams of a nanostructured reverse bicontinuous cubic phase material prepared by mixing sunflower oil monoglycerides and water, centrifuging, and removing the excess water. An upper solution was prepared by mixing 1.0 grams of 1 M sodium hydroxide with 3 grams of water. All water used was triply-distilled. The upper solution was overlaid on the cubic phase, the test tube sealed and sonicated, resulting in the formation of a milky-white dispersion of microparticles coated with leucine.

A similar dispersion was prepared with the use of Pluronic F-68 as stabilizer. An amount of 0.152 grams of leucine hydrochloride was added to 0.852 grams of nanostructured reverse bicontinuous cubic phase material as above, and an upper phase consisting of 0.08 grams of F-68, 1.0 gram of 1 M sodium hydroxide, and 3.0 grams of water was overlaid on the nanostrucrured reverse bicontinuous cubic phase material and sonicated. Again, a milky-white dispersion of leucine-coated microparticles was formed, where this time the F-68 amphiphilic block copolymer surfactant coated the outer (leucine-based) surface of the particles.

As a control experiment to show the necessity of the leucine for the formation of crystalcoated panicles, 1.107 grams of Dimodan LS (hereinafter "sunflower monoglycerides) were mixed with 1.000 gram of water to form a nanostructured reverse bicontinuous cubic phase material. An upper solution was prepared by adding 0.08 grams of Pluronic F-68 to 4.00 grams of water. As per the same procedure used to make the dispersions above using leucine, the upper solution was overlaid on the nanostructured reverse bicontinuous cubic phase material and the test tube sealed and sonicated. In this case, essentially no microparticles were formed: the nanostructured reverse bicontinuous cubic phase material remained as large, macroscopic chunks even after several hours of sonication under the same conditions as the leucine experiment.

This dispersion of the coated particles of the present invention was examined regularly for a period of twelve months and did not show signs of irreversible flocculation. With even slight agitation, it showed no signs of irreversible flocculation over time scales of weeks. In the absence of agitation, it did show signs of flocculation, but upon mild shaking for 5 seconds or more, any flocculation reversed. A droplet of the dispersion was examined in an Edge Scientific R400 3-D) microscope at 1,000 magnification (100× objective, oil immersion, transmitted light) and shown to have a very high loading of submicron particles.

Particles such as these, with relatively weak organic coatings, can be used, for example, in acne creams, where an active material such as triclosan could be incorporated and the shear associated with applying the material to the skin would release the coating.

Example 3

In this example paclitaxel was incorporated at the level of 0.5% of the internal core. The particle coating was leucine, which in other examples herein has been shown to provide longterm stability.

A paclitaxel-containing nanostructured reverse bicontinuous cubic phase material was produced by mixing 4 mg of paclitaxel, dissolved in 2 ml t-butanol, in a nanostructured reverse bicontinuous cubic phase material containing 0.280 gm lecithin, 0.091 gm of oleyl alcohol, and 0.390 am glycerol: after evaporation of the butanol under argon, a nanostructured reverse bicontinuous cubic phase material formed that was viscous and optically isotropic. The sample was centrifuged for one hour, during which time no precipitate appeared. Optical isotropy was verified in a polarizing optical microscope. A leucine hydrochloride solution in glycerol was produced by mixing 0.241 grams of leucine, 2.573 grams of 1 M HCl, and 0.970 grams of glycerol, after which the water and excess HCl were evaporated under air flow on a 50° C. hot plate, drying for three hours. Next, 0.882 grams of this leucine-HCl in glycerol solution were added to the nanostructured reverse bicontinuous cubic phase material. The upper solution was then prepared by adding 0.102 grams of Pluronic F-68 to 4.42 grams of an aqueous buffer at pH 5.0. After overlaying the upper solution onto the nanostructured reverse bicontinuous cubic phase material, the nanostructured reverse bicontinuous cubic phase material was dispersed into microparticles by sonicating for 2 hours.

Particles such as these could be used for the controlled release of the antineoplastic agent paclitaxel.

Example 4

In this example, the coating was silver iodide, which has the potential to make the particles useful in photographic processes. Silver iodide is somewhat unusual in that, even though it is a simple salt (with monovalent ions only), it has a very low solubility in water. A nanostructured reverse bicontinuous cubic phase material was prepared by mixing 0.509 grams of Dimodan LS (commercially available as from Grinstedt AB and referred to herein as "sunflower monoglycerides"), 0.563 grams of triply-distilled water, and 0.060 grams of sodium iodide. An upper solution was prepared by adding 0.220 grams of silver nitrate, 0.094 grams of Pluronic F-68, and 0.008 grams of cetylpyridinium chloride to 3.01 grams of water. A dispersion of microparticles was then produced by overlaying the upper solution onto the nanostructured reverse bicontinuous cubic phase material and sonicating for one hour. The particle coating was silver iodide, which has a low solubility in water.

Example 5

In this example cadmium sulfide was used as the coating. It is a nonlamellar crystalline compound that exhibits large changes in physical properties when doped with small amounts of other ions. This example also demonstrates that a gas, such as hydrogen sulfide gas, can be used in the present invention to induce crystallization and particle formation.

A nanostructured reverse bicontinuous cubic phase material was prepared by thoroughly mixing 0.641 grams of Dimodan LS with 0.412 grams of water, and to this was added 0.058 grams of cadmium sulfate hydrate. After this, 0.039 grams of calcium sulfide was overlaid on the mixture, and the test tube was purged with argon gas and capped. An upper solution was prepared by adding 0.088 grams of Pluronic F-68 and 1.53 grams of glycerol to 1.51 grams of 1 M HCl and then sparging the solution with argon. The upper solution was taken up in a syringe, and added to the first test tube. Upon addition, the smell of hydrogen sulfide gas could be detected in the test tube, as well as the formation of a yellowish precipitate: this indicated the action of hydrogen sulfide gas in producing cadmium sulfide (CdS) from the cadmium sulfate. The system was sonicated, resulting in a dispersion of microparticles which had a cadmium sulfide coating.

Example 6

This example demonstrates that the interior is substantially protected from contact with conditions outside the particle by the crystalline coating, which here is leucine. Any contact with zinc dust chances methylene blue to colorless in less than one second; here, addition of zinc did not cause a loss of color for some 24 hours. Although there was an eventual loss of color, that loss is believed to be due simply to the effect of the zinc on the leucine coating.

A solution of leucine hydrochloride in water was made by mixing 0.122 grams of leucine with 1.179 grams of 1M HCl and evaporating until approximately 1 gram of solution remained. To this was added 0.922 grams of sunflower monoglycerides, and 10 drops of a strongly colored aqueous solution of methylene blue. An upper solution was produced by adding 0.497 grams of 1M NaOH and 0.037 grams of Pluronic F-68 to 3.00 grams of pH 5 buffer. The upper solution was overlaid, the system sonicated, and a dispersion of microparticles formed. An aliquot of the dispersion was filtered to remove any undispersed liquid crystal, and 0.1 grams of 100 mesh zinc dust added. (When zinc dust is shaken with a solution of methylene blue, the reducing effect of the zinc removes the blue color, normally in a matter of a second, or almost instantaneously.) However, in the case of the microencapsulated methylene blue produced by this process, it took on the order of 24 hours for the color to disappear, finally resulting in a white dispersion. Thus, despite interactions between the zinc and the leucine that can disrupt the coatings of these particles, the coatings provided substantial protection of the methylene blue against the effect of the zinc, increasing the time required for zinc reduction of the dye some 4–5 orders of magnitude.

If particles such as these are employed in a product in which two active ingredients must be sequestered from contact with each other (such as the oxidation-sensitive antibacterial compound triclosan and the strongly oxidizing cleansing agent benzoyl peroxide), this experiment demonstrates the feasibility of using leucine-coated particles in preventing contact between an encapsulated compound and the environment outside the particle.

Example 7

In this example a leucine coating protects the methylene blue dye in the particle interior from contact with ferrous chloride, as easily seen by the absence of the expected color change when ferrous chloride is added to the dispersion. This indicated that the coating was substantially impermeable even to ions.

A solution of leucine hydrochloride in glycerol was made by mixing 0.242 grams of leucine, 2.60 grams of 1M HCl, and 1.04 grams of glycerol, and then drying on a 50° C. hot plate under flow of air for 1.5 hours. A nanostructured reverse bicontinuous cubic phase material was prepared by mixing this leucine-HCl solution, 0.291 agams of lecithin (Epikuron 200, from Lucas-Meyer), 0.116 grams of oleyl alcohol, and 0.873 grams of glvcerol; this was colored by the addition of a pinch of methylene blue. An upper solution was prepared by adding 0.042 grams of Pluronic F-68 surfactant to 4.36 grams of pH 5 buffer, overlaid on the nanostructured reverse bicontinuous cubic phase material, and the system sonicated to produce a dispersion of microparticles. To an aliquot of this dispersion was added 0.19 grams of ferrous chloride, a reducing agent. The absence of a color change indicated that the methylene blue was protected against contact with the ferrous compound by encapsulation in the leucine-coated particles, since the addition of ferrous chloride to methylene blue solutions normally changes the color to blue-green (turquoise).

Similarly to Example 6, this experiment shows that encapsulated compounds such as methylene blue which are sensitive to, in this case, reducing agents, can be protected against reducing conditions outside the particle until release of the coating. This could be useful in, for example, electrochemical applications where the effect of application of electrical current would be gated by the chemical release of the coating.

Example 8

This example, when considered along with Example IA and Example 10, demonstrates that particles of the present invention coated with methyl paraben can be produced in two entirely different ways: either by a thermal process, such as a heating-cooling method, or by a chemical reaction, such as an acid-base method.

To a nanostructured reverse bicontinuous cubic phase material, produced by mixing 0.426 grams of sunflower monoglycerides (Dimodan LS) with 0.206 grams of acidic water at pH 3, were added 0.051 grams of methyl paraben and a trace of methylene blue dye. The mixture was heated to 110° C., shaken and put on a vibro-mixer, and plunged into 23° C. water for 5 minutes. Two milliliters of a 2% Pluronic F-68 solution, acidified to pH 3 with HCl were overlaid, the test tube scaled with a twist cap, and the tube shaken and then sonicated for minutes. This produced a dispersion of microparticles coated with methylparaben.

Since this experiment alone with Example 10 demonstrate that particles coated with the same compound,n this case methyl paraben, can be produced either by a thermal method or by a chemical precipitation method, this provides an extra degree of versatility which can be important in optimizing production efficiency and minimizing costs, for example in large-scale pharmaceutical production of microencapsulated drugs.

Example 9

The nanostructured reverse bicontinuous cubic phase material in this example is based on nonionic surfactants, which are generally approved for drug formulation, and which yield liquid crystalline phase materials with properties tunable by small temperature changes. For example, in an acne cream this could be used to achieve detergent (cleansing) properties at the temperature of application, but insolubility at the temperature of formulation. Furthermore, since it is based on a tuned mixture of two surfactants, and since the phase and properties thereof depend sensitively on the ratio of the two surfactants, this provides a convenient and powerful means to control the properties of the internal core. In addition, this example resulted in a transparent dispersion. This is noteworthy because even a small fraction of particles with a size larger than about 0.5 microns gives rise to an opaque dispersion.

A nanostructured reverse bicontinuous cubic phase material was prepared by mixing 0.276 grams of "OE2" (an ethoxylated alcohol surfactant commercially available as "Ameroxol OE-2", supplied by Amerchol, a division of CPC International, Inc.) with 0.238 grams of "OE5" (an ethoxylated alcohol surfactant commercially available as "Ameroxol OE-2", supplied by Amerchol, a division of CPC International, Inc.), and adding 0.250 grams of water (includes excess water). To this was added 0.054 grams of methyl paraben and a trace of methylene blue dye. The mixture was heated to 110° C., shaken and put on a vibro-mixer, and plunged into 23 C water for 5 minutes. Two milliliters of a 2% Pluronic F-68 solution, acidified to pH 3 with HCl, were overlaid, the test tube sealed with a twist cap, and the tube shaken and then sonicated for 30 minutes. This produced a dispersion of microparticles coated with methylparaben. Interestingly, the sub-micron size of the particles resulted in a transparent dispersion.

Example 10

This example shows that methyl paraben-coated particles can be created by a heating-cooling process, in addition to the acid-base method of the previous example. This example also demonstrates that a mixture of two phases can be dispersed.

Lecithin (Epikuron 200, 0.418 grams) was mixed with 0.234 grams of oleyl alcohol and 0.461 grams of acidic water at pH 3, resulting in a mixture of nanostructured reverse bicontinuous cubic phase material and nanostructured reversed hexagonal phase material. Out of this was taken 0.50 grams, to which were added 0.049 grams of methyl paraben, and mixed well. This was heated to 120° C., stirred while hot, then reheated to 120° C. The test tube was removed from the oven, and the test tube plunged into cold water for 5 minutes. After this the twist-cap was taken off, two milliliters of a 2% Pluronic F-68 solution, acidified to pH 3 with HCl, were overlaid, and the sample stirred, shaken, and finally sonicated. This resulted in a milky-white dispersion of microparticles coated with methyl paraben. Examination in an optical microscope showed microparticles with sizes in the range of 2–10 microns. Excess methyl paraben crystalline material was also seen.

This example demonstrates that a mixture of two co-existing nanostructured phases can provide the interior of the microparticles. This could be important in, for example, controlled-release drug delivery, where a mixture of two phases, each loaded with drug, could be used to achieve a desired pharmacokinetics: for example, with a mixture of a reversed hexagonal phase and a cubic phase, the release from these two phases follows different kinetics, due to the different geometry of the porespaces, and the resulting kinetics would be a combination of these two profiles.

Example 11

This example shows that water-free particle interiors can be produced, such as for protection of water-sensitive compounds.

The same procedure used in the preparation of Example 10 was used, but the water was replaced by glycerol (which was present in excess) in the preparation of the nanostructured bicontinuous reversed cubic phase liquid crystalline material. The amounts were: lecithin 0.418 grams, oleyl alcohol 0.152 grams, glycerol 0.458 grams, and methyl paraben 0.052 grams. The result was a milky-white dispersion of microparticles coated with methyl paraben.

The protection of water-sensitive active compounds is important in, for example, oral health care products incorporating actives that are hydrolytically unstable.

Example 12

In this example capsaicin was incorporated in particles coated with potassium nitrate, and where the nanostructured reverse bicontinuous cubic phase material is based on extremely inexpensive surfactants. The coating is easily removed by simply adding water—such as in a crop-spraying gun which merges a stream of the dispersion with a stream of water, as it aerosolizes the liquid into droplets. Note that the potassium nitrate would serve a dual purpose as a fertilizer.

The nonionic surfactants "OE2" (0.597 grams) and "OE5"(0.402 grams) were mixed with 0.624 grams of water which had been saturated with potassium nitrate. To this mixture the active compound capsaicin (in pure crystalline form, obtained from Snyder Seed Corporation) was added in the amount of 0.045 grams. Next, 0.552 grams of this mixture were removed, 0.135 grams of potassium nitrate were added, and the complete mixture heated to 80° C. for 5 minutes. An upper solution was prepared by taking a 2% aqueous solution of Pluronic F-68 and saturating it with potassium nitrate. The melted mixture was shaken to mix it, then put back in the 80° C. oven for 2 minutes. The test tube was the plunged in 20° C. water for 5 minutes, at which point the upper solution was overlaid, and the entire mix stirred with a spatula, capped, shaken, and sonicated. The result was a dispersion of microparticles coated with potassium nitrate, and containing the active ingredient capsaicin in the interior.

When the dispersion was diluted with an equal volume of water, the coating was dissolved (in accordance with the high solubility of potassium nitrate in water at room temperature), and this was manifested as a rapid coagulation and fusion of the particles into large clumps. The interior of each particle was a tacky liquid crystal, so that in the absence of a coating, flocculation and fusion occur.

The example that we discuss here is that of a spray that would be used on decorative plants and/or agricultural crops, and would deter animals from eating the leaves. We have succeeded in encapsulating the compound capsaicin, which is a non-toxic compound (found in red peppers and paprika) that causes a burning sensation in the mouth at concentrations in the range of a few parts per million. Capsaicin has a record of commercial use as a deterrent to rodents and other animals.

Pure capsaicin was encapsulated in the cubic phase interior of particles having a coating of crystalline potassium nitrate—saltpeter. The exterior solution outside the particles was a saturated aqueous solution of potassium nitrate, which prevents dissolution of the coating until it is diluted; a dilution of the dispersion with water by approximately 1:1 resulted in nearly complete dissolution of the particle coatings. (This dissolution was captured on videotape and, on viewing the tape, it was clear that there was dissolution of the coating and subsequent fusing of the particle interiors.)

Upon dilution and subsequent dissolution of the coating, the interior of the particle was exposed, this being a cubic phase with the following crucial properties:

A) it was insoluble in water;

B) it was extremely tacky, adhesive; and

C) it has very high viscosity.

Together these three properties imply that the de-coated cubic phase particles should adhere to plant leaves, and property A means that it will not dissolve even when rained on.

The same three properties were also crucial to the success of animal tests of the bulk cubic phase, used as a controlled-release paste, in the delivery of photodynamic therapy (PDT) pharmaceutical agents for the treatment of oral cancer.

The concentration of capsaicin achieved in the cubic phase particles was two orders of magnitude higher than in pharmaceutical preparations used in the treatment of arthritis. Higher loadings, perhaps as high as 20%, may be possible.

From the standpoint of commercialization, the components in the dispersion are extremely inexpensive, and all are approved for use in foods, for topical application, and the like. In addition, potassium nitrate is a well-known fertilizer.

Example 13

This example used capsaicin/potassium nitrate as in the previous example, but here the nanostructured reverse bicontinuous cubic phase material is based on lecithin, which is an essential compound in plant and animal life, and can be obtained cheaply. This nanostructured reverse bicontinuous cubic phase material is also stable over a wide temperature range, at least to 40° C. as might be encountered under normal weather conditions.

Soy lecithin (Epikuron 200), in the amount of 1.150 grams, was mixed with 0.300 grams of oleyl alcohol, 1.236 grams of glycerol, and 0.407 grams of potassium nitrate. The active capsaicin was added to this in the amount of 0.150 grams, and the mixture thoroughly mixed. Next, 0.50 grams of potassium nitrate were added, and the complete mixture heated to 120° C. for 5 minutes. An upper solution was prepared by taking a 2% aqueous solution of Pluronic F-68 and saturating it with potassium nitrate. The melted mixture was stirred, then put back in the 120° C. oven for 3 minutes. The test tube was the plunged in cold water for 5 minutes, at which point the upper solution was overlaid, and the entire mix stirred with a spatula, capped, shaken, and sonicated, then alternated between shaking and sonicating for 30 cycles. The result was a dispersion of microparticles coated with potassium nitrate, and containing the active ingredient capsaicin in the interior at a level of approximately 5%. Also present were crystals of excess potassium nitrate.

The applications are similar to those of Example 12, except that the use of lecithin in the interior could provide for better integration of the particle interior with the plant cell membranes, possibly yielding better delivery.

Example 14

In this example cupric ferrocyanide-coated particles were shown to be resistant to shear.

A nanostructured reverse bicontinuous cubic phase material was prepared by mixing 0.296 grams of sunflower monoglycerides (Dimodan LS) with 0.263 grams of a 10% aqueous solution of potassium ferrocyanide. An upper solution was prepared by adding 0.021 grams of cupric sulfate and 0.063 grams of Pluronic F-68 to 4.44 grams of water. The upper solution was overlaid onto the nanostructured reverse bicontinuous cubic phase material, the test tube sealed with a twist cap, and the system sonicated for 45 minutes. The result was a high concentration of microparticles, coated with cupric ferrocyanide, and with diameters on the order of 3 microns. This process produces microparticles without requiring temperature excursions, except those associated with sonicating, and these can be circumvented by using another form of emulsification. Furthermore, no excursions in pH were required.

When a droplet was placed between microscope slide and cover slip for microscopic examination, it was found that the cupric ferrocyanide-coated particles were fairly resistant to shear; when the cover slip was massaged over the dispersion, light pressure with the fingers did not induce any noticeable loss of shape or fusion of the particles. This was in contrast with, for example, particles coated with magnesium carbonate hydroxide, where light pressure induced a high degree of shape loss and fusing of particles. These observations were in accordance with the high stiffness of cupric ferrocyanide.

Particles with coatings resistant to shear could be important in applications requiring pumping of the particles, where traditional polymer-coated particles are known to suffer lifetime limitations due to degradation of the coating with shear.

Example 15

In this example capsaicin was incorporated at a fairly high loading, namely 9 wt %, into the interiors of crystal-coated particles of the present invention. A nanostructured reversed bicontinuous cubic phase was produced by mixing 0.329 grams of lecithin, 0.109 grams oleyl alcohol, 0.611 grams glycerol, and 0.105 grams of capsaicin (obtained in crystalline form as a gift from Snyder Seed Corp., Buffalo, N.Y.). To this cubic phase were added 0.046 grams of cupric sulfate. An upper solution was prepared by mixing 0.563 grams of 10% potassium ferrocyanide aqueous solution with 2.54 grams of water. The upper solution was overlaid onto the cubic phase-cupric sulfate mixture, and the tube sonicated for two hours. The reaction that forms cupric ferrocyanide was easily evidenced by the deep reddish-brown color of the compound. At the end of this time, the cubic phase was dispersed into cupric ferrocyanide-coated particles. The coating was made of cupric ferrocyanide, which is a strong material and has some selective permeability to sulfate ions. Since this coating material is a robust crystal, as seen from Example 14, and capsaicin is extremely unpleasant to the taste of rodents, these particles could be useful as rodent deterrents in preventing damage to corrugated boxes, agricultural plants, etc., particularly where the particles must be resistant to mild shear (as during production of the particle-laced boxes, or deposition of the particles onto plants), prior to the gnawing action of rodents which would open the microparticles and expose the capsaicin to the animal's tastebuds.

Example 16

In this example microparticles with a cupric ferrocyanide coating were produced using the same procedure as in Example 14, but in this case an antibody was incorporated as the active agent. In particular, anti 3', 5' cyclic adenosine monophosphate (AMP) antibody was incorporated as an active agent at a loading of 1 wt % of the interior. A cubic phase was prepared by mixing 0.501 grams of sunflower monoglycerides with 0.523 grams of water. Potassium ferrocyanide, in the amount of 0.048 grams, was added to the cubic phase, together with approximately 0.010 grams of the antibody. Excess aqueous solution was removed after centrifuging. An upper solution was prepared by adding 0.032 grams of cupric nitrate and 0.06 grams of Pluronic F-68 to 3.0 grams of water. After overlaying the upper solution and sonicating, a milky-white dispersion of microparticles, coated with cupric ferrocyanide, was obtained. Such particles could be useful in a biotechnology setting such as a bioreactor, in which the stiff cupric ferrocyanide coating would be useful in limiting release during mild shear conditions encountered (for example, in a pressurized inlet), prior to the desired release of coating and availability of the bioreactive antibody.

Example 17

In this example ethylhydrocupreine forms an extremely hard shell. In this example an acid-base process was used.

A nanostructured reverse bicontinuous cubic phase material was prepared by mixing 0.648 grams of sunflower monoglycerides (Dimodan LS) with 0.704 grams of water. To this were added 0.084 grams of ethylhydrocupreine hydrochloride, and a trace of methylene blue. An upper solution was prepared by adding 1.01 grams of 0.1M sodium hydroxide and 0.052 grams of Pluronic F-68 to 3.0 grams of water. After overlaying the upper solution onto the liquid crystal, the system was sonicated, resulting in a dispersion of microparticles coated with ethylhydrocupreine (free base). Most of the particles were less than a micron in size, when examined with optical microscopy.

Particles which maintain integrity with dessication could be useful in, for example, slow-release of agricultural actives (herbicides, pheromones, pesticides, etc.), where dry weather conditions could cause premature release of less resistant particles.

Example 18

In this example leucine-coated particles were created by a heating-cooling protocol.

A nanostructured reverse bicontinuous cubic phase material was prepared by mixing 1.51 grams of sunflower monoglycerides (Dimodan LS) with 0.723 grams of water. To 0.52 grams of the nanostructured reverse bicontinuous cubic phase material taken from this mixture were added 0.048 grams of DL-leucine. The mixture was stirred well and heated to 80° C., then cooled to room temperature by plunging in water. Immediately a 2% solution of Pluronic F-68 in water was overlaid, the mixture shaken, and then sonicated. This resulted in a milky dispersion of microparticles coated with leucine.

The ability to make the same coating (in this case leucine) by either a thermal method or an acid-base method provides important flexibility in production, since, for example, certain actives (proteins, for example) are very easily denatured with temperature but can be quite resistant to pH, whereas other compounds can be resistant to temperature but can hydrolyze at acidic or basic pH.

Example 19

This example shows that interior components can be protected from contact with oxygen, even when oxygen was bubbled into the exterior medium (here water).

A nanostructured reverse bicontinuous cubic phase material (with excess water) was prepared by mixing 2.542 grams of sunflower monoglycerides with 2.667 grams of water. From this, 0.60 grams of nanostructured reverse bicontinuous cubic phase material were removed. Next, 0.037 grams of DL-leucine and 0.497 grams of 1M HCl were mixed and dried, after which 0.102 grams of water were added, to yield a solution of leucine hydrochloride, which was added to the 0.60 grams of nanostructured reverse bicontinuous cubic phase material, along with a trace of methyl red dye. The nanostructured reverse bicontinuous cubic phase material was a strong yellow color, but when spread out as a film it turned crimson-red in about 3 minutes, due to oxidation. An upper solution was prepared by mixing 0.511 grams of 1M sodium hydroxide, 0.013 grams of Pluronic F-68, and 2.435 of water. A dispersion of leucine-coated, methyl red-containing microparticles was prepared by overlaying the upper solution onto the liquid crystal and sonicating. It was first checked that a solution of methyl red in water, with or without F-68 added, quickly changes from yellow to crimson-red when air was bubbled through. Then, when air was bubbled through the dispersion of methyl red-containing microparticles, it was found that the color did not change from yellow, thus demonstrating that the encapsulation of the methyl red inside the microparticles protected the methyl red against oxidation.

Particles such as these which are able to protect the active compound from contact with oxygen could be useful in protecting oxygen-sensitive compounds, such as iron dietary supplements for example, during long storage.

Example 20

In this example the water substitute glycerol was used both in the interior nanostructured reverse bicontinuous cubic phase material, and as the exterior (continuous) coating, thus substantially excluding water from the dispersion.

A dispersion of microparticles was prepared using glycerol instead of water, by mixing soy lecithin and oleyl alcohol in the ratio 2.4:1, then adding excess glycerol and mixing and centrifuging. An amount of 0.70 grams of this nanostructured reverse bicontinuous cubic phase material was mixed with 0.081 grams of methyl paraben. An upper solution was prepared by adding cetylpyridinium bromide to glycerol at the level of 2%. The nanostructured reverse bicontinuous cubic phase material-methyl paraben mixture was sealed and heated to 120° C., mixed well, reheated to 120° C., and then plunged into cold water, at which point the upper solution was overlaid and the test tube re-sealed (with a twist-cap) and sonicated. This resulted in microparticles, coated with methyl paraben, in a glycerol continuous phase. Such a glycerol-based dispersion is of interest in the microencapsulation of water-sensitive actives.

Using microparticle dispersions such as these, hydrolytically unstable actives, which are encountered in a wide range of applications, can be protected against contact with water even after release of the coating.

Example 21

Similar to Example 6 above, where zinc is used to challenge encapsulated methylene blue, but here the coating is potassium nitrate. In addition, the same dispersion is also subjected to challenge by potassium dichromate.

A nanostructured reverse bicontinuous cubic phase material was prepared by mixing 0.667 grams of soy lecithin, 0.343 grams of oleyl alcohol, 0.738 grams of glycerol, and a trace of methylene blue. To 0.469 grams of the equilibrated phase was added 0.225 grams of potassium nitrate. An upper solution was prepared by adding 2% Pluronic F-68 to a saturated aqueous solution of potassium nitrate. This was overlaid onto the liquid crystal, and the system sonicated until the liquid crystal was dispersed into microparticles, coated with potassium nitrate. The color of the dispersion was light blue. Two tests were then used to show that the methylene blue was protected by encapsulation in the microparticles. To approximately 1 ml of this dispersion was added approximately 0.1 grams of finely powdered zinc; when powdered zinc contacts methylene blue in solution, it causes a loss of color. After shaking, the mixture was centrifuged very briefly, with about 10 seconds total time loading into the centrifuge, centrifuging, and removing from the centrifuge; this was done to avoid interference from the zinc in determining the color of the methylene blue-containing particles. It was found that there was very little, if any, decrease in blue color from the treatment with zinc, showing that the microparticle coating protected the methylene blue from contact with the zinc. Then, potassium dichromate was added to another aliquot of the original light-blue dispersion. This changed the color to a greenish color, with no hint of the purplish-brown that results if methylene blue in solution were contacted with potassium dichromate.

Coated particles of this Example feature an extremely cost-effective coating material, potassium nitrate, and yet protect active compounds against chemical degradation from outside conditions, making them of potential importance in, for example, agricultural slow-release.

Example 22

This provides an example of microparticles with a permselective coating of a inclusion compound. This particular inclusion compound, a so-called Werner complex, has the property that the porosity remains when the guest molecule is removed. Clathrate and inclusion compound coatings are of interest as coatings of selective porosity, where selectivity for release or absorption can be based on molecular size, shape, and/or polarity.

A nanostructured reverse bicontinuous cubic phase material was first prepared by mixing 0.525 grams of sunflower monoglycerides and 0.400 grams of water. To this were added 0.039 grams of manganese chloride ($MnCl_2$) and 0.032 grams of sodium thiocyanate. An upper solution was prepared by adding 0.147 grams of 4-picoline (4-methylpyridine) to 3.0 ml of a 2% aqueous solution of Pluronic F-68. The upper solution was overlaid on the liquid crystal mixture, and the test tube sealed and sonicated. The nanostructured reverse bicontinuous cubic phase material was thus dispersed into microparticles coated with the manganese form of the Werner complex, namely $Mn(NCS)_2(4-MePy)_4$.

The coating in this example may find use in the removal of heavy metals from industrial streams. In this case the coating can be a porous crystal—known as a clathrate—which permits atomic ions to pass across the coating and into the cubic phase interior, which is an extremely high-capacity absorbent for ions due to the high surface charge density (using an anionic surfactant, or more selective chelating groups such as bipyridinium groups, etc.). Most likely permanent pores would be the best. The selectivity afforded by the clathrate coating circumvents the reduction in sorbent power that is inevitable with traditional sorbents (such as activated carbon and macroreticular polymers), due to larger compounds that compete with the target heavy metal ions for the available adsorption sites. Regeneration of the sorbent could be by ion-exchange, while keeping the particles and coatings intact (this latter step would, incidently, be an example of release).

Example 23

In this example coated particles with an outer coating comprising methyl paraben and having a special dye disposed in the nanostructured reverse bicontinuous cubic phase material were challenged with a cyanide compound, which would cause a color change in the event of contact with the dye. Since the cyanide ion is extremely small, the success of this test shows that the coating is impervious even to very small ions.

A nanostructured reverse bicontinuous cubic phase material was prepared by mixing 0.424 grams of sunflower monoglycerides and 0.272 grams of water. To this were added 0.061 grams of methyl paraben and a trace of the dye 1,2-pyridylazo-2-naphthol. An upper solution of 1% cetylpyridinium bromide was prepared. The liquid crystal was heated in a 120° C. oven for five minutes, stirred vigorously, reheated, then plunged into cold water, and which time the upper solution was overlaid, the test tube sealed, and put in a sonicator. The result was a dispersion of methyl paraben-coated microparticles, with average size on the order of 1 micron. Cuprous cyanide was then used to demonstrate that the dye was protected from contact with the exterior phase. When cuprous cyanide was added to a solution of 1,2-pyridylazo-2-naphthol (whether in the presence of F-68, or not), the color changes from orange to strong purple. However, when cuprous cyanide was added to an aliquot of the dispersion of dye-containing particles, there was no color change, showing that the dye was protected from contact with the cuprous cyanide by the methyl paraben coating. One can calculate that the diffusion time of a cuprous ion into the center of a 1 micron particle is on the order of a few seconds or less, which would not have prevented the color change had the coating not sealed off the particle.

The protection of active compounds from contact with ions from the outside environment could be useful in, for example, drug delivery, in particular in delivery of a polyelectrolyte which could be complexed and inactivated by contact with multivalent ions.

Example 24

In this example the cyanide ion test of the previous example was repeated for potassium nitrate-coated particles.

A nanostructured reverse bicontinuous cubic phase material was prepared by mixing 0.434 grams of sunflower monoglycerides and 0.215 grams of water. To this were added 0.158 grams of potassium nitrate and a trace of the dye 1,2-pyridylazo-2-naphthol. An upper solution of 1% cetylpyridinium bromide in saturated aqueous potassium nitrate was prepared. The liquid crystal was heated in a 120° C. oven for five minutes, stirred vigorously, reheated, then plunged into cold water, at which time the upper solution was overlaid, the test tube sealed, and put in a sonicator. The result was a dispersion of potassium nitrate-coated microparticles. When cuprous cyanide was added to an aliquot of the dispersion of dye-containing particles, there was only a slight change of color, showing that the dye was substantially protected from contact with the cuprous cyanide by the potassium nitrate coating.

The utility of these particles is similar to those in Example 23, but the cost-effective coating potassium nitrate was used in this Example.

Example 25

A nanostructured reverse bicontinuous cubic phase material was prepared by mixing 0.913 grams of soy lecithin (Epikuron 200), 0.430 grams of oleyl alcohol, and 0.90 grams of glycerol (excess glycerol). After mixing thoroughly and centrifuging, 0.50 grams of the nanostructured reverse bicontinuous cubic phase material were removed and 0.050 grams of dibasic sodium phosphate added. An upper solution was prepared by adding 0.10 grams of calcium chloride to 3 ml of an aqueous solution containing 2% Pluronic F-68 and 1% cetylpyridinium bromide. After overlaying the upper solution on the liquid crystal—sodium phosphate mixture, the test tube was sealed and sonicated. The result was a dispersion of microparticles coated with a calcium phosphate. Calcium phosphate coatings were of inherent interest in biological contexts since calcium phosphates were a major component of bone, teeth, and other structural components.

Example 26

This example shows that the magnesium carbonate-coated particles in the example retain their integrity upon dessication, that is, when the exterior water phase was dried off. Thus, dry powders can be produced while retaining the interior as a water-rich liquid crystalline phase material.

"Tung-sorbitol compound" preparation. Initially, a "tung-sorbitol compound" was prepared as follows:

An amount of 110 grams of tung oil (obtained as Chinese Tung Oil from Alnor Oil) was combined in a reaction flask with 11.50 grams of sorbitol. The flask was purged with argon, sealed and heated to 170° C., and stirred magnetically. Sodium carbonate (3.6 grams) were added and the mixture stirred at 170° C. for 1 hour. At this point, 3.4 grams of 3-chloro-1,2-propanediol were added, and the mixture was cooled to room temperature. Seventy-five milliliters of the oily phase from this reaction were mixed with 300 ml of acetone, and a white precipitate removed after centrifugation. Next, 18 grams of water and 100 ml of acetone were added, the mixture centrifuged, and an oil residue on the bottom removed. Then 44 grams of water were added, and the bottom phase again collected and discarded. Finally, 20 grams of water were added and this time the oily residue on the bottom collected and dried under argon flow. This yielded approximately 50 ml of a tung fatty acid ester of sorbitol, which was referred to hereinafter as "tung-sorbitol product".

Example 26A. A nanostructured reverse bicontinuous cubic phase material was prepared by mixing 0.110 grams of the "tung-sorbitol product", 0.315 grams of soy lecithin, and 0.248 grams of water, mixing thoroughly, and centrifuging. To this was added 0.085 grams of potassium carbonate. An upper solution was then prepared by adding 0.118 grams of Pluronic F-68 and 0.147 grams of magnesium sulfate to 5.34 grams of water. The upper solution was overlaid onto the liquid crystal, and the test tube sealed, shaken, sonicated for 2 hours, and finally shaken well again. The result was a milky-white dispersion of microparticles coated with magnesium carbonate hydroxide. This was diluted, by adding two parts water to one part dispersion, in order to dissolve-excess inorganic crystalline material. A small drop of the dispersion was spread gently onto the surface of a microscope slide, and allowed to dry. After ten minutes of drying, the water exterior to the particles was almost completely evaporated. Microscopic examination showed that the particles nevertheless retained their shape, and did not become amorphous blobs, as was observed if uncoated particles were dried in a similar manner (as the dried liquid crystalline mixture turns to a liquid).

Example 26B. The dispersion produced in Example 26A was heated to 40° C. According to phase behavior determinations, at this temperature the interior phase was a nanostructured liquid L2 phase material. The dispersion remained milky-white, and under the microscope showed the retention of microparticles as well. Since this L2 phase contains oil, water, and surfactant (namely the lecithin), it was also a nanostructured microemulsion.

Example 27

In this example receptor proteins are disposed within the matrix of a nanostructured reverse bicontinuous cubic phase material in the internal core of magnesium carbonate-coated particles, then the coated particles were in turn embedded in a hydrogel. The coating on the particles can be used to protect the receptor protein during shipping and storage, and then easily removed by washing just before use. This example and Example 28 presage the use of coated particles of the present invention for, e.g., affinity chromatography, using hydrogel beads with coated particles of the present invention embedded in them.

An amount of 0.470 grams of soy lecithin (Epikuron 200) was mixed with 0.183 grams of the "tung-sorbitol product" (described above), and 0.359 grams of water. To this was added 0.112 grams of potassium carbonate. This was centrifuged for several hours and the excess aqueous phase removed. A preparation of torpedo nicotinic acetylcholine receptor was prepared according to the protocol described by L. Pradier and M. G. McNamee in Structure and Function of Membranes (ed. P. Yeagle, 1992, pp. 1047–1106). In this preparation, 50 micrograms of receptor protein was contained in 50 microliters of lipid, most of which was dioleoylphosphatidylcholine (DOPC). (The remainder was other membrane lipid components, such as other phospholipids, cholesterol, etc.) This amount of preparation was added to the nanostructured reverse bicontinuous cubic phase material-potassium carbonate mixture, and the entire mixture stirred gently but long enough to ensure good mixing, as checked by the absence of birefringence. An upper solution was prepared by adding 0.328 grams of magnesium sulfate, 0.324 grams of Pluronic F-68, and 0.0722 grams of cetylpyridinium bromide to 20.02 grams of water. Five grams of the upper solution were overlaid onto the test tube containing the receptor-loaded nanostructured reverse bicontinuous cubic phase material, and the test tube sealed, shaken, and sonicated for 2 hours. This resulted in a dispersion of magnesium carbonate hydroxide-coated, receptor-containing microparticles, a substantial fraction of which were in the size range of 0.5 to 1 micron.

The microparticles were then immobilized in a polyacrylamide hydrogel. Acrylamide (0.296 grams), methylene-bis-acrylamide (0.024 grams, as crosslinker), ammonium persulfate (0.005 grams, as initiator), and tetramethylethylene diamine (TMED, 0.019 grams, as co-initiator) were added to the dispersion, resulting in polymerization of the acrylamide into a crosslinked hydrogel in less than 30 minutes. A thin slice of the hydrogel was examined under a microscope, and a high concentration of microparticles was seen, just as with the original dispersion.

The hydrogel was furthermore fragmented into bits with size approximately 30 microns. This was accomplished by pressing the hydrogel through a wire mesh with a 40 micron mesh size.

Example 28

In this example receptor proteins were disposed in the internal core of coated particles of the present invention where the coating was potassium nitrate, and the coated particles in turn immobilized in hydrogel beads. The receptor-laden beads were successfully tested for binding activity in radioassays performed at UC Davis.

An amount of 0.470 grams of soy lecithin (Epikuron 200) was mixed with 0.185 grams of the "tung-sorbitol product" (described above), and 0.368 grams of water. To this was added 0.198 grams of potassium nitrate, and the contents thoroughly mixed. A preparation of torpedo nicotinic acetylcholine receptor was prepared as described in the previous Example. In this preparation, per every 50 micrograms of receptor protein was contained in 50 microliters of lipid, most of which was dioleoylphosphatidyl-choline (DOPC). Fifty-five milligrams of preparation was added to the nanostructured reverse bicontinuous cubic phase material-potassium carbonate mixture, and the entire mixture stirred gently but long enough to ensure good mixing. An upper solution was prepared by adding 0.128 grams of Pluronic P-68 and 0.015 grams of cetylpyridinium bromide to 6.05 grams of saturated aqueous potassium nitrate solution. The nanostructured reverse bicontinuous cubic phase material-potassium nitrate preparation was heated to 40° C. to dissolve potassium nitrate, then plunged into 10° C. water for 10 minutes. The upper solution was overlaid onto the test tube containing the receptor-loaded nanostructured reverse bicontinuous cubic phase material, and the test tube sealed, shaken, and sonicated for 2 hours. This resulted in a dispersion of potassium nitrate-coated, receptor-containing microparticles, a substantial fraction of which were in the size range of 0.3 to 1 micron.

The microparticles were then immobilized in a polyacrylamide hydrogel. Acrylamide (0.365 grams), methylene-bis-acrylamide (0.049 grams, as crosslinker), ammonium persulfate (0.072 grams of a 2% solution, as initiator), and tetramethylethylene diamine (TMED, 0.011 grams, as co-initiator) were added to the dispersion, resulting in polymerization of the acrylamide into a crosslinked hydrogel in a matter of hours. A thin slice of the hydrogel was examined under a microscope, and a high concentration of microparticles was seen (except near the very bottom of the hydrogel), just as with the original dispersion.

The hydrogel was furthermore fragmented into bits with size approximately 30 microns. This was accomplished by pressing the hydrogel through a wire mesh with a 40 micron mesh size. At a 40 micron bit size, one can estimate that the diffusion time for a small molecule into the center of a bit is on the order of a second or less, which does not have a significant impact on the receptor tests reported next.

Using $^{125}$I-labeled bungarotoxin as the ligand, an assay of receptor binding was performed using the nanostructured reverse bicontinuous cubic phase material microparticle-immobilized acetylcholine receptor system just described. The standard assay for binding has been described in publications from Dr. Mark McNamee's group. The results showed that the nanostructured reverse bicontinuous cubic phase material microparticle-immobilized acetylcholine receptor system exhibited binding of the bungarotoxin at approximately 70% of the level measured with the standard receptor preparation, demonstrating the retention of protein binding properties throughout not only the immobilization procedure, but also the period (more than two months) that elapsed between the date on which the sample was prepared and the date it was tested.

In addition to demonstrating the production of particles of the instant invention incorporating receptor proteins capable of targeting specific sites in the body, the foregoing Examples 26–28 actually show the application of the particles in biochemical assays, with a high degree of improvement in stability over the commonly used liposomes, which are inconvenient due to their inherent instabilities. Such assays are important in clinical diagnoses, as well as in pharmaceutical drug screening.

Example 29

As in Example 22 above, clathrate-coated particles were produced in this example. In this example the nanostructured reverse bicontinuous cubic phase material interior can be polymerized, by the effect of oxygen which can pass through the coating (the coating nevertheless prevents passage of water).

Lecithin extracted from Krill shrimp was obtained as Krill shrimp phosphatidylcholine from Avanti Polar Lipids of Birmingham, Alabama. An amount of 0.220 grams of this lecithin was mixed with 0.110 grams of "tung-sorbitol product", 0.220 grams of water, 0.005 grams of a cobalt dryer (from the art materials supply company Grumbacher) containing cobalt naphthenate, and 0.30 grams of potassium thiocyanate. This formed a green-colored nanostructured reverse bicontinuous cubic phase material. An upper solution was prepared by adding 0.309 grams of manganese chloride, 0.105 grams of 4-picoline (4-methyl pyridine), 0.113 grams of Pluronic F-68, and 0.021 grams of cetylpyridinium bromide to 5.10 grams of water. The upper solution was overlaid on the nanostructured reverse bicontinuous cubic phase material, the test tube sealed, shaken, and sonicated, with ice water filling the sonication bath water. As the green-color nanostructured reverse bicontinuous cubic phase material was dispersed into microparticles, the reaction caused a color change to brown. After two hours, substantially all of the nanostructured reverse bicontinuous cubic phase material had been dispersed into particles, which were mostly submicron in size. The coating was a Werner compound, which according to the literature has channels that allow the absorption of (or passage of) molecular oxygen. The high degree of unsaturation in the Krill lecithin, as well as that in the tung-sorbitol product, together with the catalytic action of the cobalt dryer, makes it possible to polymerize this microencapsulated nanostructured reverse bicontinuous cubic phase material by contact with atmospheric oxygen.

The clathrates described in this example were discussed above (Example 22).

Example 30

In this example a nanostructured reversed hexagonal phase material was dispersed.

A nanostructured reversed hexagonal phase material was prepared by mixing 0.369 grams of soy lecithin (Epikuron 200), 0.110 grams of sorbitan trioleate, and 0.370 grams of glycerol. To this nanostructured reversed hexagonal phase material was added 0.054 grams of magnesium sulfate. An upper solution was prepared by adding 0.10 grams of potassium carbonate, 0.10 grams of Pluronic F-68, and 0.02 grams of cetylpyridinium bromide to 5 grams of water. The upper solution was overlaid on the nanostructured reversed hexagonal phase material, and the test tube sealed, shaken and sonicated for one hour, resulting in a dispersion of most of the nanostructured reversed hexagonal phase material into microparticles coated with magnesium carbonate hydroxide.

The dimensionality of the pores (cylindrical) in the reversed hexagonal phase provides a unique release kinetics profile which could be useful in, for example, controlled drug delivery.

Example 31

In contrast with most of the above examples, the nanostructured reversed hexagonal phase material that was dispersed in this example was not in equilibrium with excess water, although it was insoluble in water.

Soy lecithin (0.412 grams), linseed oil (0.159 grams), and glycerol (0.458 grams) were thoroughly mixed, producing a nanostructured reversed hexagonal phase material at room temperature. To this nanostructured reversed hexagonal phase material was added 0.059 grams of magnesium sulfate. An upper solution was prepared by adding 0.10 grams of potassium carbonate, 0.10 grams of Pluronic F-68, and 0.02 grams of cetylpyridinium bromide to 5 grams of water. The upper solution was overlaid on the nanostructured reversed hexagonal phase material, and the test tube sealed, shaken and sonicated for 30 minutes, resulting in a dispersion of most of the nanostructured reversed hexagonal phase material into microparticles coated with magnesium carbonate hydroxide.

The ability to disperse nanostructured phases which are not in equilibrium with excess water expands the range of chemistries which can be used in the present invention. This versatility is especially important in demanding applications, such as drug delivery, where a large number of product criteria must be simultaneously satisfied.

Example 32

In this example, the nanostructured lamellar phase material was dispersed using a chemical reaction process.

A nanostructured lamellar phase material was prepared by mixing 0.832 grams of soy lecithin (Epikuron 200) and 0.666 grams of water. To approximately 0.80 grams of this nanostructured lamellar phase material was added 0.057 grams of magnesium sulfate. An upper solution was prepared by adding 0.10 grams of potassium carbonate, 0.10 grams of Pluronic F-68, and 0.02 grams of cetylpyridinium bromide to 5 grams of water. The upper solution was overlaid on the nanostructured reversed hexagonal phase material, and the test tube sealed, shaken and sonicated for five minutes, resulting in a dispersion of most of the nanostructured lamellar phase material into microparticles coated with magnesium carbonate hydroxide.

The particles in this Example bear a structural relationship with polymer-encapsulated liposomes, but do not suffer from the harsh chemical conditions used to produce polymer-encapsulated liposomes; the ability to produce, in a single step, lamellar phase-interior particles coated with a wide range of crystalline coatings, and under mild conditions, could make the present invention of importance in controlled release drug delivery.

Example 33

Preparation of free bases. Both ethylhydrocupreine and neutral red were purchased in the protonated hydrochloride form. In each case this salt was dissolved in water, to which was added aqueous sodium hydroxide in 1:1 molar ratio. The mixture of the two aqueous solutions produced a precipitate that was washed with water (to remove NaCl and any unreacted NaOH), centrifuged and then dried above the melting point of the free base.

Preparation of nanostructured reverse bicontinuous cubic phase dispersions.
Formulation of Dispersions Began With the Following Mixture:
 0.417 gm glycerol monooleate (GMO)
 0.191 gm glycerol
 0.044 gm ethylhydrocupreine (or, as the case may be, neutral red, both in free base form).

Instead of the usual monoglyceride—water nanostructured reverse bicontinuous cubic phase material, the monoglyceride—glycerol nanostructured reverse bicontinuous cubic phase material was used in these examples.

An upper solution was made by dissolving Pluronic F-68 in water to a level of 2%.

After weighing the components into a test tube and mixing with a spatula, the sealed (twist-cap) test tube was put in a 140° C. oven for at least 20 minutes, and the ethylhydrocupreine (or neutral red free base) was checked to have melted. The test tube was then plunged into water, which was below room temperature (about 10° C.) in some cases and room temperature water in others; no difference was found in the dispersions in the two cases.

After the sample had been in the cooling water for about 5 minutes, the viscosity was checked to be very high, indicating a nanostructured reverse bicontinuous cubic phase; in some cases the sample was observed through crossed polars for optical isotropy (the crystalline coating domains are much smaller than the wavelength of light, too small to affect the optical properties). The Pluronic upper solution was poured into the test tube until about half full. The tube was then shaken, by hand and with the use of a mechanical mixer. The solution became increasingly opaque as the bulk nanostructured reverse bicontinuous cubic phase material disappeared and went into dispersion.

SEM characterization. Scanning electron microscope (SEM) preparation did not involve any fixation technique whatsoever. A drop of dispersion was simply placed on a glass slide, the water evaporated, and a thin (2 nm) coating of carbon sputtered on to avoid charging effects. In the sputtering apparatus, before sputtering began the sample was deliberately held for about 5 minutes at a vacuum of $5 \times 10^{-4}$ Torr. This was done to test the robustness of the particle coating. The SEM used was a Hitachi S-800 field-emission SEM, and was operated at 25 kV.

Figure 3:
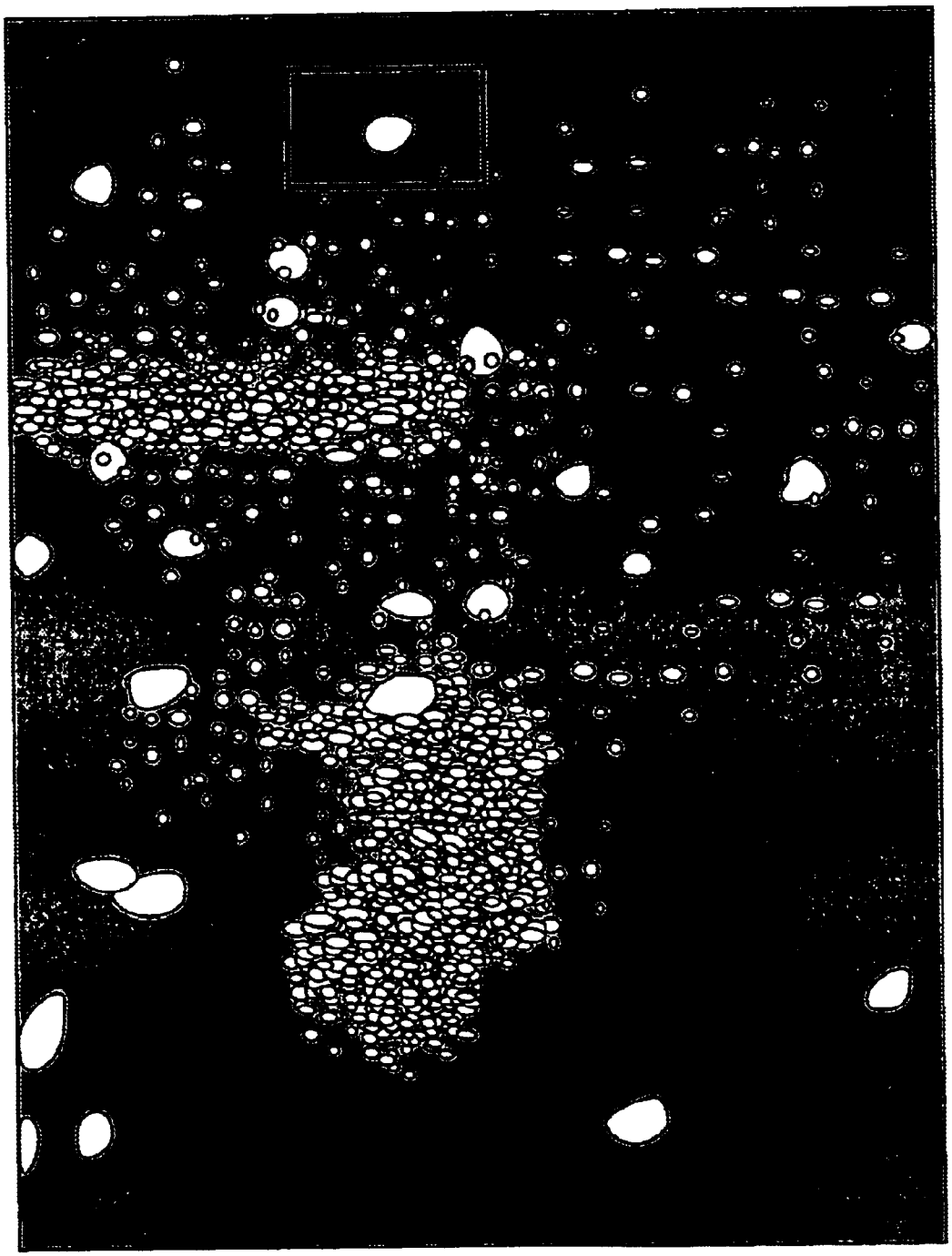
FIG. 3 is a scanning electron microscope micrograph of coated particles of the present invention.

FIG. 3 shows an SEM micrograph of an ethylhydrocupreine dispersion, and particles in the range of about 0.5–2 micron diameter are seen (the bottom half is a 10× magnification of the area boxed in the top half, so that the magnification is 500 on top and 5,000 on the bottom). Many of the particles, remarkably, distinctly show a polyhedral shape.

The measured particle size distribution for this sample (see the next section) showed that particles on the order of 0.5–2 microns diameter dominate in this dispersion, and this agrees well with the particles seen in the micrograph. One can estimate that the thickness of the ethylhydrocupreine coating in a 0.5 micron particle was about 10 nm, and this was clearly thick enough that it was able to protect the liquid components in the interior of the particles from evaporation in the 0.5 mTorr vacuum.

In this dispersion, the nanostructured reverse bicontinuous cubic phase material was loaded with lithium sulphate as a marker before dispersing, and indeed the EDX spectra of particles in this dispersion showed a sulfur peak. Lithium cannot be detected by the EDX used, and other peaks in the spectrum were attributed to the glass substrate.

Figure 4:
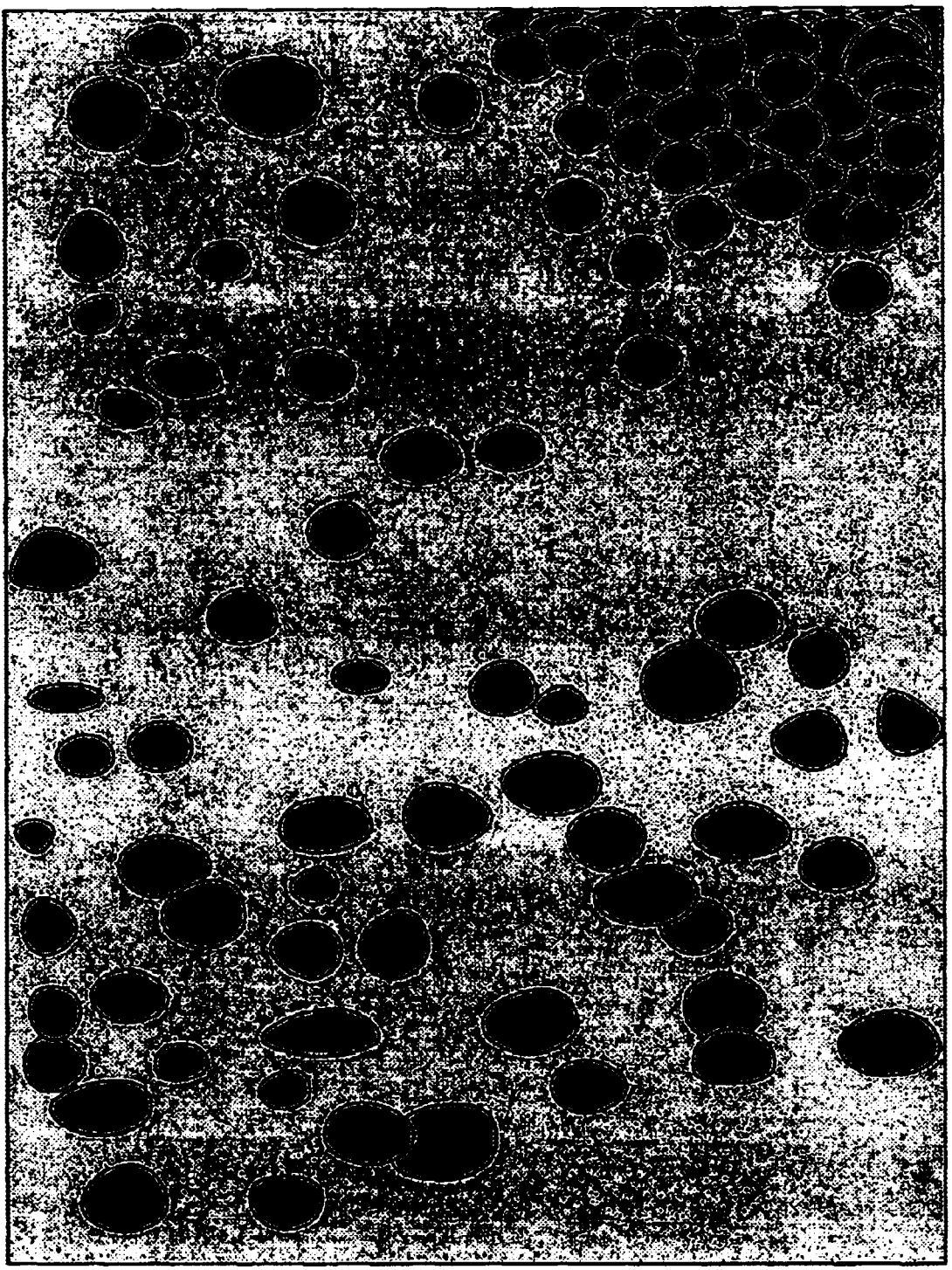
FIG. 4 is a scanning electron microscope micrograph of other coated particles of the present invention.

FIG. 4 shows an SEM micrograph of a neutral red dispersion. Substantially all of the particles have sizes in the range of 0.3–1 micron.

Particle size distribution. A Malvern 3600E laser diffraction particle sizer was used to measure the distribution. For each dispersion checked, a few drops were added to the carrier fluid (water), resulting in a large dilution of the concentration so as to avoid multiple scattering. The particle size was computed as the diameter of a sphere of the same volume, which is a good measure considering the polyhedral shape of the particles. (See below.) The instrument is capable of measuring particles down to at least 0.5 micron, and data on the distribution include contributions at least down to 0.5 microns.

Figure 5:
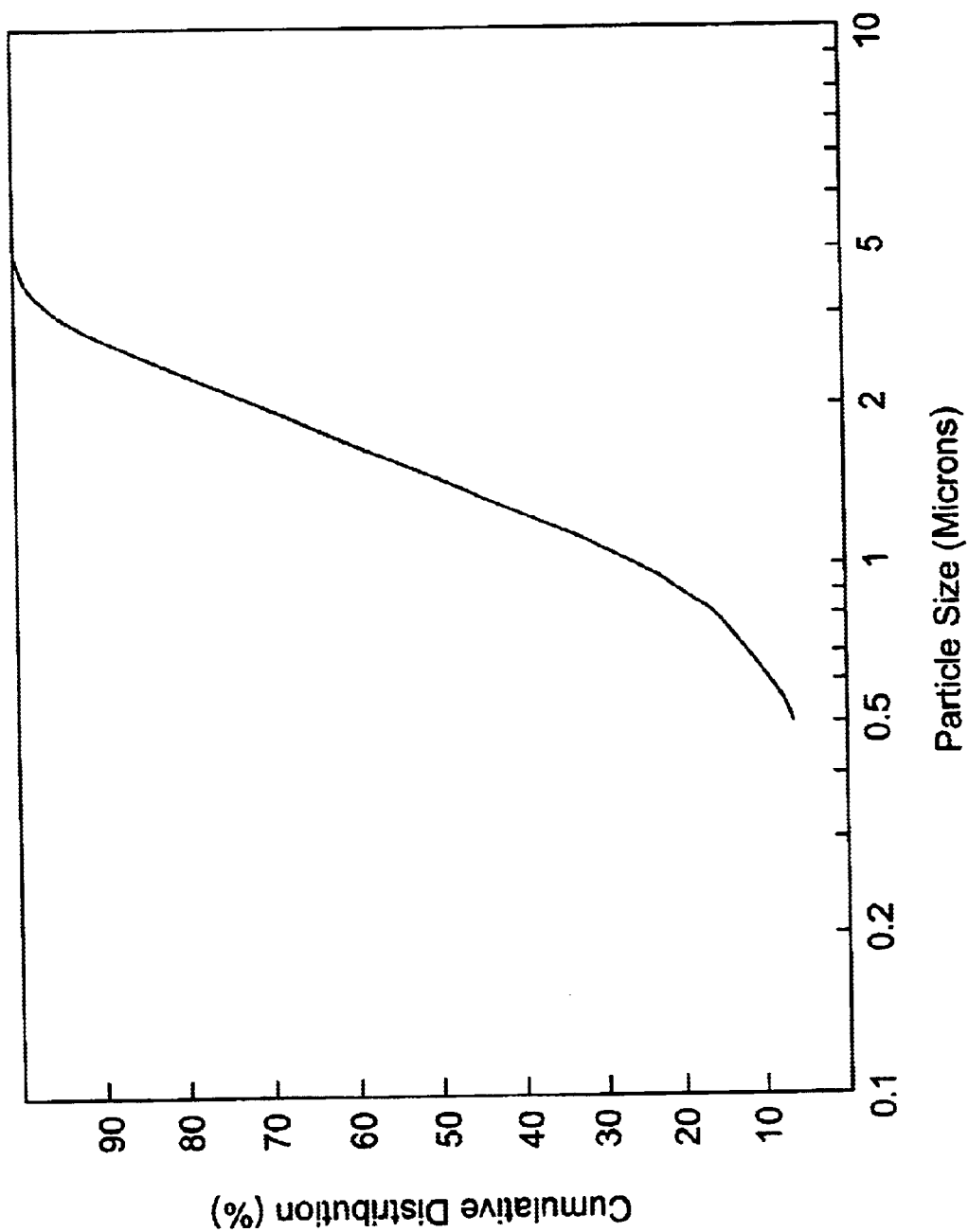
FIG. 5 is a graph of the measured volume-weighted cumulative particle size distribution for coated particles of the present invention on a volume-weighted particle diameter versus cumulative particle size basis.

The particle size distribution of a dispersion prepared with a 13:1 ratio of GMO:ethylhydrocupreine is shown in FIG. 5. In general, as the ratio of nanostructured reverse bicontinuous cubic phase material to crystalline coating agent increases so does the particle size. The data for this dispersion show that, on a volume average basis, 10% of the particles have particle size less than 0.6 microns, this being represented by the equation D(v,0.1)=0.6 micron. The narrowness of the distribution is indicated in two ways. First, the D(v,0.9) and D(v,0.1) are each a factor of 2 from the (volume-weighted) average of D(v,0.5)=1.2 micron. And second, the "span", which gives the width of the distribution as:

$$\mathrm{span} = [D(v,0.9) - D(v,0.1)]/D(v,0.5)$$

is computed to be 1.4. These results indicate a fairly low degree of agglomeration.

A narrower distribution was indicated for a dispersion with GMO:neutral red=10:1. The span is given as 1.1, and the (differential) particle size distribution was easily seen to be quite sharp, dropping off quickly above 2 micron.

A small particle size was measured for a dispersion prepared with a lower GMO:ethylhydrocupreine ratio, with a distribution averaging 0.8 microns, and a span of 1.2. Thus, particle size can be controlled by the ratio of nanostructured reverse bicontinuous cubic phase material to crystalline coating agent, with the particle size decreasing with decreasing ratio.

Small-angle X-ray scattering (SAXS). This was used to verify that the interior of the particles in an ethylhydrocupreine dispersion was a nanostructured reverse bicontinuous cubic phase material. The dispersion itself-not a concentrate of the particles-was loaded into a 1.5 mm x-ray capillary, which was transported to the laboratory of Dr. Stephen Hui at Roswell Park Cancer Center Biophysics Department. The SAXS camera was equipped with a rotating anode, and measurements were performed at 100 kV, 40 mV power (4 kW). Data were collected using a linear position-sensitive detector connected through an electronics setup to a Nucleus multichannel analyzer. The MCA has the capacity for 8,192 channels, but only 2,048 resolution was used to increase the counts per channel. Counting times on the order of an hour were used because the volume fraction of nanostructured reverse bicontinuous cubic phase material in the dispersion (which was about 85% of the particle volume) was on the order of 10%. The software package "PCA" was used for analysis of the data.

Figure 6:
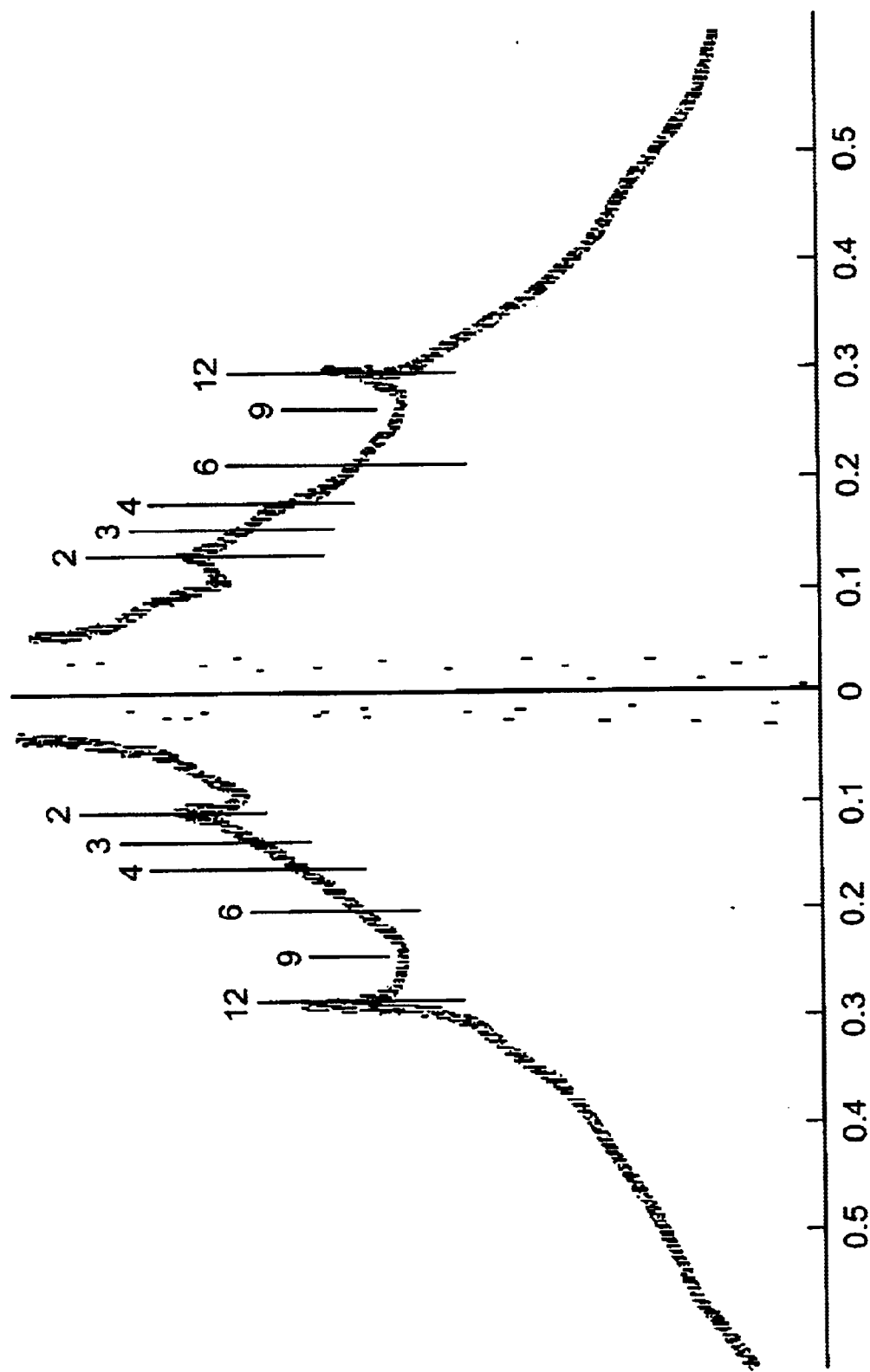
FIG. 6 is a graph of measured small-angle X-ray scattering intensity versus wave vector q of coated particles of the present invention.

FIG. 6 shows the measured SAXS intensity versus wave vector q plot. The wave vector q is related to the diffraction angle θ and the wavelength λ of x-rays by the formula:

$$q = 4\pi (\sin \theta)/\lambda.$$

A d-spacing is calculated from the q-value of a Bragg reflection by:

$$d = 2\pi/q.$$

In FIG. 6, vertical lines given the exact, calculated Bragg peak positions for a lattice with space group Pn3m and lattice parameter 7.47 nm. This space group is well-established for nanostructured reverse cubic phases in the monoolein-water system, particularly for those which are in equilibrium with excess water. (Indeed, in nanostructured reverse cubic phases which are in equilibrium with excess water, the space group Pn3m almost exclusively appears). Lattice parameters for the monoolein-water nanostructured reverse cubic phase with space group Pn3m are also close to 8 nm; a more exact comparison was impossible because of the substitution of glycerol for water in the present case. In any case, the lattice type and size deduced from this SAXS scan are in exact accord with literature data for monoglyceride nanostructured reverse cubic phases.

In the space group Pn3m, the Miller indices (hkl) for the allowed peak positions, and the value of $h^2+k^2+l^2$, are: (110), 2; (111), 3; (200), 4; (211), 6; (200), 8; (221), 9; (222), 12; and higher. Looking at the data and the expected peak positions, it is clear that the peaks at the (110) and (222) positions are strongly supported by the data. The (111) peak appears as a shoulder to the (110) peak on the right side of the scan, and as a small but discernible peak on the left side. The (200) peak is supported at least on the right side of the scan; this peak is always measured to be much less intense than the (110) and (111) peaks in monoglyceride Pn3m phases, and in Pn3m phases in general, and this has been found to be in accord with theoretical amplitude calculations [Strom, P. and Anderson, D. M. (1992) Langmuir, 8:691]. The (211) peak is supported by data on the left side of the scan, and the (221) by data on the right side. The absence or low intensity of peaks between the (211) and (222) is a consequence of the low concentration (10%) of nanostructured reverse bicontinuous cubic phase in the dispersion, since the intensity of diffracted x-rays varies as the square of the volume concentration. Despite this, the definitive peaks at the (110) and (222) positions, and the perfect agreement of the deduced lattice and lattice parameter with related systems in the literature provide strong support for the conclusion that the SAXS data demonstrate nanostructured reverse bicontinuous cubic phase ordering in the particle interiors.

These particles could be useful in, for example, controlled release of antiseptics in oral rinses, where the solubilities of the two coatings at slightly lowered pH (on the order of 5) was in the right range to make delivery preferential at sites of bacterial activity.

Example 34

High-performance liquid chromatography (HPLC) was used to characterize the integrity under shear and pressure of two dispersions, one chosen to have a rigid coating—cupric ferrocyanide—and the other a soft, easily disrupted coating, the latter, to act essentially as a control, to quantify any release under pressure of the more rigid coating. In other words, if the concentration of marker in the two dispersions were approximately the same, and the release of marker in the rigid system were a small fraction, say. x% (where x is substantially less than 100), of the release of marker in the soft system, then one could conclude that only x% of the particles in the rigid system broke up under the pressure, and the remaining (100−x)% remained intact during the HPLC. Indeed, this percentage 100−x is a lower limit; the actual percentage of intact rigid particles would be calculated to be higher if it were found that some fraction of the soft particles in the control had actually remained intact, though this possibility is remote. In any case, the calculations were assumed to be on a worst case scenario, by assuming that all the control particles broke up.

Preparation of the Dispersions.

Example 34A. A nanostructured reverse bicontinuous cubic phase material was prepared by mixing 0.499 grams of soy lecithin, 0.163 grams of oleyl alcohol, 0.900 grams of glycerol, and 0.1.24 grams of capsaicin. To 0.842 grams of the nanostructured reverse bicontinuous cubic phase:material from this system was added 0.043 grams of sodium cholate. An upper solution was prepared by adding 1 drop of 1M HCl to 3.00 grams of pH 5 phosphate buffer. The upper solution was overlaid onto the liquid crystalline material, and the test tube sealed and sonicated, resulting in a milky-white dispersion of microparticles.

Example 34B. A nanostructured reverse bicontinuous cubic phase material was prepared by mixing 0.329 grams of soy lecithin, 0.108 grams of oleyl alcohol, 0.611 grams of glycerol, and 0.105 grams of capsaicin. To this were added 0.046 grams of cupric sulfate. An upper solution was prepared by adding 0.563 grams of 10% potassium ferrocyanide solution to 2.54 grams of water. The upper solution was overlaid onto the liquid crystal and the test tube sealed and sonicated, resulting in a milky-white dispersion of microparticles coated with cupric ferrocyanide.

The concentration of marker, namely capsaicin, was comparable in the two samples. The final concentration in the cupric ferrocyanide dispersion was 2.44%, compared to 3.19% for Example 34B—a 30% difference, which will be accounted for in the calculations below.

Figure 7:
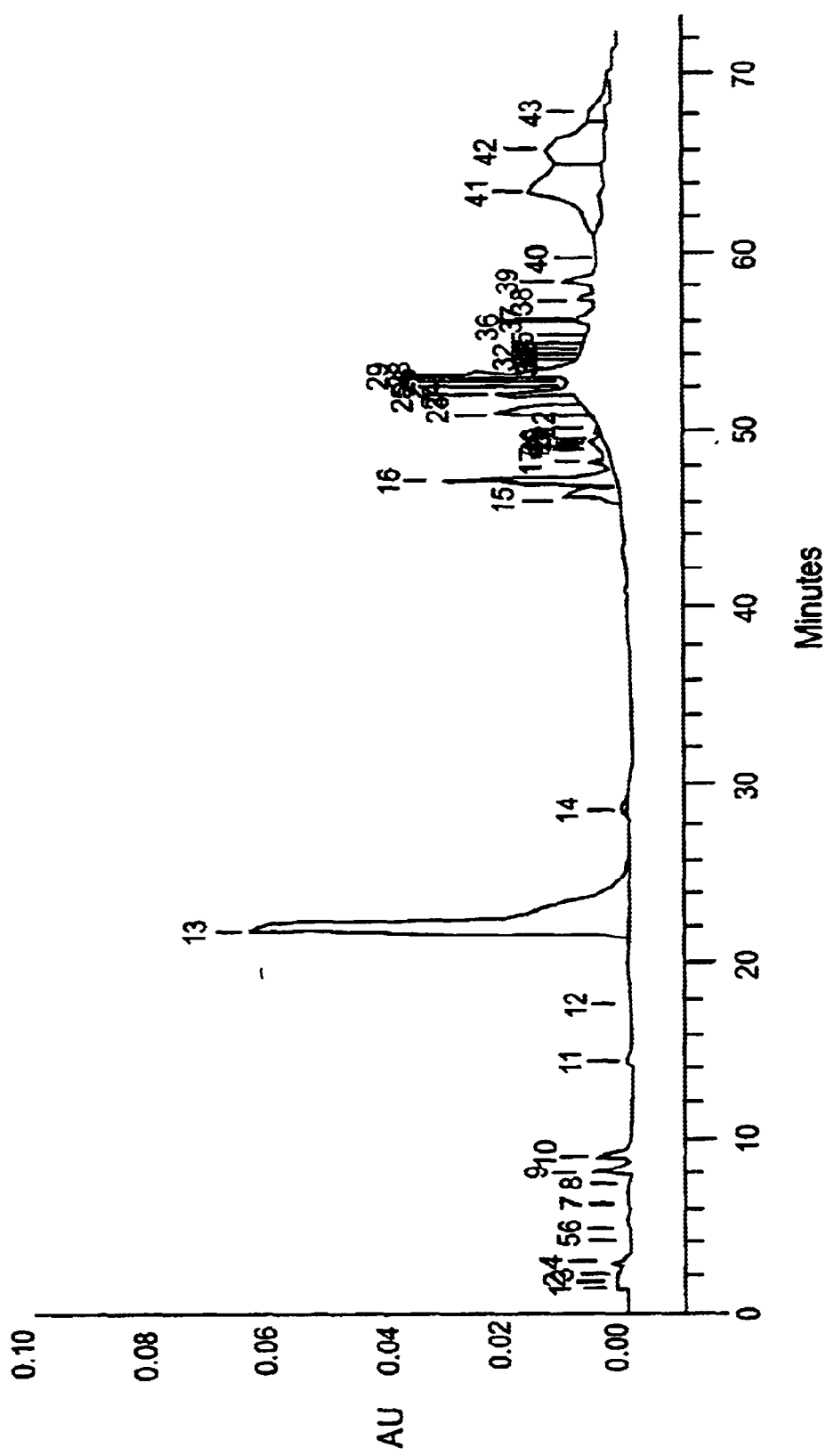
FIG. 7 is a graph of detector counts versus elution time in minutes for a control using high pressure liquid chromatography.

Purified capsaicin was then run in HPLC and found to have an elution time of 22 minutes (data not shown). Under these identical conditions, the two dispersions prepared above were run. The data for the particles of Example 34B is shown in FIG. 7, and for the cupric ferrocyanide particles in FIG. 8. Tables 1 and 2 give the integrated peaks corresponding to FIGS. 7 and 8, respectively, as output from the HPLC computer; sampling rate was 5 Hz.

Clearly there is a strong peak in FIG. 7 at 22 minutes elution time (numbered peak 13 by the computer), and Table 1 gives the integrated intensity of this peak as 3,939,401. A much smaller peak is seen at 22 minutes in FIG. 8 (numbered 10 by the computer), and Table 2 gives the intensity as 304.29.

If these integrated peak values are normalized according to the concentration of capsaicin in the two samples, namely 3,939,401/0.0319 for the Example 34B case and 304,929/0.0244 for the cupric ferrocyanide case, the ratio of the normalized peak intensity for the cupric ferrocyanide case to the Example 34B case is 0.101—that is, at most 10.1% of the cupric ferrocyanide particles released the capsaicin marker under the HPLC conditions.

These particles have a coating which is a mineral of low aqueous solubility, making them of potential utility in applications requiring release of the particle coating by strong shear, while at the same time protecting against release due to simple dilution with water. An example of such an application would be where a rodent deterrent such as capsaicin, or rodent toxin, would be encapsulated, the particles impregnated into electrical wires, corrugated boxes, and other products:requiring protection against gnawing by rodents, and the gnawing action of a rodent would induce release of the active deterrent or toxin. The low water solubility would prevent the deterrent from premature release due to damp conditions.

TABLE 1

Integrated peak intensities corresponding to FIG. 7 for HPLC analysis of Example 34B particles containing capsaicin. Peak #13 is the main capsaicin peak.

| Peak | Area |
| --- | --- |
| 1 | 2914 |
| 2 | 8096 |
| 3 | 2848 |
| 4 | 29466 |
| 5 | 11304 |
| 6 | 2254 |
| 7 | 12871 |
| 8 | 4955 |
| 9 | 124833 |
| 10 | 113828 |
| 11 | 19334 |
| 12 | 7302 |
| 13 | 3939401 |
| 14 | 39153 |
| 15 | 255278 |
| 16 | 755868 |
| 17 | 52623 |
| 18 | 19395 |
| 19 | 4899 |
| 20 | 10519 |
| 21 | 5101 |
| 22 | 1481 |
| 23 | 344230 |
| 24 | 9971 |
| 25 | 194442 |
| 26 | 89831 |
| 27 | 80603 |
| 28 | 105163 |
| 29 | 186224 |
| 30 | 194020 |
| 31 | 36805 |
| 32 | 2115 |
| 33 | 23296 |
| 34 | 4327 |
| 35 | 5166 |
| 36 | 90236 |
| 37 | 62606 |
| 38 | 44523 |
| 39 | 110347 |
| 40 | 4391 |
| 41 | 1275597 |
| 42 | 1353000 |
| 43 | 238187 |

TABLE 2

Figure 8:
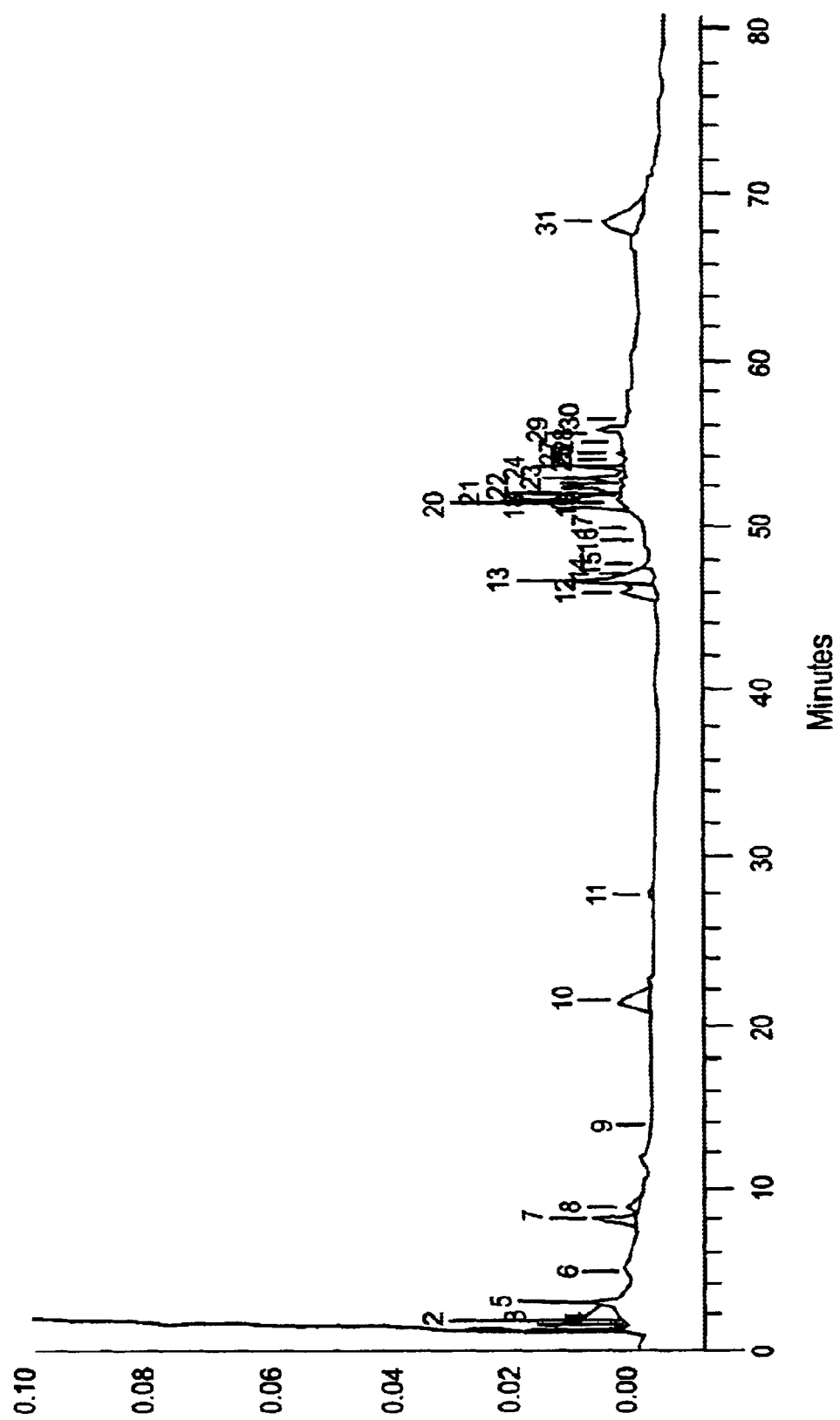
FIG. 8 is a graph of detector counts versus elution time in minutes for coated particles of the present invention using high pressure liquid chromatography.

Integrated peak intensities corresponding to FIG. 8 for HPLC analysis of cupric ferrocyanide-coated particles containing capsaicin. Peak #10 is the main capsaicin peak.

| Peak | Area |
| --- | --- |
| 1 | 1681172 |
| 2 | 3011240 |
| 3 | 106006 |
| 4 | 2760 |
| 5 | 59059 |
| 6 | 38727 |
| 7 | 163539 |
| 8 | 44134 |
| 9 | 6757 |
| 10 | 304929 |
| 11 | 10466 |
| 12 | 141800 |
| 13 | 332742 |
| 14 | 14442 |
| 15 | 6996 |
| 16 | 15008 |
| 17 | 11940 |
| 19 | 91446 |

TABLE 2-continued

Integrated peak intensities corresponding to FIG. 8 for
HPLC analysis of cupric ferrocyanide-coated particles
containing capsaicin. Peak #10 is the main capsaicin peak.

| Peak | Area |
|---|---|
| 20 | 250214 |
| 21 | 251902 |
| 22 | 203000 |
| 23 | 44658 |
| 24 | 110901 |
| 25 | 24296 |
| 26 | 19633 |
| 27 | 25527 |
| 28 | 15593 |
| 29 | 75442 |
| 30 | 40245 |
| 31 | 421437 |

Example 35

A nanostructured cubic phase liquid crystal was prepared by mixing 0.77 grams of soy lecithin (Epikuron 200, from Lucas-Meyer), 0.285 grams of oleyl alcohol, and 0.84 grams of glycerol, to which was added 0.11 grams of auric chloride. No heating was used in the equilibration of this mixture, only mechanical stirring with a spatula. An amount 0.595 grams of this mixture was removed and smeared along the bottom half of the inner surface of a test tube. An upper solution was prepared by dissolving 0.14 grams of ferrous chloride and 0.04 grams of Pluronic F-68 in 1.74 grams of distilled water. After overlaying the upper solution the test tube containing the cubic phase was sonicated, resulting in a dispersion of microparticles coated with a gold coating. A control sample, in which the upper solution contained the F-68 but no ferrous chloride, was sonicated side by side with the first sample and did not result in a dispersion of microparticles. The reaction between ferrous chloride and auric chloride results in the precipitation of elemental, nonlamellar crystalline gold, which in the case of the first sample resulted in the creation of microparticles covered with gold, with cubic phase interior. A glycerol-water mixture with a density approximately 1.2 gram/cc was then prepared by mixing 0.62 g of glycerol with 0.205 grams of water, and approximately 0.1 grams of the dispersion was added to this, and the new dispersion centrifuged. A substantial fraction of the microparticles could be centrifuged to the bottom of this test tube after centrifuging for 3 hours, demonstrating that the density of these particles was significantly higher than 1.2; this was due to the presence of the gold coating, since the density of the cubic phase was less than 1.2—indeed, a portion of the cubic phase which was not dispersed during the time of sonication could be centrifuged out of the original dispersions as a lower-density band, showing that this liquid was even less dense than the original dispersion.

Because gold is well-known for exhibiting chemical inertness—as well as good mechanical properties when in the form of very thin films, and since it is also approved by the FDA for many routes of administration, gold-coated particles could be useful in safe, environmentally-friendly products demanding chemically and physically stable coatings. Furthermore, such particles could be effective in the treatment of arthritis, by providing greatly increased surface area of gold over other colloidal forms.

Example 36

A nanostructured liquid phase containing the antineoplastic drug Paclitaxel was prepared by solubilizing 0.045 grams of Paclitaxel, 0.57 grams of eugenol, 15 grams of soy lecithin (Epikuron 200), 0.33 grams of glycerol, and 0.06 grams of cupric nitrate with 0.61 grams of methanol, and then evaporating off the methanol in an evaporating dish, with stirring during evaporation. An glycerol-rich upper solution was prepared by dissolving 0.09 grams of potassium iodide, 0.05 grams of Pluronic F-68, 0.44 grams of water and 1.96 grams of glycerol. After overlaying the upper phase, the system was sonicated, resulting in the dispersing of Paclitaxel-containing, nanostructured liquid phase into microparticles coated with crystalline iodine. Since these ingredients were chosen for their general acceptance as safe, inactive (except for the Paclitaxel itself) excipients in pharmaceutical preparations, this formulation or a variation thereof could be of importance in the delivery of Paclitaxel for the treatment of cancer. The loading of Paclitaxel in the particle interior was quite high, namely on the order of 3 wt %, which in this case was so high that precipitation of some of the Paclitaxel within the interior of each particle may occur since the solubilization of Paclitaxel in this cubic phase at this high loading was metastable. However, studies indicate that the precipitation is very slow, taking hours or even days, at such loadings, so that substantially all of the Paclitaxel remains in solution during the course of the production of particles; thereafter, the confinement of the Paclitaxel within the coated particles prevents the formation of large crystals (larger than a micron). If the concentration of Paclitaxel in this system were lowered, to 0.7% or less of the interior, then the solubilization of Paclitaxel becomes a truly stable solubilization (thermodynamic equilibrium), so that precipitation is prevented altogether, and microparticles of the present invention coated with nonlamellar crystalline iodine can be produced as described in this Example. Thus this system provides several scenarios for use in Paclitaxel delivery for cancer treatment.

Example 37

A Paclitaxel-containing cubic phase liquid crystal was prepared by mixing 0.345 grams of soy lecithin (Epikuron 200), 0.357 grams of anisole, 0.26 grams of water and 0.02 grams of Paclitaxel (from LKT Laboratories): equilibration was speeded by plunging a test tube of the mixture, after vigorous stirring, into boiling water for one minute then cooling to room temperature. To provide a coating material, 0.07 grams of propyl gallate was stirred in and the test tube again heated in boiling water. It had previously been checked that propyl gallate does not dissolve appreciably in this cubic phase at room temperature, but that the solubility increases substantially at 100° C. An upper solution consisted of 2.25 grams of a 2% Pluronic F-68 solution. The cubic phase-propyl gallate mixture was heated to 100° C., cooled to about 80° C., stirred with a spatula at the elevated temperature, and reheated to 100° C. After cooling the mixture for about 30 seconds, the upper solution was then overlaid on this mixture and the test tube placed in a sonication bath for one hour. A dispersion of microparticles with Paclitaxelcontaining interior and coated with propyl gallate was obtained. The dispersion had a high concentration of extremely fine microparticles (estimated particle diameter less than 0.4 micron), which were observable in the optical microscope at 1000× by virtue of their Brownian motion. The overall particle size distribution was fairly broad, with some particles as large as 1–2 microns. Only a very small amount of precipitated Paclitaxel, in the form of needles, was observed, so that nearly all of it must be in the interiors of the microparticles. The concentration of Paclitaxel in this example was high enough that the solubilization was metastable, which has implication as discussed in the previous example. Since the concentration of the antineoplastic drug Paclitaxel in the interiors of these particles was about 2%, and the components of the formulation are on the FDA list of approved inactive excipients for oral delivery, (and nearly all of them for injection as well), this formulation could be very important as a drug-delivery, formulation for the treatment of cancers.

Example 38

The amphiphilic polyethyleneoxide-polypropyleneoxide block copolymer Pluronic F-68 (also called Poloxamer 188), in the amount of 1.655 grams, was mixed with 0.705 grams of eugenol and 2.06 grams of water. Upon centrifugation, two phases resulted, the bottom phase being a nanostructured liquid phase, and the top a nanostructured cubic phase. An amount of 0.68 grams of the liquid crystalline phase was removed, and to it were added 0.05 grams of sodium iodide. A drop of eugenol was added to 2.48 grams of the lower phase to ensure low viscosity, and this nanostructured liquid phase, with 0.14 grams of silver nitrate added, served as the "upper solution" in dispersing the liquid crystalline phase. Thus, the liquid phase was overlaid on the liquid crystalline phase containing the iodide, and the mixture sonicated for 1.5 hours. The result was a dispersion of sliver iodide-coated particles in an external medium of the nanostructured liquid phase.

This Example illustrates the use of nanostructured liquid crystalline phases based on block copolymers as interior matrices for particles of the present invention. In this case, water was used as a preferential solvent for the polyethyleneoxide blocks of the block copolymer, and eugenol as preferential solvent for the polypropyleneoxide blocks of the block copolymer (which are insoluble in water).

This Example also illustrates the use of a general approach discussed above, namely the use of a nanostructured phase as the mixture that serves as the "upper solution", providing moiety B which reacts with moiety A in the interior phase to cause precipitation of a crystalline coating material. In this case, B is the silver nitrate, which induces precipitation of silver iodide on contact with the interior matrix A (the cubic phase) which contains sodium iodide. As discussed above, it is generally desirable to choose this upper solution so that it is in equilibrium with the interior matrix, or, as in this case, very nearly so (the only deviation from true equilibrium being due to the addition of a single drop, about 0.01 grams or less than 0.5% of eugenol to the upper solution). As in this approach, is generally useful to choose the interior matrix so that it is a viscous material, much more so than the upper solution which should be of relatively low viscosity.

Example 39

A poly(lactic-glycolic acid) polymer (PLGA), with a 59:41 lactide:glycolide ratio and an inherent viscosity of 0.51 dl/gm, was obtained from Purac Biochem (The Netherlands). This copolymer is known to be amorphous, and this was evidenced by lack of birefringence. An amount 0.307 grams of this polymer was dissolved in 3.002 gm of ethyl acetate. A cubic phase was prepared by mixing 0.042 grams of the prothrombogenic compound menadione, 0.272 grams of oil of ginger, 0.224 grams of water, and 0.540 grams of the ethoxylated hydrogenated castor oil surfactant Arlatone G (obtained from Uniquema). This was heated to 50° C. in order to dissolve the menadione. An amount 0.302 grams of this cubic phase was added to a second 16 ml glass tube, overlaid with 9.707 ml of water, and dispersed into the water by shaking. The PLGA solution was added to the cubic phase dispersion, the mixture shaken immediately, and sonicated for 10 minutes. Following this, the contents were transferred into a round bottom flask, placed on a rotovap apparatus, and evaporated to a final volume of approximately 9.7 ml.

Figure 9:
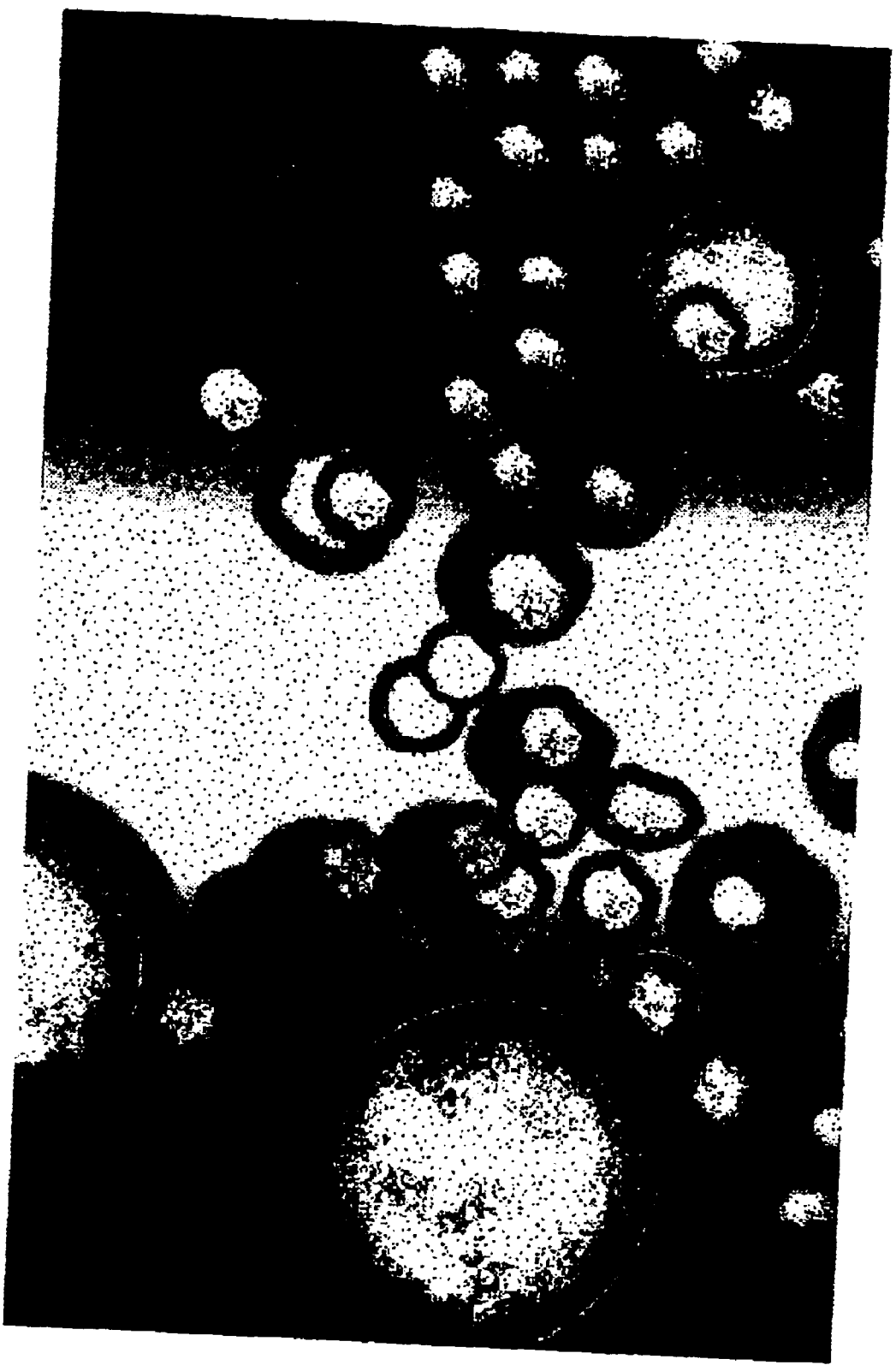
FIG. 9. A phase-contrast optical micrograph of PLGA-coated microparticles dispersed in water, showing the core-shell structure.

This resulted in PLGA-coated,particles of two types. First, in the water phase, comprising approximately 2% by volume, were microparticles of cubic phase coated with PLGA. A significant fraction of these microparticles were large enough to see structural detail in a phase-contrast optical microscope. An optical micrograph is shown in FIG. 9. The shell is visible in the larger particles. The irregular thickness of this shell layer is evidence that this layer is not an optical artifact. This is also evident when adjusting the focus on the microscope: if this were an artifact, its thickness would change as the focus changed, and this does not occur.

The second type of particle that came out of the process was a large, millimeter-sized particle that clearly behaved as a solid-coated particle. In one experiment, a reddish-orange dye, methyl red, which is of low solubility in both water and ethyl acetate, was dissolved in the cubic phase prior to dispersing. In addition to a reddish-orange tinge to the microparticles seen in the microscope, the millimeter-sized particles were strongly red-orange, demonstrating that the cubic phase is encapsulated inside the PLGA. Millimeter-sized particles of this type could be suspended on the tip of a needle, for example, without flowing, in contrast with uncoated cubic phase which could not be suspended in this fashion.

Figure 10:
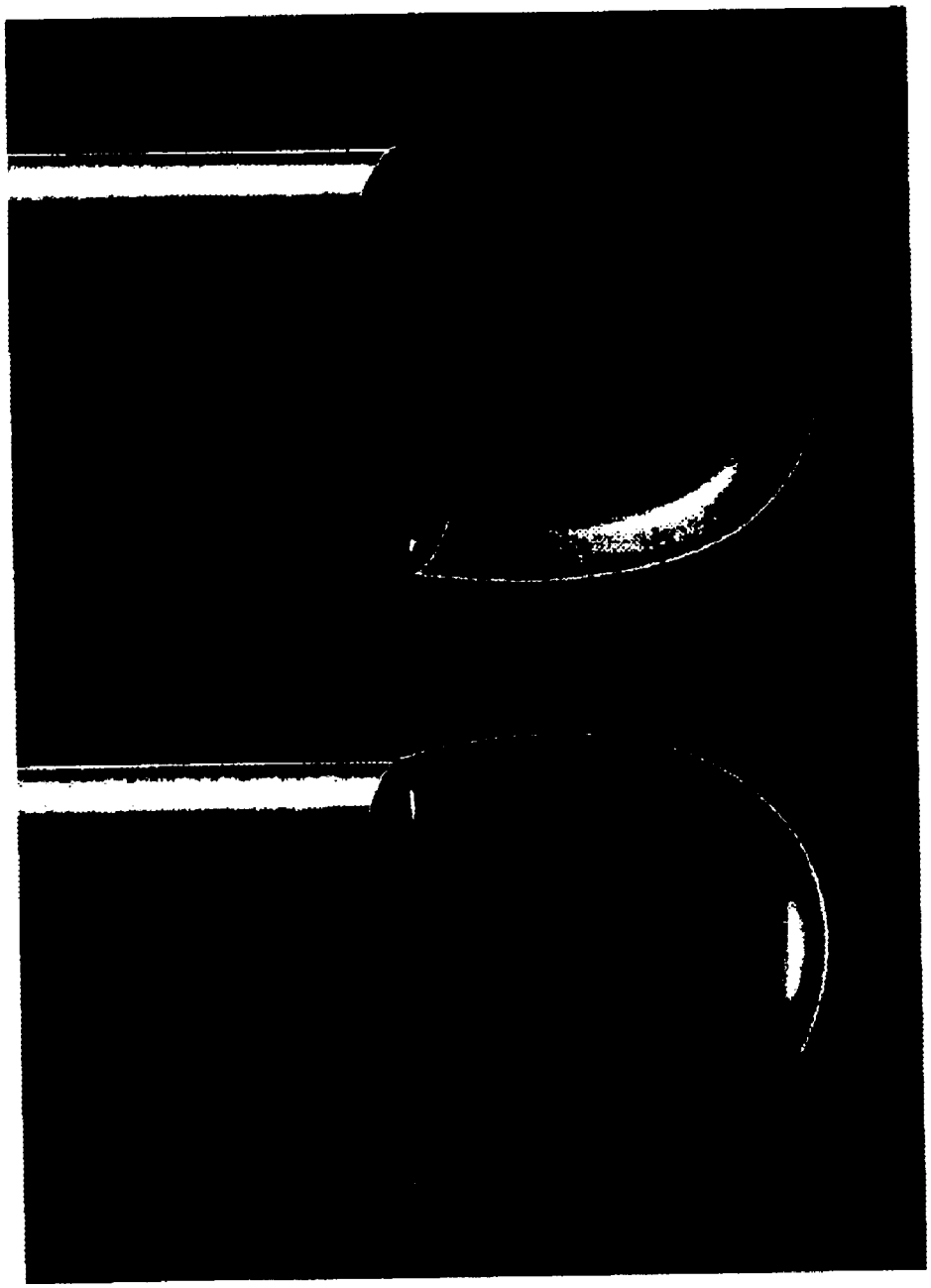
FIG. 10. On the left is a PLGA-coated cubic phase, made according to the instant invention, soaking in linalool, which is a non-solvent for PLGA but a solvent for the cubic phase. On the right, the same cubic phase was soaked in linalool under identical conditions, demonstrating that the cubic phase dissolves in the linalool when not coated.

One of these large particles was placed in linalool, which is a solvent for the cubic phase but not for the PLGA. The particle did not dissolve in this solvent even after one week, whereas the cubic phase without PLGA coating dissolved in less than 5 minutes. FIG. 10 shows a side-by-side comparison of the PLGA-coated (on the left) and uncoated (on the right) cubic phases soaking in linalool, demonstrating clearly the insolubility of the coated cubic phase—the original color photograph shows that there is essentially no color to the linalool for the PLGA-coated sample, whereas the linalool containing the uncoated cubic phase is strongly red-orange. This experiment proves that the cubic phase is truly encapsulated by the PLGA.

Example 40

Figure 11:
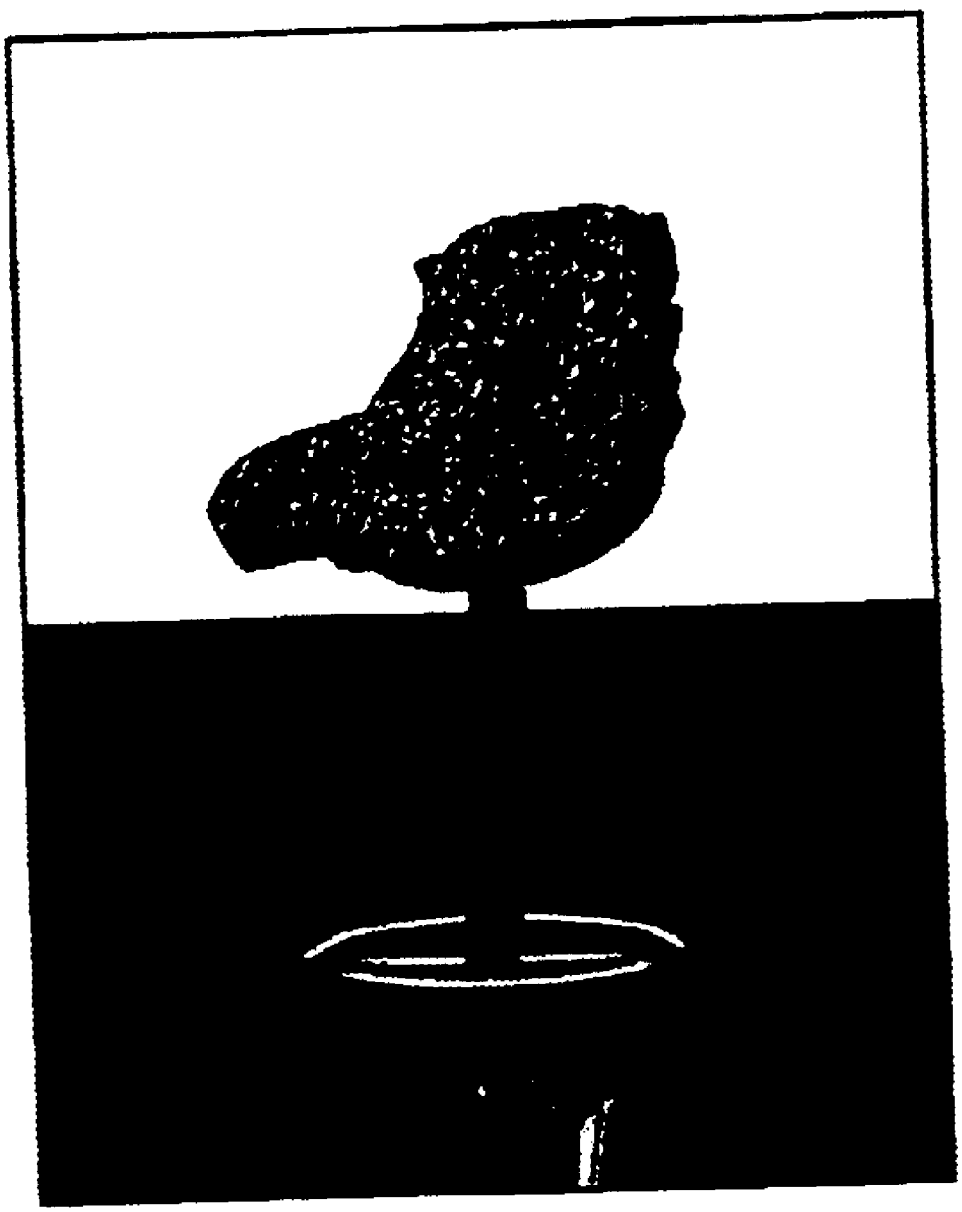
FIG. 11. A large (5 mm) particle of coated cubic phase in which the coating consists of amorphous trehalose, obtained by freeze-drying a dispersion of Arlatone G-based cubic phase in a trehalose solution.

A cubic phase containing solubilized methyl red was first prepared by mixing 2.118 grams of Arlatone G, 0.904 grams of water, 1.064 grams of oil of ginger, and 0.012 grams of methyl red, and stirring thoroughly. A trehalose solution was prepared by dissolving 2.00 grams of trehalose in 10.005 grams of water. Then 1.002 grams of the cubic phase were dispersed in the trehalose solution by a combination of shaking and mild sonication. This dispersion was then freeze-dried in a lyophilizer. Trehalose solutions are known to yield amorphous solid on freeze-drying. The resulting material flowed freely, and gave no hint of the greasy, sticky feel and behavior that characterizes the uncoated cubic phase. There was no second phase present, as the material was homogeneous to the eye, and had a strong, uniform, red-orange color. A large particle of the material was speared with the point of a push-pin and photographed, as shown in FIG. 11; an uncoated cubic phase would not have been possible to spear and suspend indefinitely in this fashion.

In the phase-contrast optical microscope, thin portions of this material were readily seen to contain a fine-scale structure, which is consistent with the presence of cubic phase microparticles (submicron to 5 microns in size) within the trehalose solid matrix. The material was brittle and could therefore be crushed into small particles with ease. Upon mixing the material into water at, say, a 1:10 ratio, a dispersion was immediately obtained which was indistinguishable in the optical microscope from dispersions of this cubic phase in water.

Example 41

This Example demonstrates a method of production of coated microparticles in which a precursor to the coating material, which is surface-active when dissolved in water, is used to disperse a cubic phase into particles; then after reacting to convert this precursor to a solid coating, energy input is again applied to reduce the particle size to submicron. As discussed above, one advantage of this method is that it localizes the coating precursor at the particle surface, so that the cubic phase readily becomes encapsulated upon conversion of this precursor to the coating. The active compound in this Example was triclosan.

A cubic phase was prepared by mixing 0.886 grams of linalool, 0.960 grams of Pluronic P123 (BASF), 0.104 grams of triclosan, 0.189 grams of 2-ethylhexanoic acid, and 0.879 grams of distilled water, and then stirring thoroughly. This cubic phase was then smeared onto the sides of a test tube, 3.33 grams of a sodium N-acetyltryptophan (Na-NAT) solution (6 wt % based on the NAT) overlain, and the mixture shaken and sonicated briefly to disperse the cubic phase; the Na-NAT thus acts as a dispersant or surfactant in this step. A 30% zinc acetate solution, in the amount 0.37 grams, was then added and mixed with the dispersion, followed by 0.52 grams of 2N NaOH. Five minutes were allowed for the reaction to begin, after which the material was further sonicated. A surfactant solution (0.10 grams) containing Cremophor EL (9%) and Pluronic F-68 (12.5%) was then added, and the mixture sonicated for 15 minutes. The solid-coated nature of the resulting microparticles was evident in phase contrast optical microscopy, where shearing the dispersion between glass and coverslip clearly showed that the microparticles behaved as solid-coated particles rather than as the readily-deformable cubic phase particles that result without application of the coating.

Example 42

This Example reports a process in which coating material is melted, and a cubic phase dispersed therein, following which the temperature is lowered to solidify the coating, after which energy input is applied to create particles. Such a process can be applied to crystalline materials as well as to amorphous or semi-crystalline coating materials, where in the case of an amorphous material the cooling may result in an amorphous material (and is thus not a true "freezing", but rather a vitrification).

The nutriceutical compound Coenzyme Q10 was incorporated into a cubic phase based on the ethoxylated, hydrogenated castor oil surfactant Arlatone G (from Uniquema). Coenzyme Q10 (10 mg) was solubilized in a mixture of 0.302 grams of essential oil of ginger, 0.201 grams of water, and 0.606 grams of Arlatone G. This cubic phase was placed in a test tube and 2.994 grams of hydrogenated cottonseed oil added, and the entire contents were heated to 90° C. to melt the oil. The sample was immediately sonicated in a hot water bath with vigorous shaking every 30 seconds, for 3 minutes. The test tube was then placed in an ice bath to solidify the oil with particles dispersed throughout the trigylceride. The resulting solid was then milled by the application of mechanical energy to an average particle size of several hundred microns; further reduction in size can readily be accomplished by milling methods well known in the art.

Example 43

This Example shows that a lectin incorporated into a cubic phase microparticle—the microparticle that would result after the dissolution of the zinc N-acetyltryptophan coating of a particle of the type produced in Example 41—retains its ability to bind oligosaccharides.

A cubic phase was first prepared by mixing 0.752 grams of Pluronic P123 (an insoluble surfactant), 0.705 grams of linalool, and 0.703 grams of water. An amount of 1.005 grams of this cubic phase was put in a glass flask together with 0.054 grams of the rhamnolipid surfactant JBR-99 (Jeneil Biosurfactant, Inc.) and 35 ml of pH 4.5 acetate buffer containing 4 mM $MnCl_2$ and 4 mM $CaCl_2$. The flask was then sonicated to disperse the cubic phase. Following this, the dispersion was microfluidized in a model 110S Microfluidizer (Microfluidics, Inc.) to a particle size that was fine enough where the absorbance measured on an Ultrospec 3000 UV-Vis spectrometer, at a wavelength of 620 nm, was about 0.2 absorbance units.

The following reagents were then added to 2 ml of the cubic phase dispersion: Anti Concanavalin A, Vector AS-2004, Lot 0321, 1 mg/ml stock solution prepared; working solution prepared by diluting 1:10 to 0.1 mg/ml: 51 microliters added. Concanavalin A, Sigma C-5275, Lot 60K8934 prepared as 1 mg/ml stock solution; working solution prepared by diluting 1:10 to 0.1 mg/ml: 16 microliters added. Biotinylated mannotriose, V-labs, NGB1336, prepare a 1 mg/ml stock solution, working solution prepared by diluting 1:100 to 0.01 mg/ml: 20 microliters added. HRP/Avidin; 0.28 mg/ml stock solution: 90 microliters added.

Fifteen minutes were allowed for diffusion and equilibration after the addition of the antibody and Con A solutions. Another fifteen minutes were allowed after the addition of the biotinylated mannatriose and HRP/avidin. To 10 drops of a Dextran Blue solution, at 3.9 mg/ml water, were added 6 drops of fast red TR salt, 2.4 mg/ml, 1 drop of 3% $H_2O_2$, and 800 ul 50 mM sodium acetate pH 4.5 containing 4 mM $MnCl_2$ and 4 mM $CaCl_2$. This solution has been found to show disappearance of absorbance at 620 nm upon addition of HRP, or the entire antibody-Con A-biotinylated mannatriose-avidin/HRP. At the end of all these additions, the total volume in the cuvette was 3.0 ml.

After the additiori of the Dextran Blue-based Detection System, absorbance readings at 620 nm were monitored continuously. After the readings stabilized at 0.40 absorbance units, 500 microliters of Displacement Solution were added. This solution was composed of saturated alpha methylmannoside in 50 mM sodium acetate pH 4.5 containing 4 mM $MnCl_2$ and 4 mM $CaCl_2$.

Upon addition of this alpha methylmannoside—the analyte—the absorbance dropped from 0.40 to 0.26 absorbance units. This decrease, 35%, is far greater than the 14% that one would expect based on the dilution from 3.0 to 3.5 ml volume, and was reproducible, as seen in several repetitions. The majority of the decrease in absorbance was due to the enzymatic action of displaced HRP on the Dextran Blue.

It is apparent that many modifications and variations of the invention may be made without departing from the spirit and scope of the present invention. It is understood that the invention is not confined to the particular construction and arrangement herein described, but embraces such modified forms of it as come within the appended claims. The specific embodiments described are given by way of example only and the invention is limited only by the terms of the appended claims.

I claim:

1. A coated particle comprising
   a. An interior core comprising a matrix consisting essentially of
      i. at least one nanostructured liquid phase or a dehydrated variant thereof,
      ii. at least one nanostructured liquid crystalline phase or a dehydrated variant thereof or
      iii. a combination of
         (1) at least one nanostructured liquid phase or a dehydrated variant thereof and
         (2) at least one nanostructured liquid crystalline phase or a dehydrated variant thereof and
   b. An exterior coating comprising nonlamellar domains.

2. The coated particle of claim 1, wherein said nanostructured liquid phase material comprises
   a. a nanostructured L1 phase material,
   b. a nanostructured L2 phase material,
   c. a microemulsion that is nanostructured, or
   d. a nanostructured L3 phase material.

3. The coated particle of claim 1, wherein said nanostructured liquid phase material comprises
   a. a nanostructured normal or reversed cubic phase material,
   b. a nanostructured normal or reversed hexagonal phase material,
   c. a nanostructured normal or reversed intermediate phase material, or
   d. a nanostructured lamellar phase material.

4. The coated particle of claim 1, wherein said nanostructured liquid phase material comprises
   a. a polar solvent and
   b. a surfactant or a lipid.

5. The coated particle of claim 1, wherein said nanostructured liquid phase material comprises
   a. a polar solvent,
   b. a surfactant or a lipid and
   c. an amphiphile or hydrophobe.

6. The coated particle of claim 1, wherein said nanostructured liquid phase material comprises
   a. a block copolymer.

7. The coated particle of claim 1, wherein said nanostructured liquid phase material comprises
   a. a block copolymer and
   b. a solvent.

8. The coated particle of claim 1, wherein said nanostructured liquid phase material comprises
   a. a polar solvent and
   b. a surfactant.

9. The coated particle of claim 1, wherein said nanostructured liquid phase material comprises
   a. a polar solvent,
   b. a surfactant and
   c. an amphiphile or hydrophobe.

10. The coated particle of claim 1, wherein said nanostructured liquid phase material comprises
    a. a block copolymer.

11. The coated particle of claim 1, wherein said nanostructured liquid phase material comprises
    a. a block copolymer and
    b. a solvent.

12. The coated particle of claim 1, wherein said interior core comprises an active agent disposed within said matrix.

13. The coated particle of claim 12, wherein said an active agent comprises paclitaxel.

14. The coated particle of claim 12, wherein said an active agent comprises capsaicin.

15. The coated particle of claim 12, wherein said an active agent comprises a photodynamic therapeutic agent.

16. The coated particle of claim 12, wherein said an active agent comprises an imaging agent.

17. The coated particle of claim 12, wherein said an active agent comprises a receptor protein.

18. The coated particle of claim 1, wherein said interior core comprises a reversed cubic phase material.

19. The coated particle of claim 18, wherein said interior core comprises an active agent disposed within said matrix.

20. The coated particle of claim 19, wherein said active agent comprises paclitaxel.

21. The coated particle of claim 19, wherein said active agent comprises capsaicin.

22. The coated particle of claim 19, wherein said active agent comprises a photodynamic therapeutic agent.

23. The coated particle of claim 19, wherein said active agent comprises a nucleic acid.

24. The coated particle of claim 19, wherein said active agent comprises a glycolipid.

25. The coated particle of claim 19, wherein said active agent comprises an amino acid.

26. The coated particle of claim 19, wherein said active agent comprises a polypeptide.

27. The coated particle of claim 19, wherein said active agent comprises a protein.

28. The coated particle of claim 19, wherein said active agent comprises an antineoplastic therapeutic agent.

29. The coated particle of claim 19, wherein said active agent comprises an antihypertneisve agent.

30. The coated particle of claim 19, wherein said active agent comprises a rodent deterrent agent.

31. The coated particle of claim 19, wherein said active agent comprises a pheremone.

32. The coated particle of claim 19, wherein said active agent comprises a receptor protein.

33. A coated particle as defined by claim 1, wherein said matrix comprises a material having the physicochemical properties of a biomembrane.

34. A coated particle as defined by claim 33, wherein said biomembrane material comprises a biologically active polypeptide material.

35. A coated particle as defined by claim 33, wherein said matrix comprises a polypeptide or a protein immobilized in said biomembrane material.

36. The coated particle of claim 1 wherein said nonlamellar domain is amorphous.

37. The coated particle of claim 1 wherein said nonlamellar domain is a polymer.

38. The coated particle of claim 37 wherein said polymer is PLGA.

39. The coated particle of claim 36 wherein said nonlamellar domain comprises a sugar.

40. The coated particle of claim 39 wherein said sugar is trehalose.

41. The coated particle of claim 1 wherein said exterior coating comprises a semi-crystalline nonlamellar material.

42. The coated particle of claim 1 wherein said exterior coating comprises an imaging agent.

43. The coated particle of claim 1 wherein said exterior coating comprises a protein.

44. The coated particle of claim 1 wherein said exterior coating comprises at least 2% nonlamellar domains.

45. The coated particle of claim 1 wherein said exterior coating comprises at least 10% nonlamellar domains.

46. The coated particle of claim 1 wherein said exterior coating comprises at least 50% nonlamellar domains.

47. The coated particle of claim 1 wherein said exterior coating comprises a pharmaceutical active.

48. A coated particle comprising
   a. An interior core comprising a matrix consisting essentially of
      i. at least one nanostructured liquid phase,
      ii. at least one nanostructured liquid crystalline phase or
      iii. a combination of
         (1) at least one nanostructured liquid phase and
         (2) at least one nanostructured liquid crystalline phase and
   b. An exterior coating comprising nonlamellar domains.

49. A coated particle comprising
   a. An interior core comprising a matrix consisting essentially of
      i. at least one nanostructured liquid phase,
      ii. at least one nanostructured liquid crystalline phase or
      iii. a combination of
         (1) at least one nanostructured liquid phase and
         (2) at least one nanostructured liquid crystalline phase and
   b. An exterior coating comprising a nonlamellar material.

50. A method of making a coated particle comprising
   a. An interior core comprising a matrix consisting essentially of
      i. at least one nanostructured liquid phase,
      ii. at least on nanostructured liquid crystalline phase or
      iii. a combination of
         (1) at least one nanostructured liquid phase and
         (2) at least one nanostructured liquid crystalline phase and
   b. An exterior coating comprising a nonlamellar material comprising
      providing a volume of said matrix that includes at least on chemical species having a moiety capable of forming a nonlamellar material upon reaction with a second moiety and
      contacting said volume with a fluid containing at least one chemical species having said second moiety to react said first moiety with said second moiety and contemporaneously subdividing said volume into particles by the application of energy to said volume.

51. A method of making a coated particle comprising
   a. An interior core comprising a matrix consisting essentially of
      i. at least one nanostructured liquid phase,
      ii. at least on nanostructured liquid crystalline phase or
      iii. a combination of
         (1) at least one nanostructured liquid phase and
         (2) at least one nanostructured liquid crystalline phase and
   b. An exterior coating comprising a nonlamellar material comprising
      providing a volume of said matrix that includes said nonlamellar material dissolved therein and
      causing said nonlamellar material to become insoluble in said matrix and contemporaneously subdividing said volume into particles by the application of energy to said volume.

52. A method of making a coated particle comprising
   a. An interior core comprising a matrix consisting essentially of
      i. at least one nanostructured liquid phase,
      ii. at least on nanostructured liquid crystalline phase or
      iii. a combination of
         (1) at least one nanostructured liquid phase and
         (2) at least one nanostructured liquid crystalline phase and
   b. An exterior coating comprising a nonlamellar material comprising
      providing a volume of said matrix that includes said nonlamellar material dissolved therein and that includes at least one chemical species having a moiety capable of forming said nonlamellar material upon reaction with a second moiety and
      contacting said volume with a fluid containing at least one chemical species having said second moiety to react said first moiety with said second moiety and contemporaneously causing said nonlamellar material to become insoluble in said matrix and subdividing said volume into particles by the application of energy to said volume.

53. A method of making a coated particle comprising
   a. An interior core comprising a matrix consisting essentially of
      i. at least one nanostructured liquid phase,
      ii. at least on nanostructured liquid crystalline phase or
      iii. a combination of
         (1) at least one nanostructured liquid phase and
         (2) at least one nanostructured liquid crystalline phase and
   b. An exterior coating comprising a first nonlamellar material and a second nonlamellar material comprising
      providing a volume of said matrix that includes said first nonlamellar material dissolved therein and that includes at least one chemical species having a moiety capable of forming said second nonlamellar material upon reaction with a second moiety and
      contacting said volume with a fluid containing at least one chemical species having said second moiety to react said first moiety with said second moiety and contemporaneously causing said first nonlamellar material to become insoluble in said matrix and subdividing said volume into particles by the application of energy to said volume.

54. A method of making a coated particle comprising
   a. An interior core comprising a matrix consisting essentially of
      i. at least one nanostructured liquid phase,
      ii. at least one nanostructured liquid crystalline phase or
      iii. a combination of
         (1) at least one nanostructured liquid phase and
         (2) at least one nanostructured liquid crystalline phase and
   b. An exterior coating comprising a nonlamellar material comprising
      dispersing a volume of said matrix in a form of said nonlamellar material selected from the group consisting of liquefied form, solution, or fluid precursor, and
      solidifying said nonlamellar material by a techniques selected from the group consisting of cooling, evaporating a volatile solvent, or implementing a chemical reaction.

55. A method of making a coated particle comprising
a. An interior core comprising a matrix consisting essentially of
i. at least one nanostructured liquid phase,
ii. at least one nanostructured liquid crystalline phase or
iii. a combination of
(1) at least one nanostructured liquid phase and
(2) at least one nanostructured liquid crystalline phase and
b. An exterior coating comprising a nonlamellar material comprising
dispersing particles of said matrix into a fluid that includes at least one chemical species having a moiety capable of forming a nonlamellar material upon reaction or association with a second moiety and
adding to said dispersion at least one chemical species having said second moiety to react said first moiety with said second moiety.

56. A method as in claim 55 wherein said chemical species having said first moiety is preferentially associated with the particles of said matrix at the time the chemical species having said second moiety is added.

57. A method of making a coated particle comprising
a. An interior core comprising a matrix consisting essentially of
i. at least one nanostructured liquid phase,
ii. at least one nanostructured liquid crystalline phase or
iii. a combination of
(1) at least one nanostructured liquid phase and
(2) at least one nanostructured liquid crystalline phase and
b. An exterior coating comprising a nonlamellar material comprising
dispersing particles of said matrix into a fluid that includes at least one chemical species having a moiety capable of forming a nonlamellar material upon reaction or association with a second moiety and
adding to said dispersion at least one chemical species having said second moiety to react said first moiety with said second moiety and
subdividing the resulting material into particles by the application of energy to said material.

58. A method as in claim 57 wherein said chemical species having said first moiety is preferentially associated with the particles of said matrix at the time the chemical species having said second moiety is added.

59. A method of making a coated particle comprising
a. An interior core comprising a matrix consisting essentially of
i. at least one nanostructured liquid phase,
ii. at least one nanostructured liquid crystalline phase or
iii. a combination of
(1) at least one nanostructured liquid phase and
(2) at least one nanostructured liquid crystalline phase and
b. An exterior coating comprising a nonlamellar material comprising
dispersing or dissolving a volume of said matrix in a liquid comprising said nonlamellar material in solution or dispersed form and comprising also a volatile solvent, and
spray-drying said solution or dispersion.

60. A method of using a coated particle comprising
a. An interior core comprising a matrix consisting essentially of
i. at least one nanostructured liquid phase,
ii. at least on nanostructured liquid crystalline phase or
iii. a combination of
(1) at least one nanostructured liquid phase and
(2) at least one nanostructured liquid crystalline phase and
b. An exterior coating comprising a nonlamellar material comprising
disposing said particle in a fluid medium comprising an adsorbable material and adsorbing said adsorbable material on said exterior coating.

61. A method of using a coated particle comprising
a. An interior core comprising a matrix consisting essentially of
i. at least one nanostructured liquid phase,
ii. at least on nanostructured liquid crystalline phase or
iii. a combination of
(1) at least one nanostructured liquid phase and
(2) at least one nanostructured liquid crystalline phase and
b. An exterior coating comprising a nonlamellar material comprising
disposing said particle in a fluid medium comprising an absorbable material and absorbing said absorbable material in said interior core.

62. The method of claim 61 wherein said absorbing is triggered by dissolution of said exterior coating by said fluid medium.

63. The method of claim 61 wherein said absorbing is triggered by disruption of said exterior coating.

64. The method of claim 61 wherein said absorbing occurs through pores in said exterior coating.

65. A method of using a coated particle comprising
a. An interior core comprising a matrix consisting essentially of
i. at least one nanostructured liquid phase,
ii. at least on nanostructured liquid crystalline phase or
iii. a combination of
(1) at least one nanostructured liquid phase and
(2) at least one nanostructured liquid crystalline phase and
b. An exterior coating comprising a nonlamellar material comprising
disposing said particle in a fluid medium comprising an absorbable material and absorbing said absorbable material in said exterior coating.

66. A method of using a coated particle comprising
a. An interior core comprising a matrix consisting essentially of
i. at least one nanostructured liquid phase,
ii. at least on nanostructured liquid crystalline phase or
iii. a combination of
(1) at least one nanostructured liquid phase and
(2) at least one nanostructured liquid crystalline phase and
b. An exterior coating comprising a nonlamellar material comprising
disposing said particle in a fluid medium comprising an absorbable material and absorbing said absorbable material in said interior core and exterior coating.

67. A method of using a coated particle comprising
a. An interior core comprising a matrix consisting essentially of
i. at least one nanostructured liquid phase,
ii. at least on nanostructured liquid crystalline phase or
iii. a combination of
(1) at least one nanostructured liquid phase and
(2) at least one nanostructured liquid crystalline phase, said matrix comprising an active agent disposed therein, and
b. An exterior coating comprising a nonlamellar material comprising
disposing said particle in a fluid medium and
releasing said active agent into said fluid medium.

68. The method of claim 67, wherein said release is triggered by dissolution of said exterior coating by said fluid medium.

69. The method of claim 67, wherein said release is triggered by disruption of said exterior coating.

70. The method of claim 67, wherein said release is occurs through pores in said exterior coating.

71. A method of using a coated particle comprising
a. An interior core comprising a matrix consisting essentially of
i. at least one nanostructured liquid phase,
ii. at least on nanostructured liquid crystalline phase or
iii. a combination of
(1) at least one nanostructured liquid phase and
(2) at least one nanostructured liquid crystalline phase, said matrix comprising an active agent disposed therein, and
b. An exterior coating comprising a nonlamellar material comprising
releasing said active agent.

72. The method of claim 71, wherein said release is triggered by dissolution of said exterior coating.

73. The method of claim 71, wherein said release is triggered by disruption of said exterior coating.

74. The method of claim 71, wherein said release is occurs through pores in said exterior coating.

75. A coated particle comprising
a. an interior core comprising a matrix consisting essentially of
i. at least one nanostructured liquid phase,
ii. at least one nanostructured liquid crystalline phase or
iii. a combination of
(1) at least one nanstructured liquid phase and
(2) at least one nanostructured liquid crystalline phase and
b. an exterior coating comprising nonlamellar domains, and
c. a targeting moiety associated with said coated particle.

76. The coated particle of claim 75, wherein said nonlamellar domains comprise material selected from the group consisting of nonlamellar crystalline material, nonlamellar amorphous material, and nonlamellar semi-crystalline material.

77. The coated particle of claim 75 wherein said targeting moiety is selected from the group consisting of protein, nucleic acid, polysaccharide and magnetically responsive material.

78. The coated particle of claim 75 wherein said targeting moiety is associated with said exterior coating of said coated particle.

79. The coated particle of claim 78 wherein said targeting moiety is adsorbed to an inner surface of said exterior coating of said coated particle.

80. The coated particle of claim 78 wherein said targeting moiety is embedded in said exterior coating of said coated particle.

81. The coated particle of claim 78 wherein said targeting moiety is associated with an outer surface of said exterior coating of said coated particle.

82. The coated particle of claim 81 wherein said targeting moiety is associated with said outer surface of said exterior coating of said coated particle by a means selected from the group consisting of adsorption, covalent bonding, ionic bonding, hydrogen bonding, and hydrophobic interactions.

83. The coated particle of claim 75 wherein said targeting moiety is associated with the interior core of said coated particle.

84. The coated particle of claim 75 wherein said targeting moiety is associated with a phase present between said exterior coating and said interior core.

85. The coated particle of claim 75 wherein said targeting moiety is associated by a means selected from the group consisting of covalent bonding, ionic bonding, adsorption, absorption, hydrogen bonding, and hydrophobic interactions.

86. The coated particle of claim 75 wherein said targeting moiety is associated with said coated particle via a flexible spacer molecule.

87. The coated particle of claim 75 wherein said exterior coating comprises at least 2% nonlamellar domains.

88. The coated particle of claim 75 wherein said exterior coating comprises at least 10% nonlamellar domains.

89. The coated particle of claim 75 wherein said exterior coating comprises at least 50% nonlamellar domains.

90. A coated particle comprising
a. an interior core comprising a matrix consisting essentially of
i. at least one nanostructured liquid phase,
ii. at least one nanostructured liquid crystalline phase or
iii. a combination of
(1) at least one nanstructured liquid phase and
(2) at least one nanostructured liquid crystalline phase and
b. an exterior coating comprising nonlamellar domains, and
c. a bioactive agent associated with said coated particle.

91. The coated particle of claim 90, wherein said nonlamellar domains comprise material selected from the group consisting of nonlamellar crystalline material, nonlamellar amorphous material, and nonlamellar semi-crystalline material.

92. The coated particle of claim 90 wherein said bioactive agent is selected from the group consisting of adsorption enhancers, adsorption-modulating materials, vaccine adjuvants, antibodies, steroids, hormones, oligosaccharides, polysaccharides, modulators of protein binding activity, lectins, receptors, nucleic acids, proteins.

93. The coated particle of claim 90 wherein said bioactive agent is associated with said exterior coating of said coated particle.

94. The coated particle of claim 90 wherein said bioactive agent is adsorbed to an inner surface of said exterior coating of said coated particle.

95. The coated particle of claim 90 wherein said bioactive agent is embedded in said exterior coating of said coated particle.

96. The coated particle of claim 90 wherein said bioactive agent is associated with an outer surface of said exterior coating of said coated particle.

97. The coated particle of claim 90 wherein said bioactive agent is associated with said outer surface of said exterior coating of said coated particle by a means selected from the group consisting of adsorption, covalent bonding, ionic bonding, hydrogen bonding, and hydrophobic interactions.

98. The coated particle of claim 90 wherein said bioactive agent is associated with the interior core of said coated particle.

99. The coated particle of claim 90 wherein said bioactive agent is associated with a phase present between said exterior coating and said interior core.

100. The coated particle of claim 90 wherein said bioactive agent is associated by a means selected from the group consisting of covalent bonding, ionic bonding, adsorption, absorption, hydrogen bonding, and hydrophobic interactions.

101. The coated particle of claim 90 wherein said bioactive agent is associated with said coated particle via a flexible spacer molecule.

102. The coated particle of claim 90 wherein said exterior coating comprises at least 2% nonlamellar domains.

103. The coated particle of claim 90 wherein said exterior coating comprises at least 10% nonlamellar domains.

104. The coated particle of claim 90 wherein said exterior coating comprises at least 50% nonlamellar domains.

105. A coated particle comprising
   a. An interior core comprising a matrix consisting essentially of
      i. at least one polymerized nanostructured liquid phase or a dehydrated variant thereof,
      ii. at least one polymerized nanostructured liquid crystalline phase or a dehydrated variant thereof or
      iii. a combination of
         (1) at least one polymerized nanostructured liquid phase or a dehydrated variant thereof and
         (2) at least one polymerized nanostructured liquid crystalline phase or a dehydrated variant thereof and
   b. An exterior coating comprising nonlamellar domains.

106. The coated particle of claim 105, wherein said polymerized nanostructured liquid phase material comprises
   a. a polymerized nanostructured normal or reversed cubic phase material,
   b. a polymerized nanostructured normal or reversed hexagonal phase material,
   c. a polymerized nanostructured normal or reversed intermediate phase material, or
   d. a polymerized nanostructured lamellar phase material.

107. The coated particle of claim 105, wherein said polymerized nanostructured liquid phase material comprises
   a. a polymerized nanostructured normal or reversed cubic phase material, or
   b. a polymerized nanostructured normal or reversed hexagon al phase material.

\* \* \* \* \*

UNITED STATES PATENT AND TRADEMARK OFFICE
CERTIFICATE OF CORRECTION

| | |
|---|---|
| PATENT NO. | : 6,638,621 B2 |
| DATED | : October 28, 2003 |
| INVENTOR(S) | : Anderson |

It is certified that error appears in the above-identified patent and that said Letters Patent is hereby corrected as shown below:

Column 87,
Lines 27-28, 52-53, 56-57 and 61-62, replace "nanostructured liquid phase" with -- nanostructured liquid crystalline phase --

Column 88,
Lines 1-2, replace "nanostructured liquid phase" with -- nanostructured liquid crystalline phase --
Line 29, replace "hypertneisve" with -- hypertensive --

Column 89,
Lines 37 and 45, replace "on" with -- one --.

Column 93,
Line 47, replace "nanstructured" with -- nanostructured --

Column 94,
Line 38, replace "nanstructured" with -- nanostructured --

Column 96,
Lines 10 and 19, replace "polymerized nanostructured liquid phase" with -- polymerized nanostructured liquid crystalline phase --

Signed and Sealed this

Twenty-third Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,638,621 B2
DATED : October 28, 2003
INVENTOR(S) : Anderson

It is certified that error appears in the above-identified patent and that said Letters Patent is hereby corrected as shown below:

Column 87,
Lines 27-28, 52-53, 56-57 and 61-62, replace "nanostructured liquid phase" with -- nanostructured liquid crystalline phase --

Column 88,
Lines 1-2, replace "nanostructured liquid phase" with -- nanostructured liquid crystalline phase --
Line 40, replace "hypertneisve" with -- hypertensive --

Column 89,
Lines 37 and 45, replace "on" with -- one --.

Column 93,
Line 47, replace "nanstructured" with -- nanostructured --

Column 94,
Line 38, replace "nanstructured" with -- nanostructured --

Column 96,
Lines 11 and 20, replace "polymerized nanostructured liquid phase" with -- polymerized nanostructured liquid crystalline phase --

This certificate supersedes Certificate of Correction issued December 23, 2003.

Signed and Sealed this

Thirtieth Day of March, 2004

JON W. DUDAS
*Acting Director of the United States Patent and Trademark Office*